(12) United States Patent
Jeong et al.

(10) Patent No.: US 9,876,180 B2
(45) Date of Patent: Jan. 23, 2018

(54) ORGANIC LIGHT EMITTING DEVICE AND DISPLAY DEVICE HAVING THE SAME

(71) Applicant: SAMSUNG DISPLAY CO., LTD., Yongin-si, Gyeonggi-do (KR)

(72) Inventors: Hyein Jeong, Suwon-si (KR); Jungsub Lee, Suwon-si (KR)

(73) Assignee: SAMSUNG DISPLAY CO., LTD., Yongin-si, Gyeonggi-Do (KR)

( * ) Notice: Subject to any disclaimer, the term of this patent is extended or adjusted under 35 U.S.C. 154(b) by 0 days.

(21) Appl. No.: 15/207,529

(22) Filed: Jul. 12, 2016

(65) Prior Publication Data

US 2017/0162796 A1 Jun. 8, 2017

(30) Foreign Application Priority Data

Dec. 3, 2015 (KR) .......................... 10-2015-0171669

(51) Int. Cl.
*H01L 51/00* (2006.01)
*C07D 209/86* (2006.01)
(Continued)

(52) U.S. Cl.
CPC ........ *H01L 51/0072* (2013.01); *C07D 209/86* (2013.01); *C07D 241/38* (2013.01); *C07D 241/42* (2013.01); *C07D 241/48* (2013.01); *C07D 263/57* (2013.01); *C07D 265/36* (2013.01); *C07D 403/04* (2013.01); *C07D 405/04* (2013.01); *C07D 409/04* (2013.01); *C07F 9/65583* (2013.01); *C07F 9/650994* (2013.01); *C09K 11/025* (2013.01); *H01L 51/0052* (2013.01); *H01L 51/0054* (2013.01); *H01L 51/0058* (2013.01);
(Continued)

(58) Field of Classification Search
CPC ............ H01L 51/0072; H01L 51/0052; H01L 51/0054; H01L 51/0058; H01L 51/0067; H01L 51/0071; H01L 51/0073; H01L 51/0074; C07D 209/86; C07D 241/38; C07D 241/42; C07D 241/48; C07D 263/57; C07D 265/36; C07D 403/04; C07D 405/04; C07D 409/04; C07F 9/650994; C09K 11/025
See application file for complete search history.

(56) References Cited

U.S. PATENT DOCUMENTS 5,895,692 A * 4/1999 Shirasaki ............... H05B 33/10 313/504
8,174,001 B2 * 5/2012 Kitamura ............ H01L 51/5016 257/13
(Continued)

FOREIGN PATENT DOCUMENTS

KR 10-0730132 B1 6/2007
KR 10-2015-0071685 A 6/2015

*Primary Examiner* — Ida M Soward
(74) *Attorney, Agent, or Firm* — Lee & Morse, P.C.

(57) ABSTRACT

An organic light emitting device and a display device including the same, the organic light emitting device including a first electrode; a hole controlling layer on the first electrode; an emission layer on the hole controlling layer; an electron controlling layer on the emission layer; and a second electrode on the electron controlling layer, wherein the emission layer includes a hole transport host material, an electron transport host material, a bipolar host material, and at least one dopant material.

20 Claims, 4 Drawing Sheets

(51) Int. Cl.
*C09K 11/02* (2006.01)
*C07D 241/38* (2006.01)
*C07D 409/04* (2006.01)
*C07D 405/04* (2006.01)
*C07D 403/04* (2006.01)
*C07D 241/42* (2006.01)
*C07D 241/48* (2006.01)
*C07D 265/36* (2006.01)
*C07D 263/57* (2006.01)
*C07F 9/6509* (2006.01)
*C07F 9/6558* (2006.01)
*H01L 51/50* (2006.01)
*H01L 27/32* (2006.01)

(52) U.S. Cl.
CPC ...... *H01L 51/0067* (2013.01); *H01L 51/0071* (2013.01); *H01L 51/0073* (2013.01); *H01L 51/0074* (2013.01); *H01L 27/3244* (2013.01); *H01L 51/5016* (2013.01); *H01L 2251/5384* (2013.01)

(56) References Cited

U.S. PATENT DOCUMENTS

| | | | | |
|---|---|---|---|---|
| 8,981,351 | B2* | 3/2015 | Hamada | H01L 51/5012 257/40 |
| 2006/0192471 | A1* | 8/2006 | Inoue | H01L 51/5265 313/113 |
| 2006/0231843 | A1* | 10/2006 | Qin | H01L 51/5016 257/79 |
| 2006/0261731 | A1* | 11/2006 | Aziz | H01L 27/3209 313/504 |
| 2006/0263631 | A1* | 11/2006 | Lee | H01L 51/0051 428/690 |
| 2008/0027028 | A1* | 1/2008 | Chichak | A61K 31/695 514/63 |
| 2008/0057609 | A1* | 3/2008 | Li | H01L 51/002 438/45 |
| 2011/0204295 | A1* | 8/2011 | Kuwabara | C07D 495/14 252/500 |
| 2012/0223346 | A1* | 9/2012 | Ohsawa | H01L 27/3206 257/89 |
| 2012/0235127 | A1* | 9/2012 | Takasu | H01L 51/504 257/40 |
| 2013/0320368 | A1* | 12/2013 | Seo | H01L 27/3206 257/89 |
| 2014/0151664 | A1* | 6/2014 | Sato | C09K 11/06 257/40 |
| 2014/0187791 | A1* | 7/2014 | Suzuki | C07D 209/86 548/405 |
| 2015/0129852 | A1 | 5/2015 | Park et al. | |
| 2015/0287952 | A1* | 10/2015 | Yamazaki | H01L 51/5016 257/40 |
| 2016/0036007 | A1* | 2/2016 | Facchetti | H01L 51/5203 257/40 |
| 2016/0311799 | A1* | 10/2016 | Low | C07D 209/86 |
| 2017/0170407 | A1* | 6/2017 | Park | H01L 51/0072 |

* cited by examiner

ORGANIC LIGHT EMITTING DEVICE AND DISPLAY DEVICE HAVING THE SAME

CROSS-REFERENCE TO RELATED APPLICATION

Korean Patent Application No. 10-2015-0171669, filed on Dec. 3, 2015, in the Korean Intellectual Property Office, and entitled: "Organic Light Emitting Device and Display Device Having the Same," is incorporated by reference herein in its entirety.

BACKGROUND

1. Field

Embodiments relate to an organic light emitting device and a display device having the same.

2. Description of the Related Art

An organic light emitting device is a self-luminescent type device and has wide viewing angles and good contrast. In addition, the organic light emitting device has rapid response time, high luminescence, and a low driving voltage.

Generally, an organic light emitting device includes an anode, and a hole transport layer, an emission layer, an electron transport layer, and a cathode disposed one by one on the anode. In this case, the hole transport layer, the emission layer, and the electron transport layer are organic thin films formed using organic compounds.

SUMMARY

Embodiments are directed to an organic light emitting device and a display device having the same.

The embodiments may be realized by providing an organic light emitting device, including a first electrode; a hole controlling layer on the first electrode; an emission layer on the hole controlling layer; an electron controlling layer on the emission layer; and a second electrode on the electron controlling layer, wherein the emission layer includes a hole transport host material, an electron transport host material, a bipolar host material, and at least one dopant material.

The bipolar host material may be a compound represented by the following Formula 1:

[Formula 1]

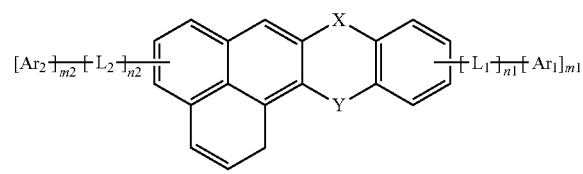

wherein, in Formula 1, X and Y are each independently one of NR, S, O or Si, R is a substituted or unsubstituted aryl group having 6 to 40 ring carbon atoms, or a substituted or unsubstituted heteroaryl group having 5 to 40 ring carbon atoms, $L_1$ and $L_2$ are each independently selected from hydrogen, deuterium, a halogen atom, an amino group, a nitro group, a nitrile group, an alkyl group having 1 to 40 carbon atoms, an alkenyl group having 2 to 40 carbon atoms, an alkynyl group having 2 to 40 carbon atoms, an aryl group having 5 to 40 ring carbon atoms, a heteroaryl group having 1 to 40 ring carbon atoms, an alkoxy group having 1 to 40 carbon atoms, an aryloxy group having 5 to 40 carbon atoms, an alkylamino group having 1 to 40 carbon atoms, an arylamino group having 5 to 40 carbon atoms, a diarylamino group having 5 to 40 carbon atoms, a heteroarylamino group having 5 to 40 carbon atoms, a diheteroarylamino group having 2 to 40 carbon atoms, an arylakyl group having 6 to 40 carbon atoms, a heteroarylalkyl group having 6 to 40 carbon atoms, a cycloalkyl group having 3 to 40 carbon atoms, a halogenalkyl group having 1 to 40 carbon atoms, a heterocycloalkyl group having 3 to 40 carbon atoms, an alkylsilyl group having 3 to 40 carbon atoms, an arylsilyl group having 3 to 40 carbon atoms, and a heteroarylsilyl group having 3 to 40 carbon atoms, $Ar_1$ and $Ar_2$ are each independently selected from a substituted or unsubstituted aryl group having 5 to 60 ring carbon atoms, a substituted or unsubstituted heteroaryl group having 3 to 60 ring carbon atoms, and a substituted or unsubstituted condensed polycyclic group having 6 to 60 ring carbon atoms, and n1, n2, m1, and m2 are each independently 0 or 1.

The bipolar host material represented by Formula 1 may be represented by the following Formula 2:

[Formula 2]

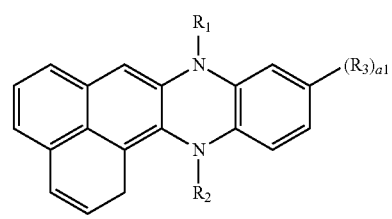

wherein, in Formula 2, $R_1$ to $R_3$ are each independently a substituted or unsubstituted aryl group having 6 to 40 ring carbon atoms or a substituted or unsubstituted heteroaryl group having 5 to 40 ring carbon atoms, and a1 is 0 or 1.

At least one of $R_1$ to $R_3$ may be the substituted or unsubstituted heteroaryl group having 5 to 40 ring carbon atoms, and the substituted or unsubstituted heteroaryl group having 5 to 40 ring carbon atoms may include a heteroatom selected from N, S, or O.

$R_1$ to $R_3$ may each independently be one of the following groups, in which * is a bonding location:

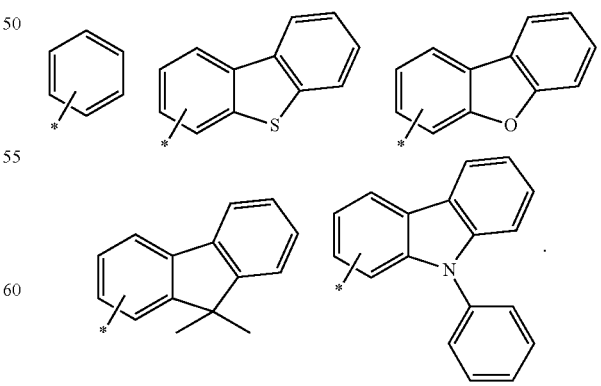

The bipolar host material represented by Formula 1 may be one of the following Compounds H-1 to H-9:

H-1
H-2
H-3
H-4
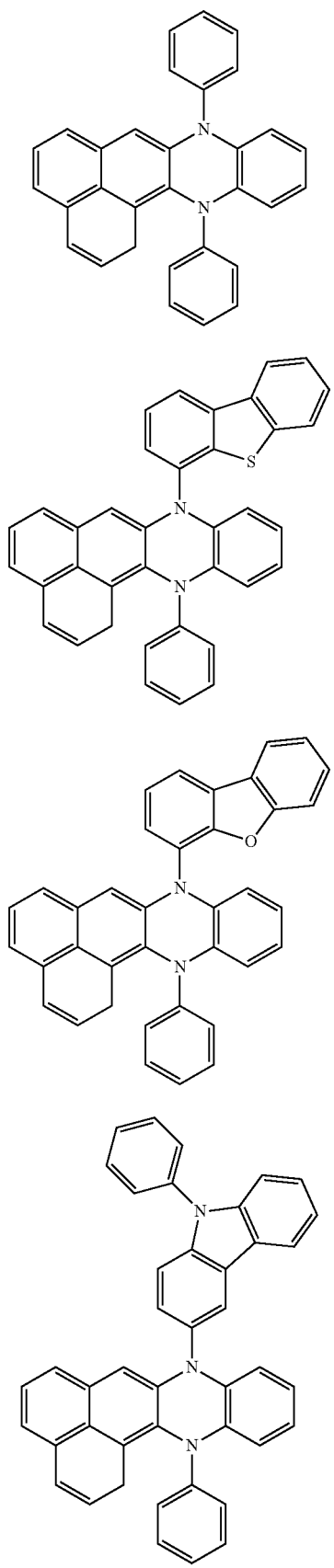
-continued
H-5
H-6
H-7
H-8
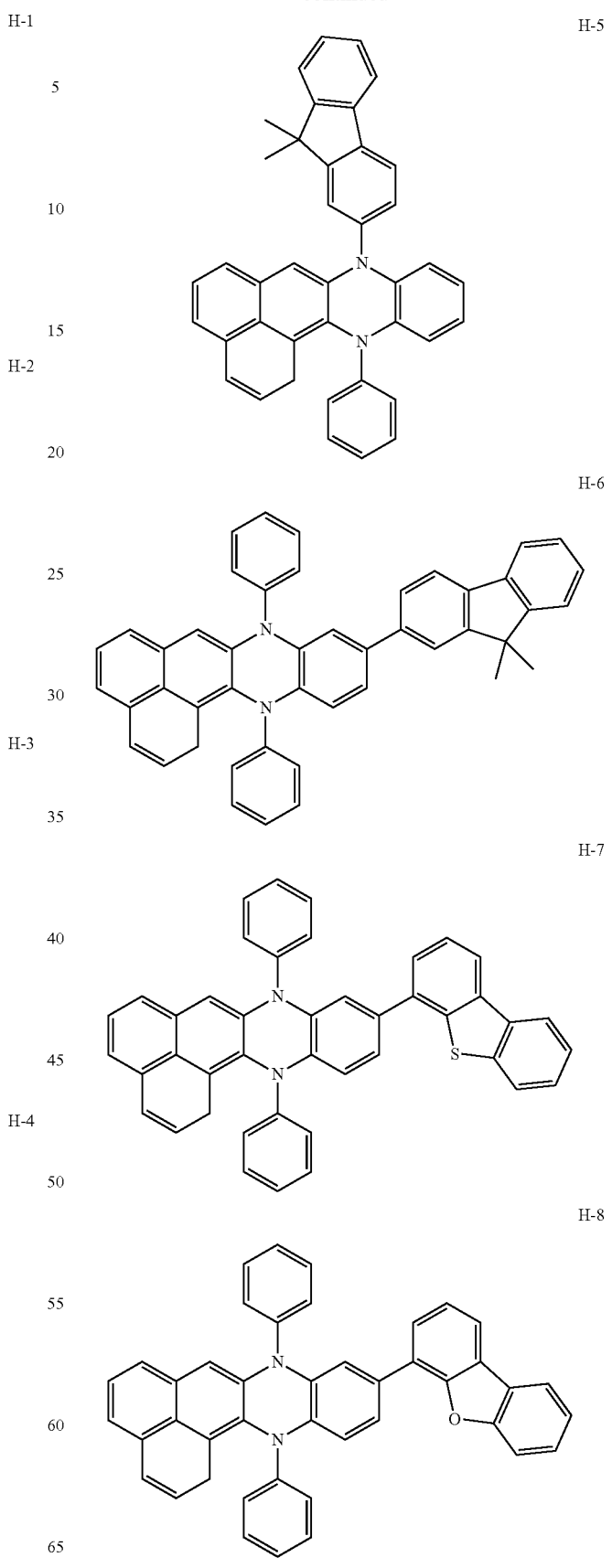

H-9

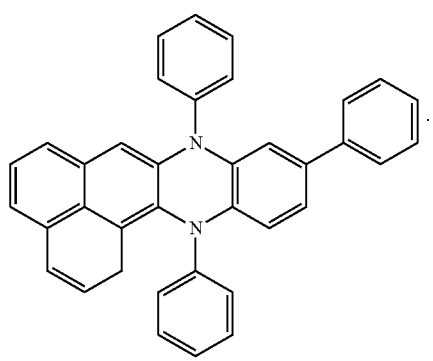

The bipolar host material represented by Formula 1 may be represented by the following Formula 5:

[Formula 5]

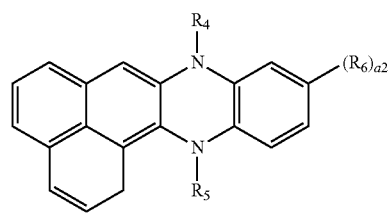

wherein, in Formula 5, a2 may be 0 or 1, and $R_4$ to $R_6$ may each independently be a substituted or unsubstituted aryl group having 6 to 40 ring carbon atoms or a substituted or unsubstituted heteroaryl group having 5 to 40 ring carbon atoms, the substituted groups being substituted with one of the following substituents, in which * represents a bonding location:

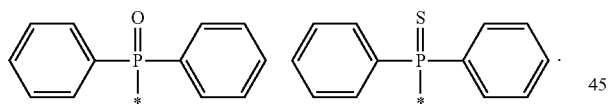

The bipolar host material represented by Formula 1 may be one of the following Compounds E-1 to E-12:

E-1

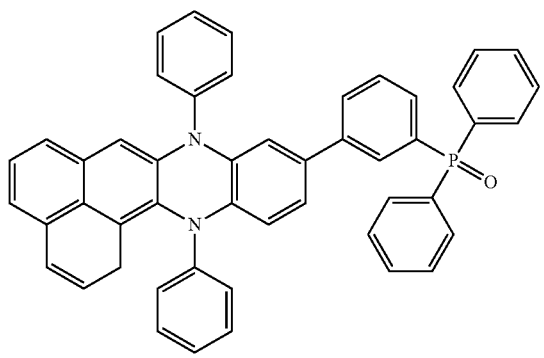

E-2

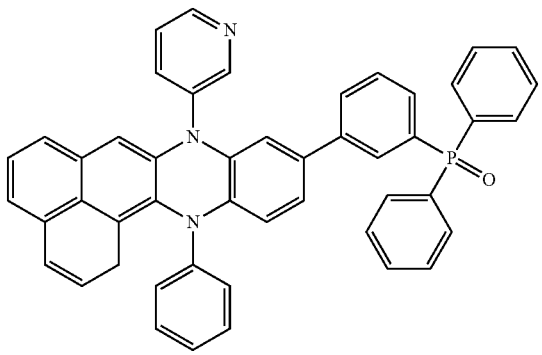

E-3

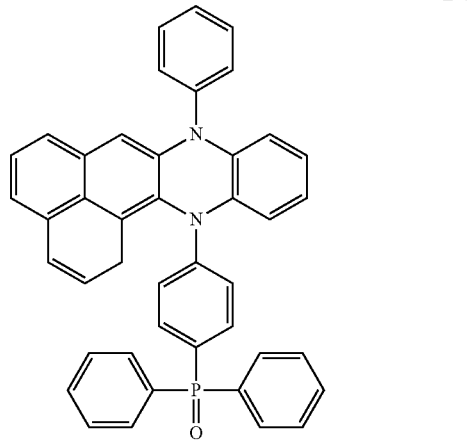

E-4

E-5

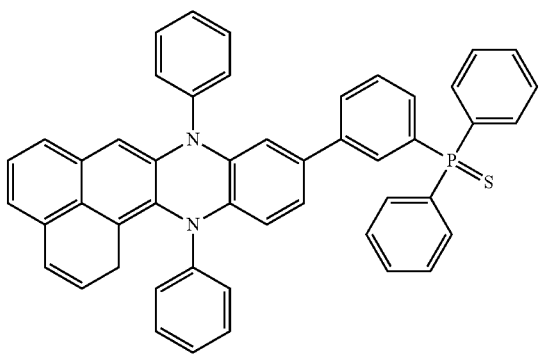

-continued
E-6
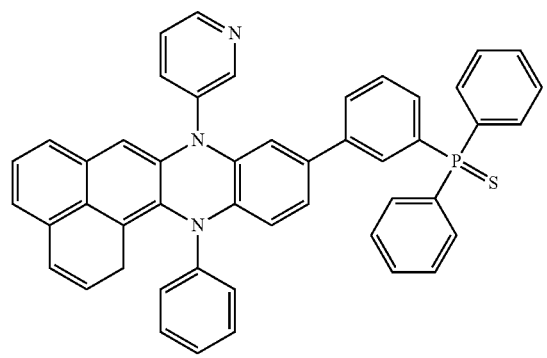
E-7
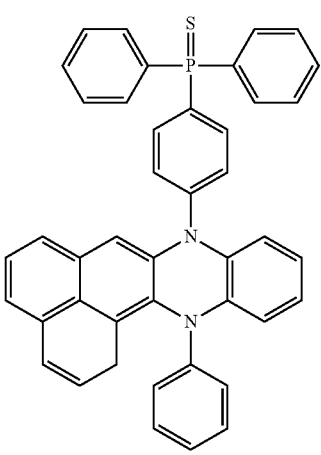
E-8
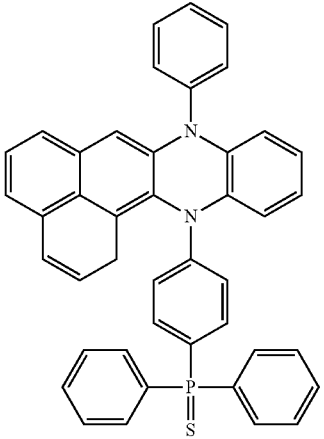
E-9
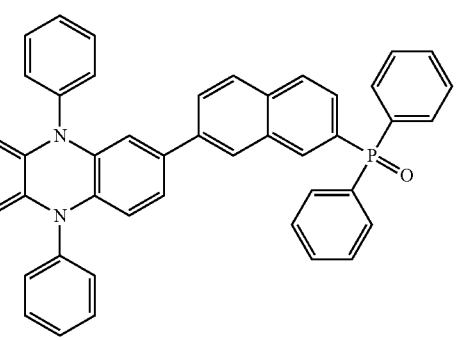
E-10
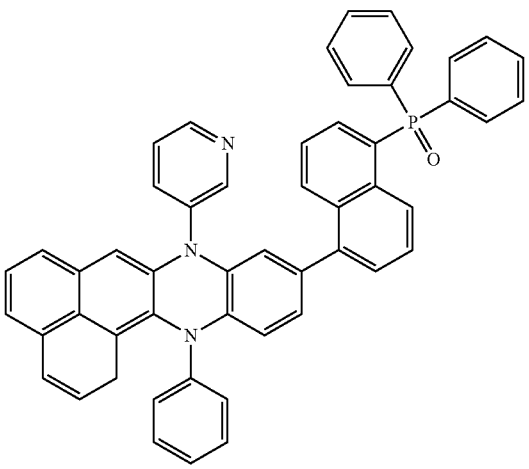
E-11
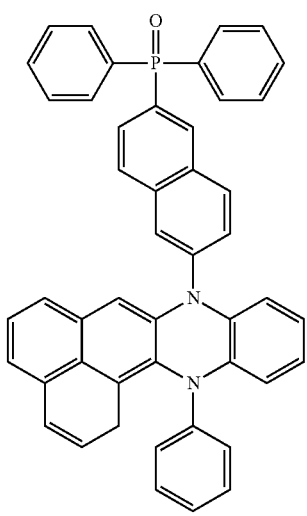
E-12
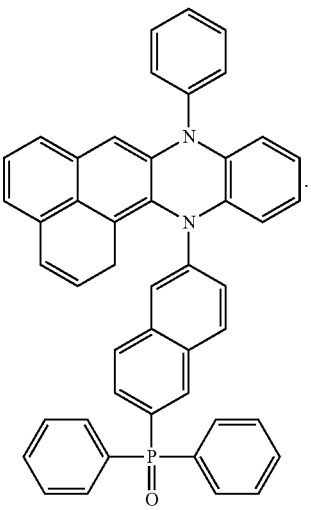

The hole transport host material may be a compound represented by the following Formula 8:

[Formula 8]

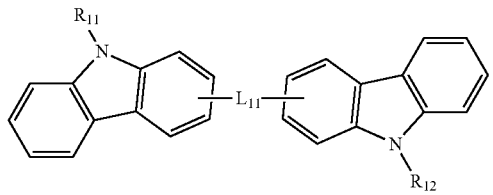

wherein, in Formula 8, $L_{11}$ may be a direct linkage, a substituted or unsubstituted arylene group having 6 to 18 ring carbon atoms, or a substituted or unsubstituted heteroarylene group having 5 to 15 ring carbon atoms, $R_{11}$ and $R_{12}$ may each independently be hydrogen, a halogen atom, an alkyl group having 1 to 20 carbon atoms, a cycloalkyl group having 3 to 40 carbon atoms, a substituted or unsubstituted aryl group having 6 to 50 ring carbon atoms, or a substituted or unsubstituted heteroaryl group having 5 to 50 ring carbon atoms.

The hole transport host material represented by Formula 8 may be one of the following Compounds A-1 to A-16:

A-1

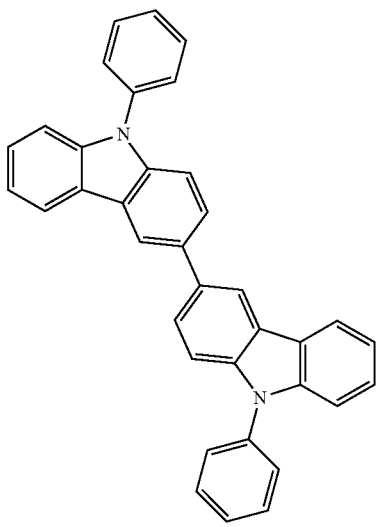

A-2

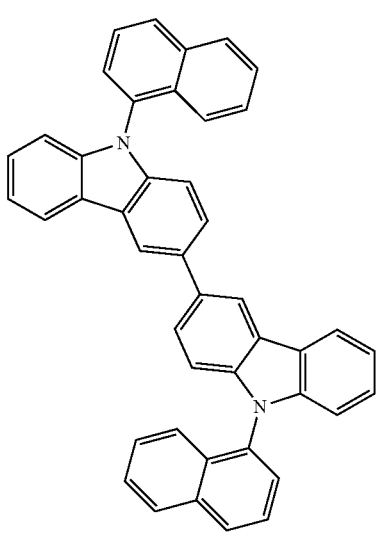

A-3

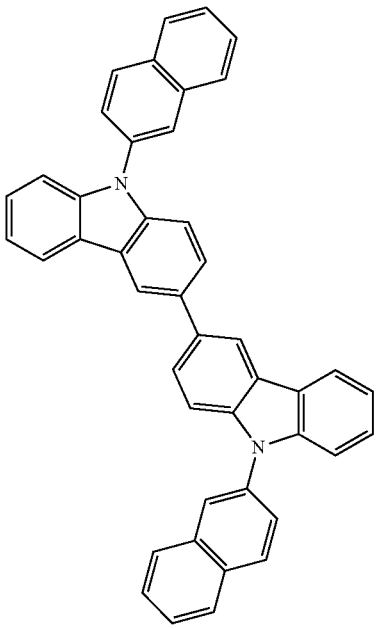

A-4

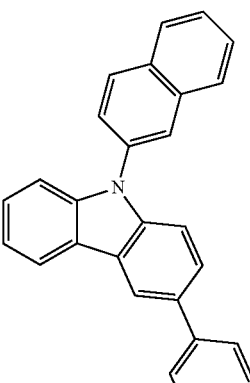
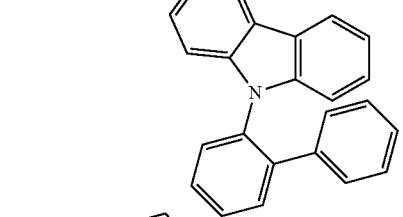

A-5

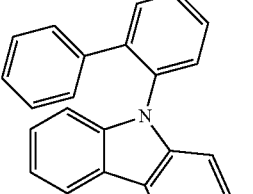
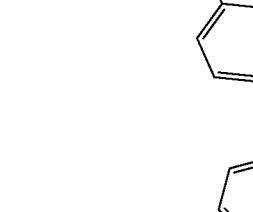

A-6
A-7
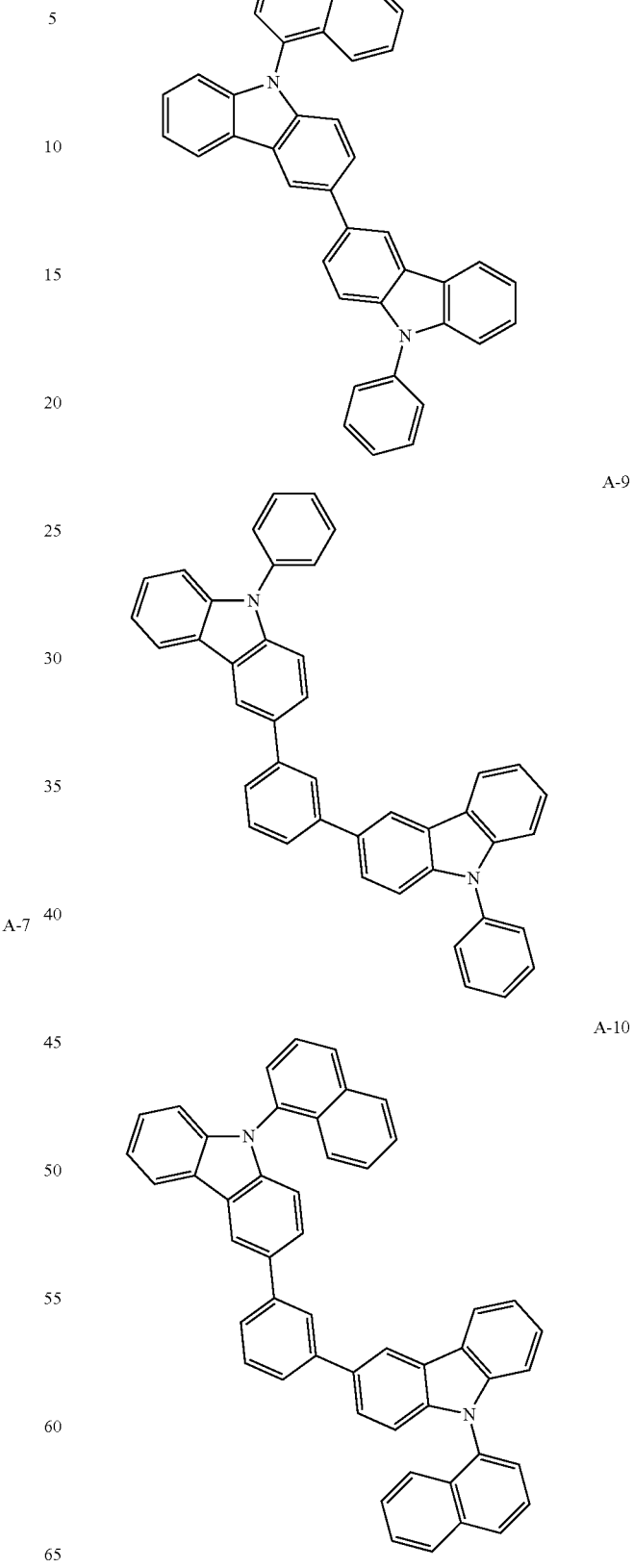
A-8
A-9
A-10

A-11
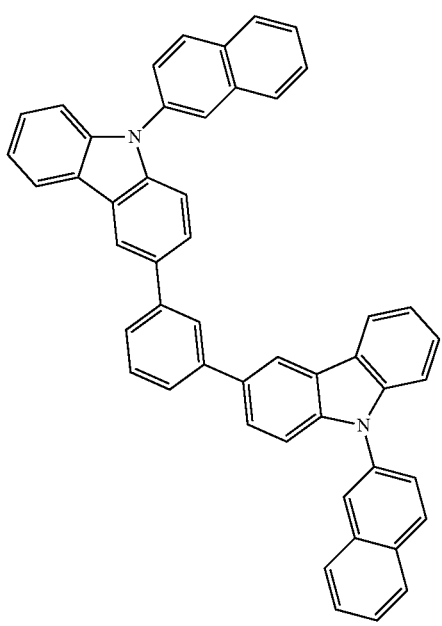
A-13
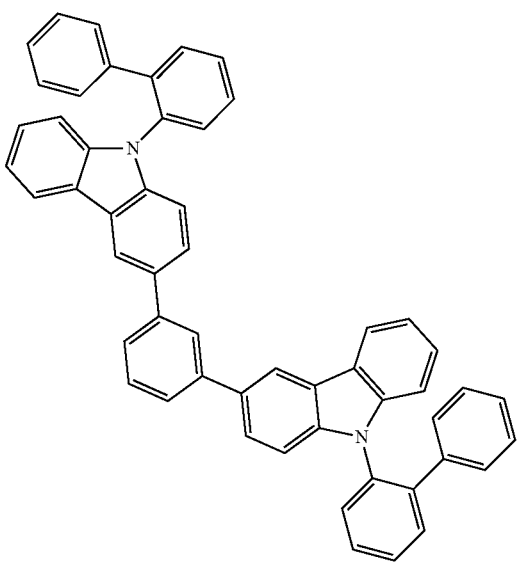
A-12
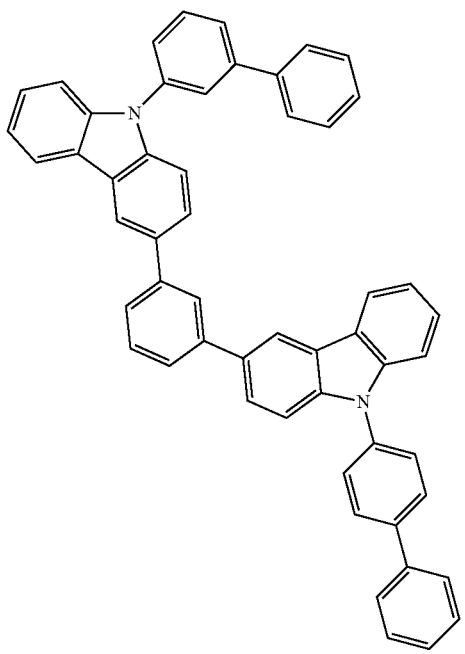
A-14
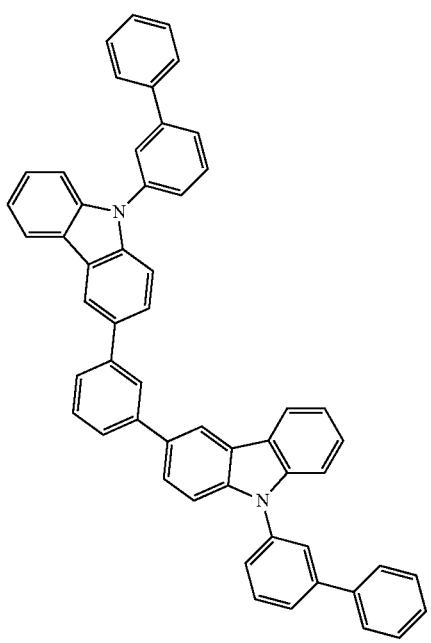

A-15

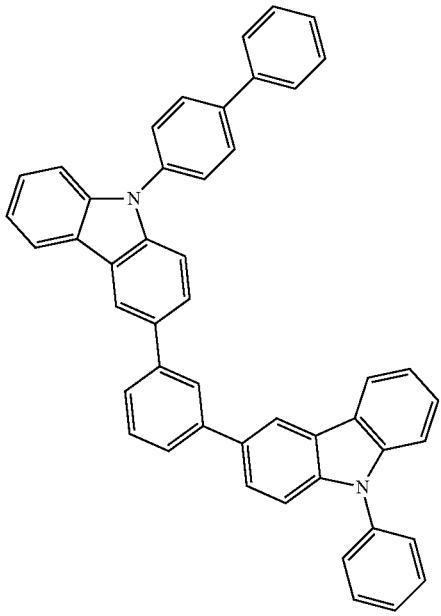

A-16

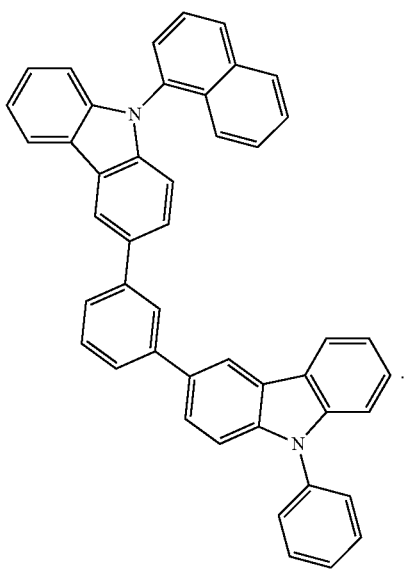

The electron transport host material may be a compound represented by the following Formula 10:

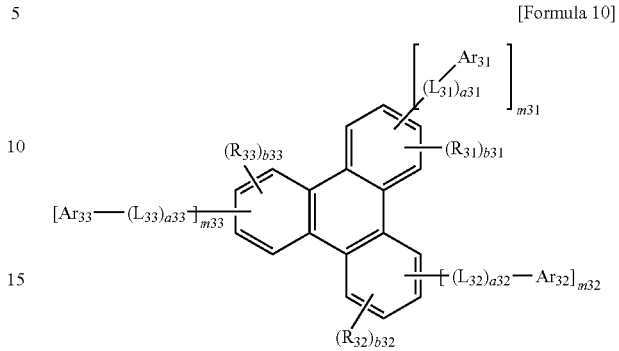

[Formula 10]

wherein, in Formula 10, $L_{31}$ to $L_{33}$ may each independently be selected from a substituted or unsubstituted cycloalkylene group having 3 to 10 carbon atoms, a substituted or unsubstituted heterocycloalkylene group having 1 to 10 carbon atoms, a substituted or unsubstituted cycloalkenylene group having 3 to 10 carbon atoms, a substituted or unsubstituted heterocycloalkenylene group having 1 to 10 carbon atoms, a substituted or unsubstituted arylene group having 6 to 60 ring carbon atoms, a substituted or unsubstituted heteroarylene group having 1 to 60 ring carbon atoms, a substituted or unsubstituted divalent nonaromatic carbocyclic condensed polycyclic group and a substituted or unsubstituted divalent nonaromatic heterocyclic condensed polycyclic group; $Ar_{31}$ to $Ar_{33}$ may each independently be selected from a substituted or unsubstituted aryl group having 6 to 60 ring carbon atoms, a substituted or unsubstituted heteroaryl group having 1 to 60 ring carbon atoms, a substituted or unsubstituted monovalent nonaromatic carbocyclic condensed polycyclic group, and a substituted or unsubstituted monovalent nonaromatic heterocyclic condensed polycyclic group; $R_{31}$ to $R_{33}$ may each independently be hydrogen, deuterium, a halogen atom, a hydroxyl group, a cyano group, a nitro group, an amino group, an amidino group, a hydrazine group, a hydrazone group, a carboxylate or a salt thereof, a sulfonate or a salt thereof, a phosphate or a salt thereof, a substituted or unsubstituted alkyl group having 1 to 60 carbon atoms, a substituted or unsubstituted alkenyl group having 2 to 60 carbon atoms, a substituted or unsubstituted alkynyl group having 2 to 60 carbon atoms, a substituted or unsubstituted alkoxy group having 1 to 60 carbon atoms, a substituted or unsubstituted cycloalkyl group having 3 to 10 carbon atoms, a substituted or unsubstituted heterocycloalkyl group having 1 to 10 carbon atoms, a substituted or unsubstituted cycloalkenyl group having 3 to 10 carbon atoms, a substituted or unsubstituted heterocycloalkenyl group having 1 to 10 carbon atoms, a substituted or unsubstituted aryl group having 6 to 60 ring carbon atoms, a substituted or unsubstituted aryloxy group having 6 to 60 carbon atoms, a substituted or unsubstituted arylthio group having 6 to 60 carbon atoms, a substituted or unsubstituted heteroaryl group having 1 to 60 ring carbon atoms ring, a substituted or unsubstituted monovalent nonaromatic carbocyclic condensed polycyclic group, or a substituted or unsubstituted monovalent nonaromatic heterocyclic condensed polycyclic group; a31, a32, a33, and b31 may each independently be an integer of 0 to 3; b32, b33, m32, and m33 may each independently be an integer of 0 to 4; and m31 may be an integer of 1 to 4.

In Formula 10, m31 may be 1, m32 may be 0, and m33 may be 0.

In Formula 10, $R_{31}$ to $R_{33}$ may each independently be selected from hydrogen, deuterium, a halogen atom, a methyl group, an ethyl group, an n-propyl group, an iso-propyl group, an n-butyl group, an iso-butyl group, a sec-butyl group, a tort-butyl group, a phenyl group, a naphthyl group, a pyridyl group, a pyrimidyl group, a pyrazinyl group, a fluorenyl group, and a carbazole group.

The electron transport host material represented by Formula 10 may be one of the following Compounds B-1 to B-20:

B-1
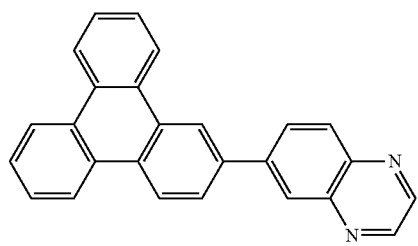

B-2
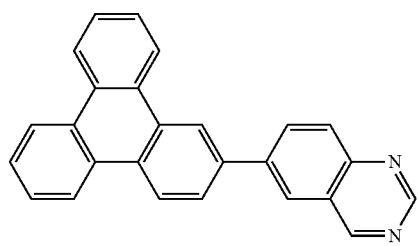

B-3
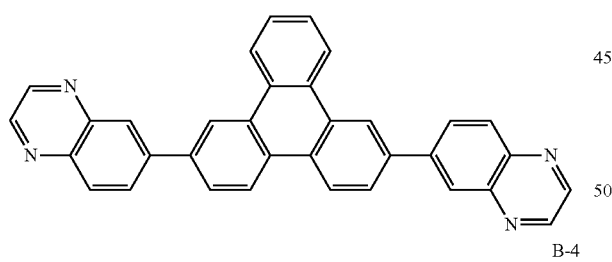

B-4
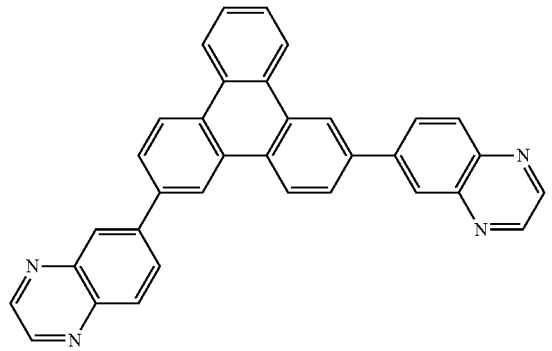

B-5
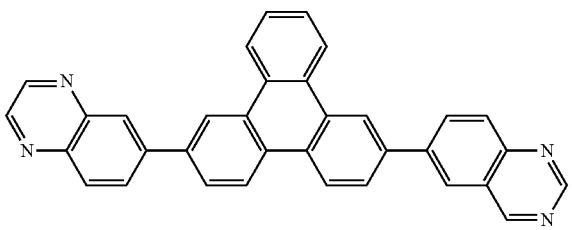

B-6
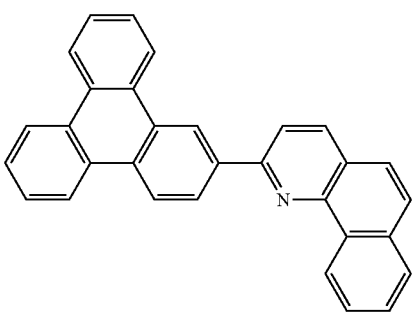

B-7
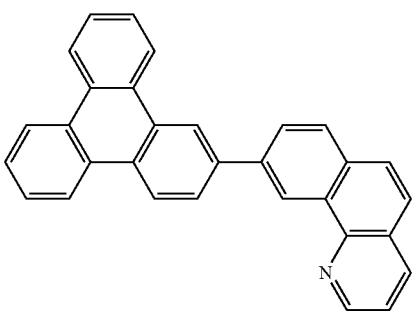

B-8
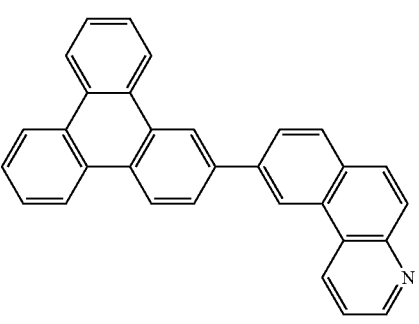

B-9
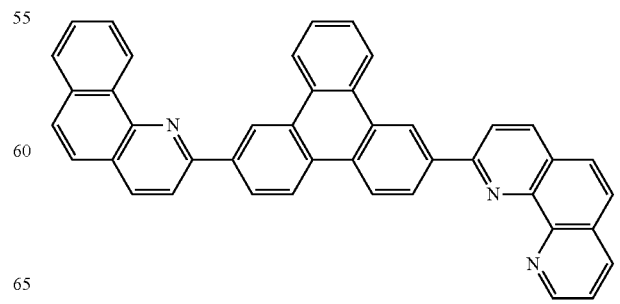

B-10

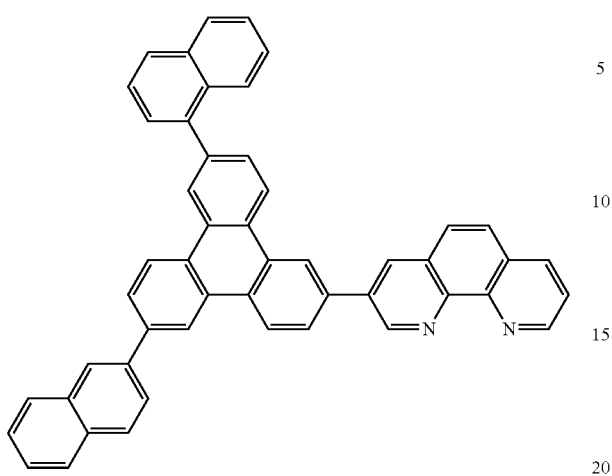

B-11

B-12

B-13

B-14

B-15

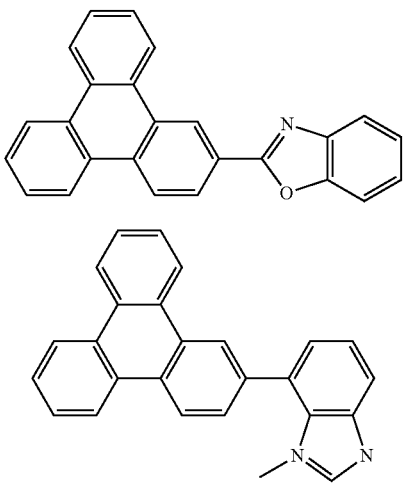

B-16

B-17

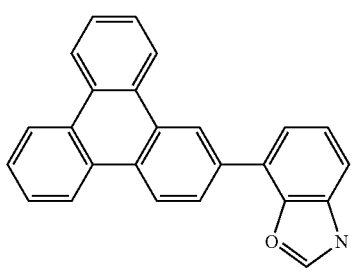

B-18

B-19

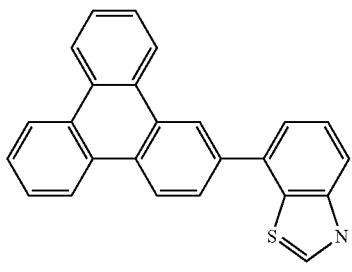

B-20

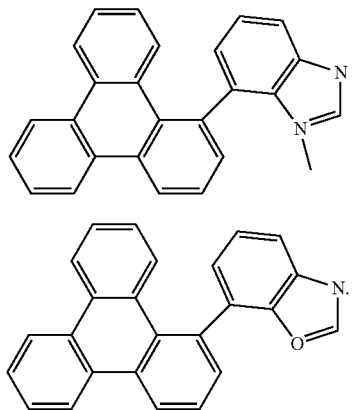

The hole controlling layer may include a hole injection layer adjacent to the first electrode, and a hole transport layer adjacent to the emission layer.

The electron controlling layer may include an electron transport layer adjacent to the emission layer, and an electron injection layer adjacent to the second electrode.

The embodiments may be realized by providing a display device comprising a plurality of pixels, wherein at last one pixel of the plurality of pixels includes a first electrode; a hole controlling layer on the first electrode; an emission layer on the hole controlling layer; an electron controlling layer on the emission layer; and a second electrode on the electron controlling layer, wherein the emission layer includes a hole transport host material, an electron transport host material, a bipolar host material, and at least one dopant material.

The bipolar host material may be a compound represented by the following Formula 1:

[Formula 1]

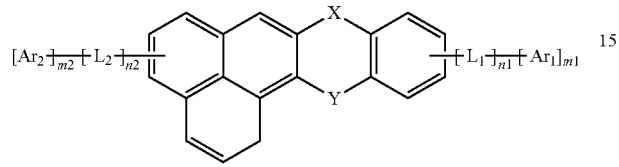

wherein, in Formula 1, X and Y may each independently be one of NR, S, O or Si, R may be a substituted or unsubstituted aryl group having 6 to 40 ring carbon atoms or a substituted or unsubstituted heteroaryl group having 5 to 40 ring carbon atoms, $L_1$ and $L_2$ are each independently selected from hydrogen, deuterium, a halogen atom, an amino group, a nitro group, a nitrile group, an alkyl group having 1 to 40 carbon atoms, an alkenyl group having 2 to 40 carbon atoms, an alkynyl group having 2 to 40 carbon atoms, an aryl group having 5 to 40 ring carbon atoms, a heteroaryl group having 1 to 40 ring carbon atoms, an alkoxy group having 1 to 40 carbon atoms, an aryloxy group having 5 to 40 carbon atoms, an alkylamino group having 1 to 40 carbon atoms, an arylamino group having 5 to 40 carbon atoms, a diarylamino group having 5 to 40 carbon atoms, a heteroarylamino group having 5 to 40 carbon atoms, a diheteroarylamino group having 2 to 40 carbon atoms, an arylakyl group having 6 to 40 carbon atoms, a heteroarylalkyl group having 6 to 40 carbon atoms, a cycloalkyl group having 3 to 40 carbon atoms, a halogenalkyl group having 1 to 40 carbon atoms, a heterocycloalkyl group having 3 to 40 carbon atoms, an alkylsilyl group having 3 to 40 carbon atoms, an arylsilyl group having 3 to 40 carbon atoms, and a heteroarylsilyl group having 3 to 40 carbon atoms, $Ar_1$ and $Ar_2$ may each independently be selected from a substituted or unsubstituted aryl group having 5 to 60 ring carbon atoms, a substituted or unsubstituted heteroaryl group having 3 to 60 ring carbon atoms, and a substituted or unsubstituted condensed polycyclic group having 6 to 60 ring carbon atoms, and n1, n2, m1 and m2 may each independently be 0 or 1.

The bipolar host material represented by Formula 1 may be one of the following Compounds H-1 to H-9:

H-1

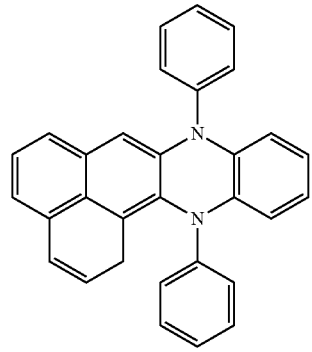

H-2

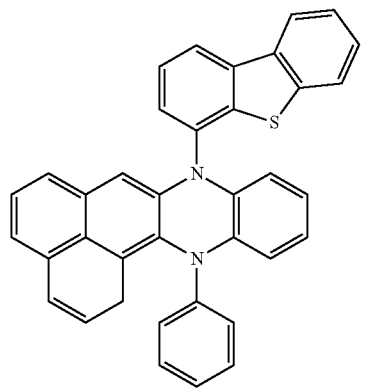

H-3

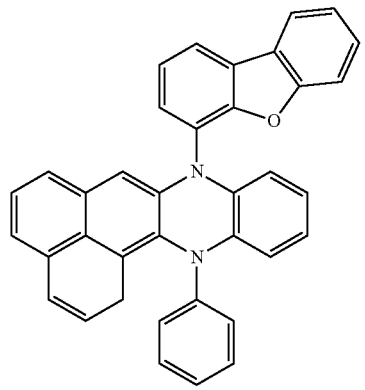

H-4

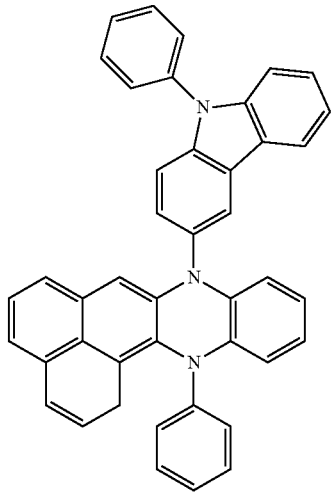

H-5
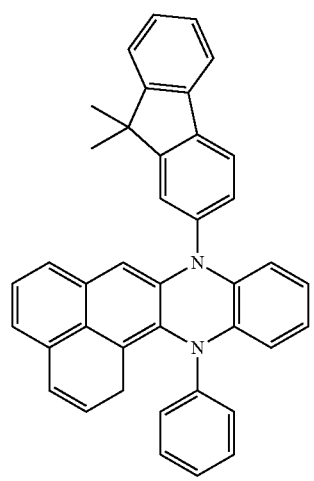
H-6
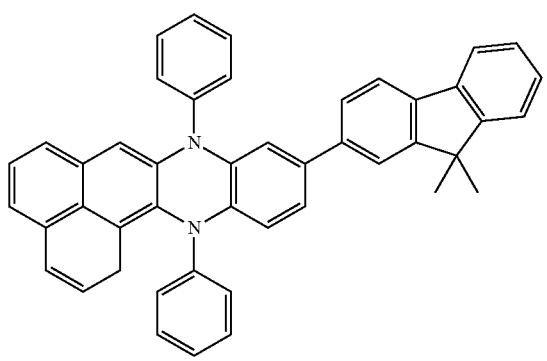
H-7
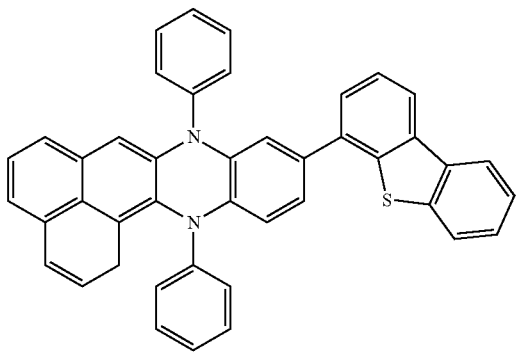
H-8
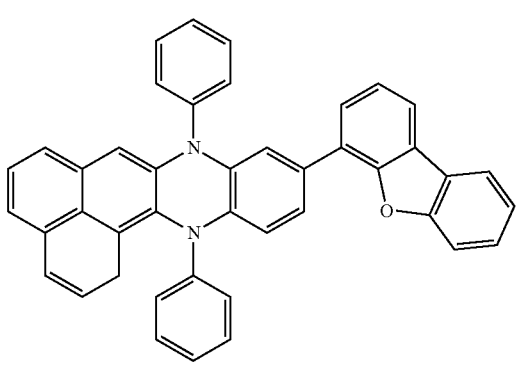
H-9
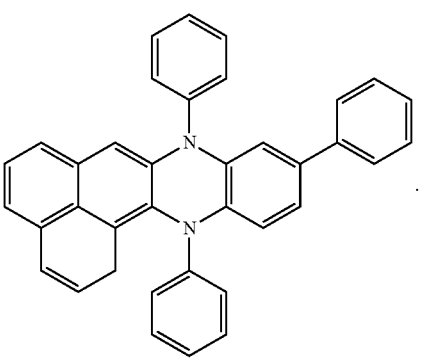
The bipolar host material represented by Formula 1 may be one of the following Compounds E-1 to E-12:
E-1
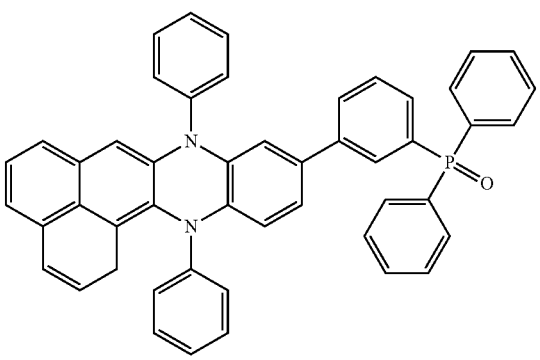
E-2
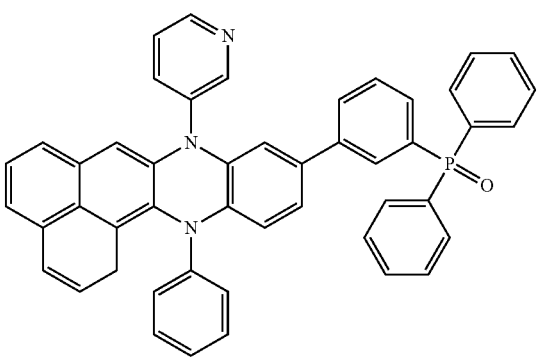

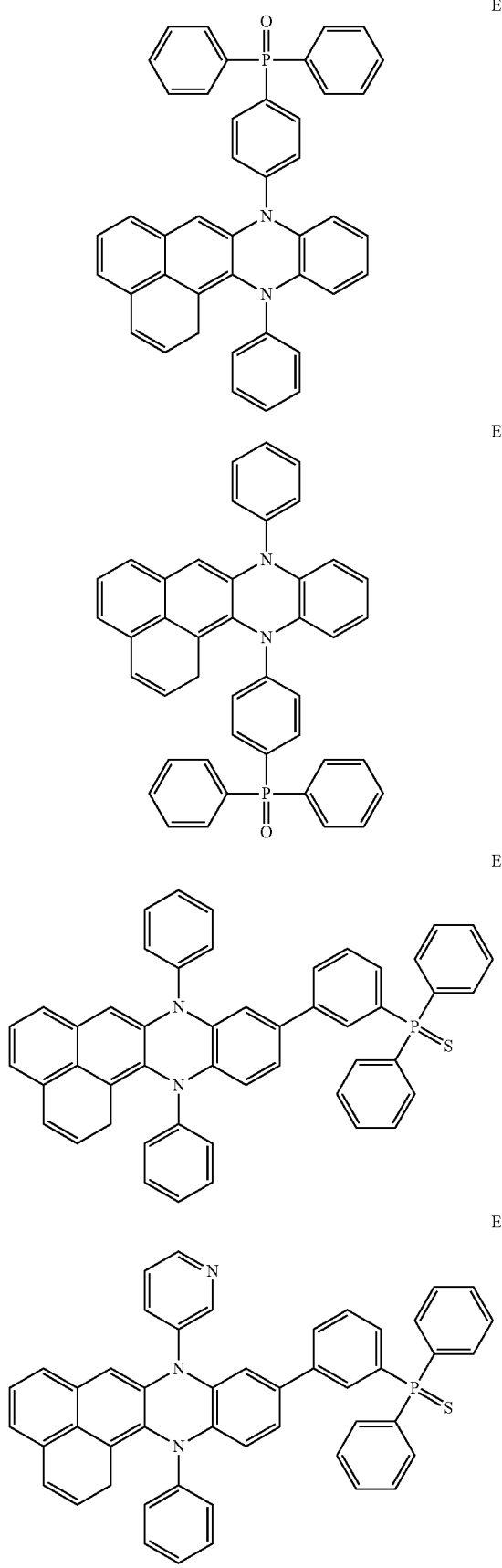
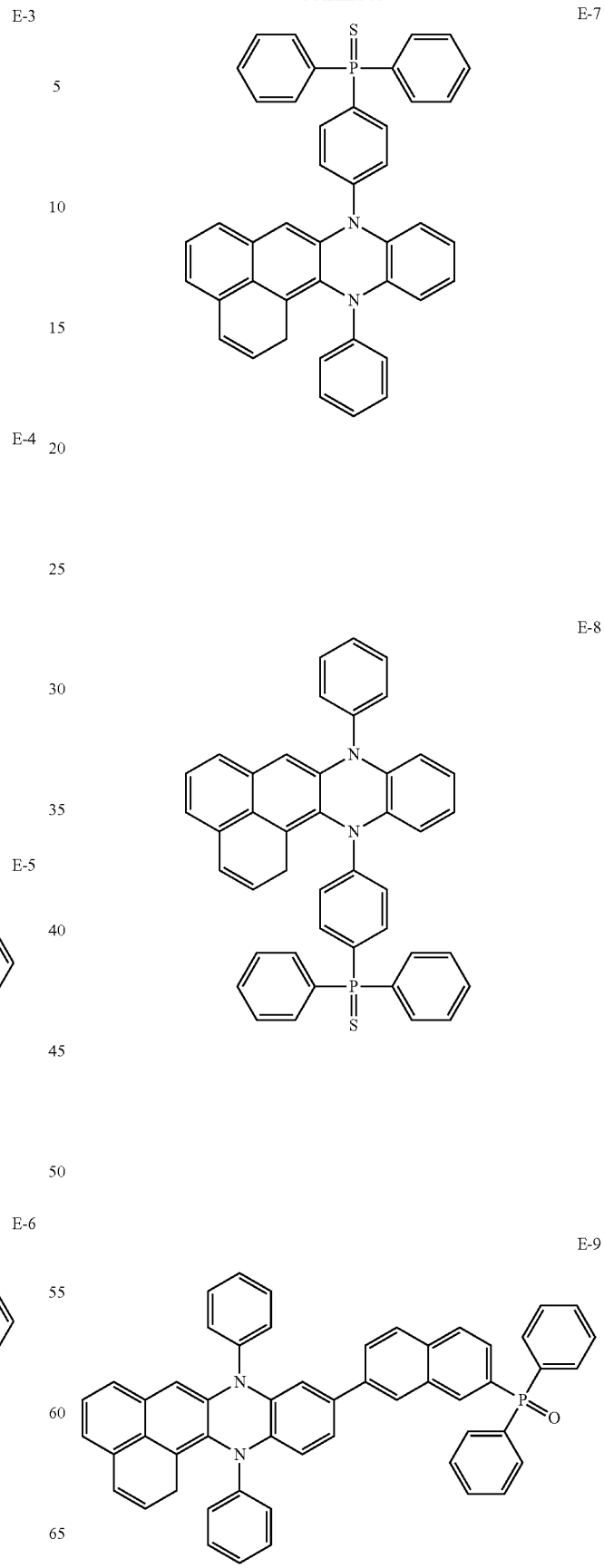

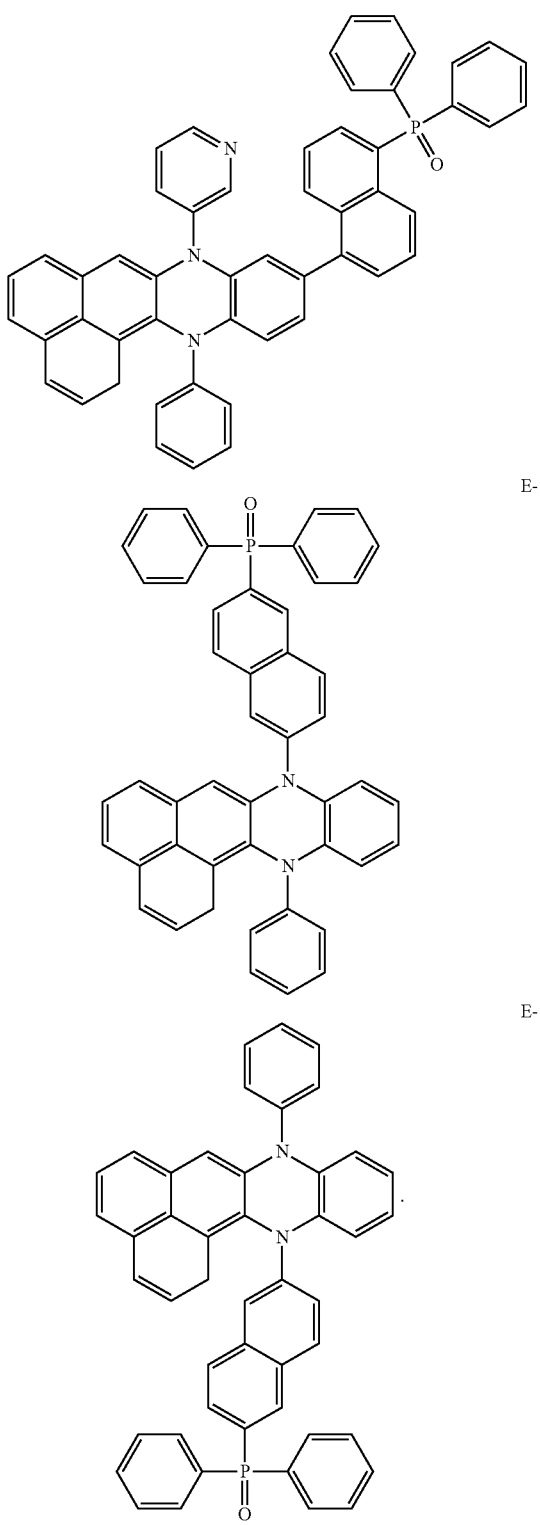

E-10

E-11

E-12

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
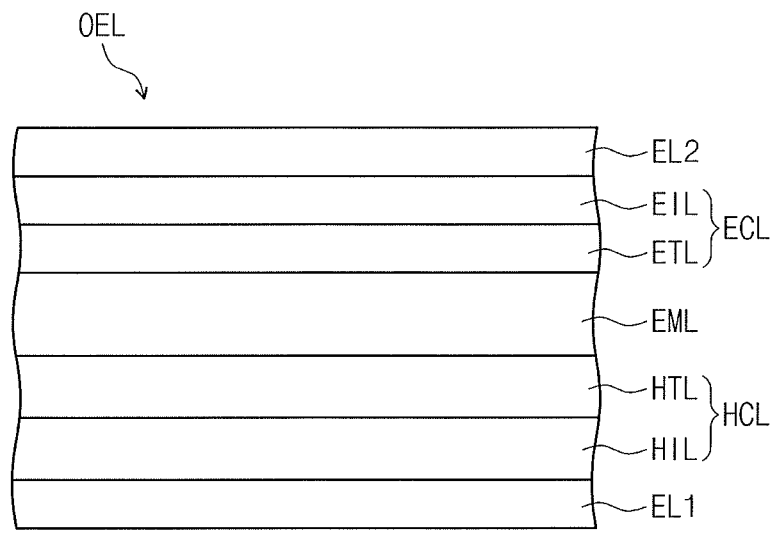
FIG. 1 illustrates a cross-sectional view of an organic light emitting device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

Like reference numerals refer to like elements throughout. In the drawings, the dimensions of structures are exaggerated for clarity of illustration. It will be understood that, although the terms first, second, etc. may be used herein to describe various elements, these elements should not be limited by these terms. These terms are only used to distinguish one element from another element. Thus, a first element could be termed a second element without departing from the teachings herein. Similarly, a second element could be termed a first element. As used herein, the singular forms are intended to include the plural forms as well, unless the context clearly indicates otherwise.

It will be further understood that the terms "comprises", "includes," "including," and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof. It will also be understood that when a layer, a film, a region, a plate, etc. is referred to as being 'on' another part, it can be directly on the other part, or intervening layers may also be present. On the contrary, it will be understood that when a layer, a film, a region, a plate, etc. is referred to as being 'under' another part, it can be directly under, and one or more intervening layers may also be present.

In addition, it will also be understood that when a layer is referred to as being "between" two layers, it can be the only layer between the two layers, or one or more intervening layers may also be present.

Meanwhile, -* or

in the formulae means a connecting part or bonding location in a compound.

Hereinafter, the organic light emitting device will be explained in detail with reference to the accompanying drawings.

FIG. 1 illustrates a cross-sectional view of an organic light emitting device according to an embodiment. The organic light emitting device according to an embodiment may be a lamination type light emitting device manufactured by laminating elements one by one. Referring to FIG. 1, an organic light emitting device may include a first electrode EL1, a hole controlling layer HCL, an emission layer EML, an electron controlling layer ECL and a second electrode EL2.

The first electrode EL1 is conductive. The first electrode EL1 may be a pixel electrode or an anode. The first electrode EL1 may be a transmissive electrode, a transflective electrode, or a reflective electrode. In the case where the first electrode EL1 is the transmissive electrode, the first electrode EL1 may be formed using, e.g., indium tin oxide (ITO), indium zinc oxide (IZO), zinc oxide (ZnO), indium tin zinc oxide (ITZO), etc. When the first electrode EL1 is the transflective electrode or the reflective electrode, the first electrode EL1 may include Ag, Mg, Al, Pt, Pd, Au, Ni, Nd, Ir, Cr, or a mixture of metals.

In an implementation, the first electrode EL1 or the second electrode EL2 may include a plurality of layers. The first electrode EL1 or the second electrode EL2 may be provided using a sputtering method or a vacuum deposition method.

On the first electrode EL1, an organic layer may be disposed. The organic layer may include an emission layer EML. In an implementation, the organic layer may further include a hole controlling layer HCL and an electron controlling layer ECL.

The hole controlling layer HCL may be provided on the first electrode EL1. In an implementation, the hole controlling layer HCL may include a hole injection layer HIL or a hole transport layer HTL, and may further include at least one of a buffer layer or an electron blocking layer.

In an implementation, the hole controlling layer HCL may have a single layer formed using a single material, a single layer formed using a plurality of different materials, or a multilayer structure including a plurality of layers formed using a plurality of different materials.

For example, the hole controlling layer HCL may have a structure of a single layer formed using a plurality of different materials, or a structure laminated from the first electrode EL1 of hole injection layer HIL/hole transport layer HTL, hole injection layer HIL/hole transport layer HTL/buffer layer, hole injection layer HIL/buffer layer, hole transport layer HTL/buffer layer, or hole injection layer HIL/hole transport layer HTL/electron blocking layer.

In an implementation, the hole controlling layer HCL may be formed using various methods such as a vacuum deposition method, a spin coating method, a cast method, a Langmuir-Blodgett (LB) method, an inkjet printing method, a laser printing method, and a laser induced thermal imaging (LITI) method.

When the hole controlling layer HCL includes the hole injection layer HIL, the hole controlling layer HCL may include, e.g., a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), etc.

When the hole controlling layer HCL includes the hole transport layer HTL, the hole controlling layer HCL may include, e.g., a carbazole derivative such as N-phenylcarbazole and polyvinyl carbazole, a fluorine-based derivative, N,N'-bis(3-methylphenyl)-N,N'-diphenyl-[1,1-biphenyl]-4,4'-diamine (TPD), a triphenylamine-based derivative such as 4,4',4"-tris(N-carbazolyl)triphenylamine (TCTA), N,N'-di(1-naphthyl)-N,N'-diphenylbenzidine (NPB), 4,4'-cyclohexylidene bis[N,N-bis(4-methylphenyl)benzeneamine] (TAPC), etc.

In an implementation, the thickness of the hole controlling layer HCL may be from about 100 Å to about 10,000 Å, e.g., from about 100 Å to about 1,000 Å. When the hole controlling layer HCL includes both the hole injection layer HIL and the hole transport layer HTL, the thickness of the hole injection layer HIL may be from about 100 Å to about 10,000 Å, e.g., from about 100 Å to about 1,000 Å, and the thickness of the hole transport layer HTL may be from about 50 Å to about 2,000 Å, e.g., from about 100 Å to about 1,500 Å. When the thicknesses of the hole controlling layer HCL, the hole injection layer HIL, and the hole transport layer HTL satisfy the above-described ranges, satisfactory hole transport properties may be obtained without substantial increase of a driving voltage.

In an implementation, the hole controlling layer HCL may further include a charge generating material other than the above-described materials to help improve conductivity. The charge generating material may be dispersed in the hole controlling layer HCL uniformly or non-uniformly. The charge generating material may be, e.g., a p-dopant. In an implementation, the p-dopant may be one of, e.g., a quinone derivative, a metal oxide, or a cyano group-containing compound. Examples of the p-dopant may include a quinone derivative such as tetracyanoquinodimethane (TCNQ), and 2,3,5,6-tetrafluoro-tetracyanoquinodimethane (F4-TCNQ), or a metal oxide such as tungsten oxide, and molybdenum oxide.

As described above, the hole controlling layer HCL may further include at least one of the buffer layer or the electron blocking layer other than the hole injection layer HIL and the hole transport layer HTL. The buffer layer may help compensate an optical resonance distance according to the wavelength of light emitted from the emission layer EML and increase light emission efficiency. Materials included in the hole controlling layer HCL may be used as materials included in the buffer layer. The electron blocking layer is a layer for helping to prevent electron injection from the electron controlling layer ECL to the hole controlling layer HCL.

The emission layer EML may be provided on the hole controlling layer HCL. The emission layer EML may have a single layer or a multi layer structure including a plurality of layers.

The emission layer EML may be formed using various methods such as a vacuum deposition method, a spin coating method, a cast method, a Langmuir-Blodgett (LB) method, an inkjet printing method, a laser printing method, and a laser induced thermal imaging (LITI) method.

In an organic light emitting device according to an embodiment, the emission layer EML may include three kinds of host materials. In an embodiment shown in FIG. 1, the emission layer in the organic light emitting device may include a hole transport host material, an electron transport host material, and a bipolar host material. In an implementation, the emission layer may include at least one dopant material.

In an implementation, the bipolar host material may be a host material represented by the following Formula 1.

[Formula 1]

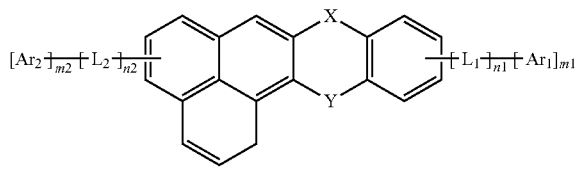

In Formula 1, X and Y may each independently be, e.g., one of NR, S, O or Si. In this case, R may be or may include, e.g., a substituted or unsubstituted aryl group having 6 to 40 ring carbon atoms or a substituted or unsubstituted heteroaryl group having 5 to 40 ring carbon atoms.

$L_1$ and $L_2$ may each independently be selected from or include, e.g., hydrogen, deuterium, a halogen atom, an amino group, a nitro group, a nitrile group, an alkyl group having 1 to 40 carbon atoms, an alkenyl group having 2 to 40 carbon atoms, an alkynyl group having 2 to 40 carbon atoms, an aryl group having 5 to 40 ring carbon atoms, a heteroaryl group having 1 to 40 ring carbon atoms, an alkoxy group having 1 to 40 carbon atoms, an aryloxy group having 5 to 40 carbon atoms, an alkylamino group having 1 to 40 carbon atoms, an arylamino group having 5 to 40 carbon atoms, a diarylamino group having 5 to 40 carbon atoms, a heteroarylamino group having 5 to 40 carbon atoms, a diheteroarylamino group having 2 to 40 carbon atoms, an arylalkyl group having 6 to 40 carbon atoms, a heteroarylalkyl group having 6 to 40 carbon atoms, a cycloalkyl group having 3 to 40 carbon atoms, a halogenalkyl group having 1 to 40 carbon atoms, a heterocycloalkyl group having 3 to 40 carbon atoms, an alkylsilyl group having 3 to 40 carbon atoms, an arylsilyl group having 3 to 40 carbon atoms, and a heteroarylsilyl group having 3 to 40 carbon atoms.

$Ar_1$ and $Ar_2$ may each independently be selected from or include, e.g., a substituted or unsubstituted aryl group having 5 to 60 ring carbon atoms, a substituted or unsubstituted heteroaryl group having 3 to 60 ring carbon atoms, and a substituted or unsubstituted condensed polycyclic group having 6 to 60 ring carbon atoms.

Meanwhile, in the instant description, the terms "substituted or unsubstituted" corresponds to an unsubstituted group or one substituted with or including at least one substituent selected from deuterium, a halogen group, a nitrile group, a nitro group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, a heteroarylamine group, an arylamine group, and a heterocyclic group, or corresponds to a substituent obtained by connecting at least two substituents of the above-described substituents. For example, the substituent obtained by connecting at least two substituents may be a biphenyl group. For example, the biphenyl group may be an aryl group or may be interpreted as a substituent obtained by connecting two phenyl groups.

For example, in $Ar_1$ and $Ar_2$, the substituent of the aryl group, the heteroaryl group and the condensed polycyclic group may be selected from an alkyl group having 1 to 40 carbon atoms, an alkenyl group having 2 to 40 carbon atoms, an alkynyl group having 2 to 40 carbon atoms, an aryl group having 5 to 40 ring carbon atoms, a heteroaryl group having 1 to 40 ring carbon atoms, an alkoxy group having 1 to 40 carbon atoms, an aryloxy group having 5 to 40 carbon atoms, an alkylamino group having 1 to 40 carbon atoms, an arylamino group having 5 to 40 carbon atoms, a diarylamino group having 5 to 40 carbon atoms, a heteroarylamino group having 5 to 40 carbon atoms, a diheteroarylamino group having 2 to 40 carbon atoms, an arylalkyl group having 6 to 40 carbon atoms, a heteroarylalkyl group having 6 to 40 carbon atoms, a cycloalkyl group having 3 to 40 carbon atoms, a halogenalkyl group having 1 to 40 carbon atoms, a heterocycloalkyl group having 3 to 40 carbon atoms, an alkylsilyl group having 3 to 40 carbon atoms, an arylsilyl group having 3 to 40 carbon atoms, and a heteroarylsilyl group having 3 to 40 carbon atoms.

In Formula 1, n1, n2, m1 and m2 may each independently be 0 or 1.

The bipolar host material represented by Formula 1 may exhibit both hole transport properties and electron transport properties. In an implementation, the bipolar host material may exhibit selectively and dominantly the hole transport property or the electron transport property according to the substituent selected.

In an implementation, the bipolar host material may be a compound represented by the following Formula 2.

[Formula 2]

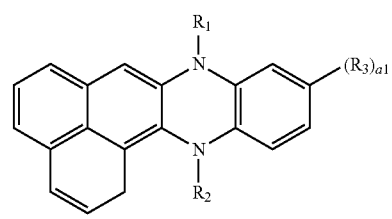

In Formula 2, $R_1$ to $R_3$ may each independently be or include, e.g., a substituted or unsubstituted aryl group having 5 to 40 ring carbon atoms or a substituted or unsubstituted heteroaryl group having 5 to 40 ring carbon atoms. a1 may be 0 or 1. In an implementation, in $R_1$ to $R_3$, the heteroaryl group may each independently include one heteroatom selected from N, S or O.

In an implementation, at least one of $R_1$ to $R_3$ may each independently be one of the following groups.

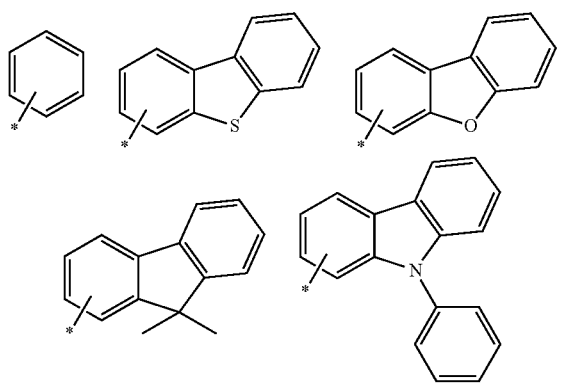

In an implementation, the combination position of bonding location of $R_1$ to $R_3$ may be as follows.

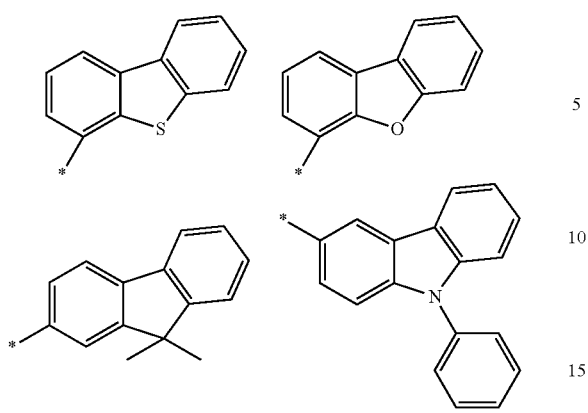
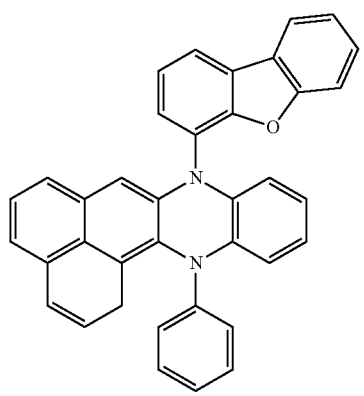
The bipolar material represented by Formula 2 may be a host material having superior hole transport properties relative to the electron transport properties. In an implementation, the bipolar host material represented by Formula 2 may include one of the following Compounds H-1 to H-9.
H-1
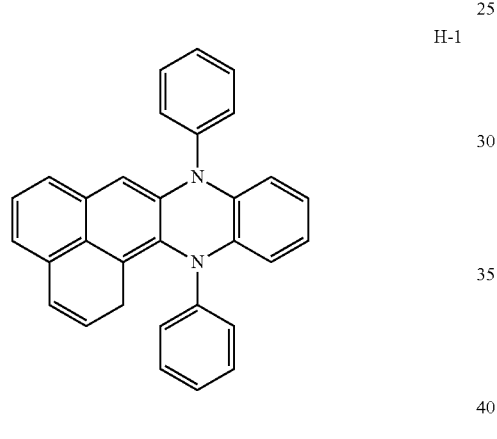
H-4
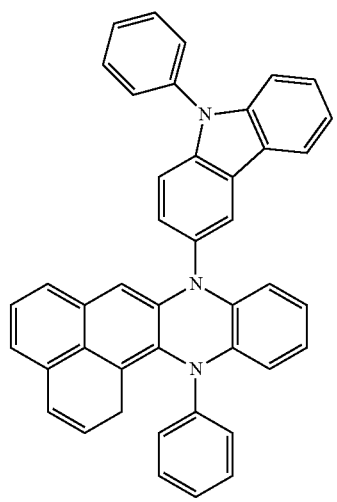
H-2
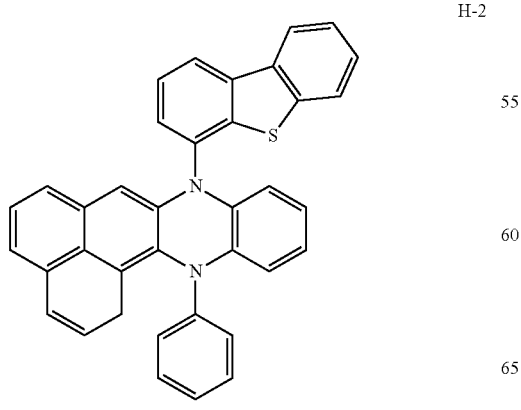
H-5
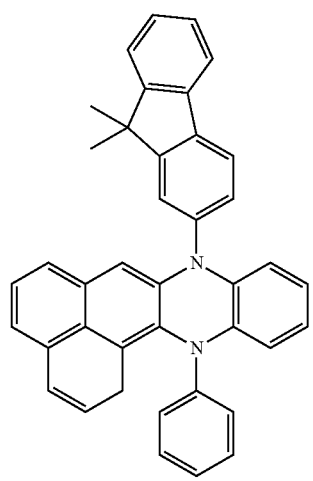

H-6

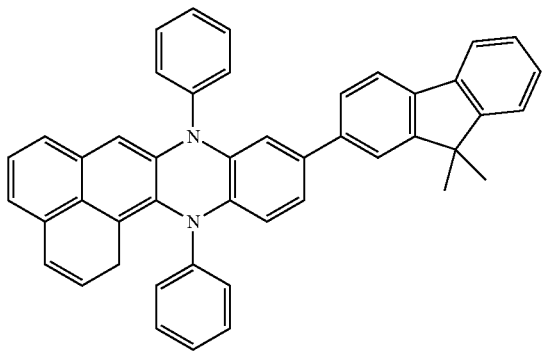

H-7

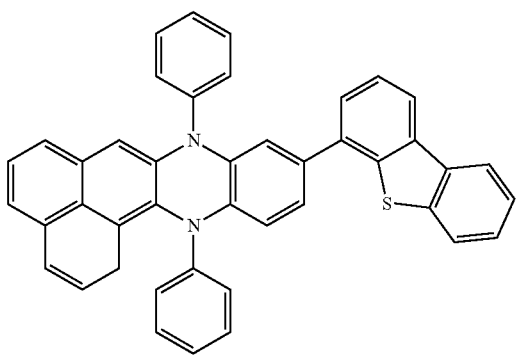

H-8

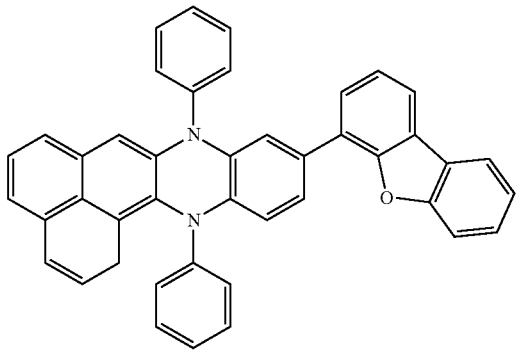

H-9

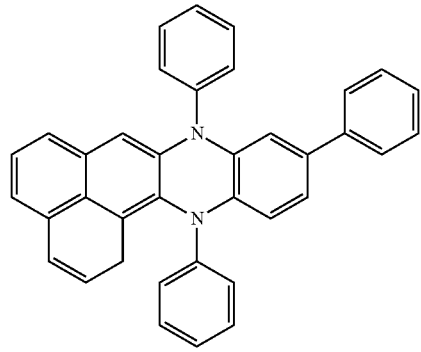

In an implementation, the bipolar host material may be a compound represented by the following Formula 5.

[Formula 5]

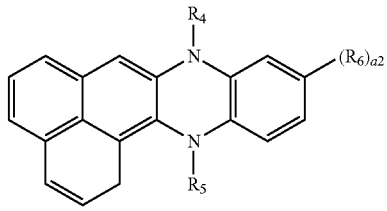

In Formula 5, $R_4$ to $R_6$ may each independently be or include, e.g., a substituted or unsubstituted aryl group having 6 to 40 ring carbon atoms or a substituted or unsubstituted heteroaryl group having 5 to 40 ring carbon atoms. In an implementation, in the substituted heteroaryl group of $R_4$ to $R_6$, the substituted groups may be substituted with one of the following substituents.

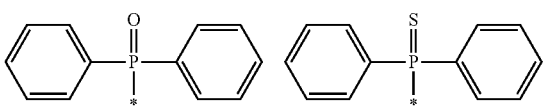

In Formula 5, a2 may be 0 or 1.

The bipolar material represented by Formula 5 may be a host material having superior electron transport properties relative to the hole transport properties. In an implementation, the bipolar host material represented by Formula 5 may include one of the following Compounds E-1 to E-12.

E-1

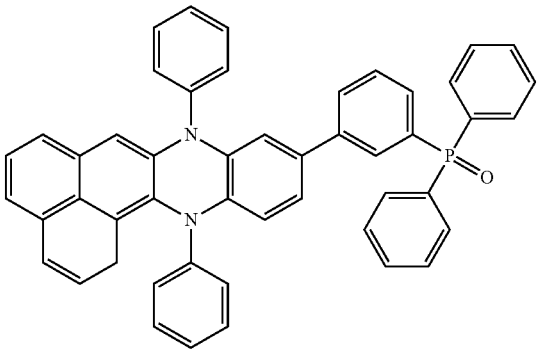

E-2

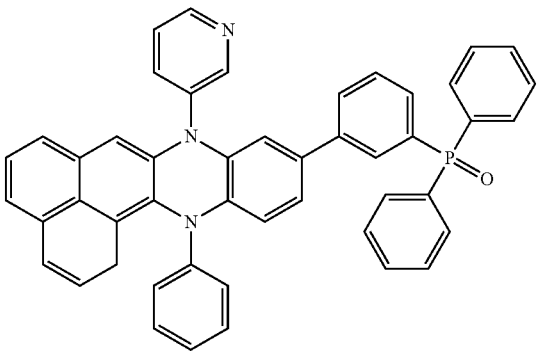

-continued
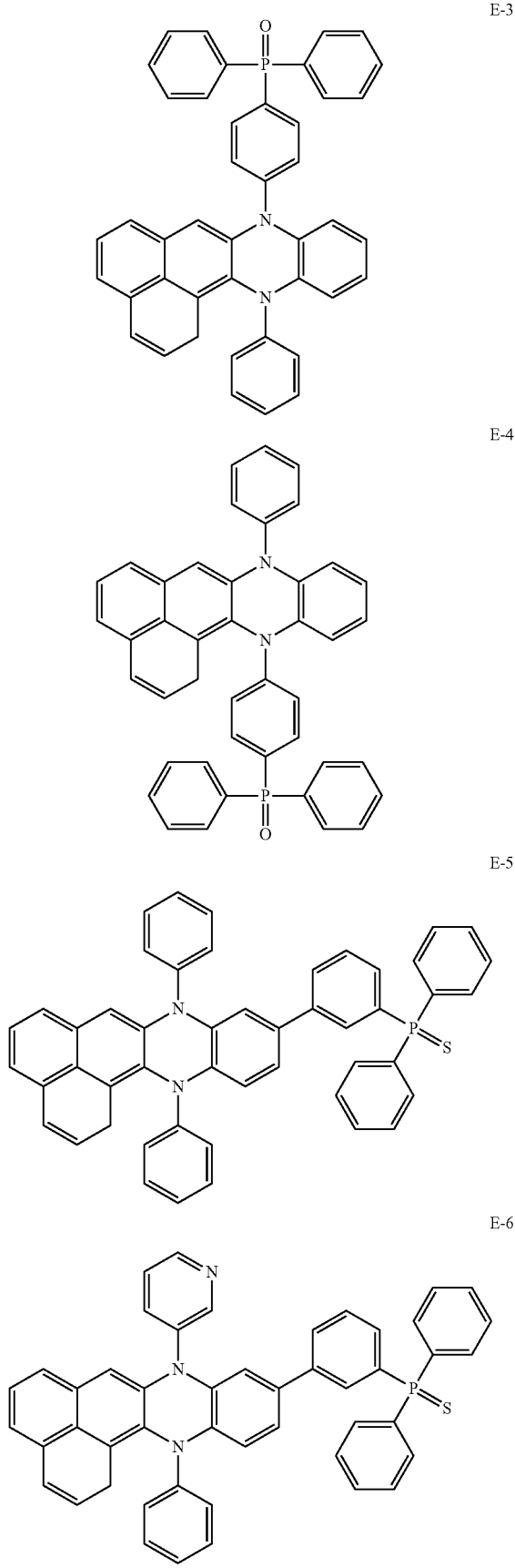
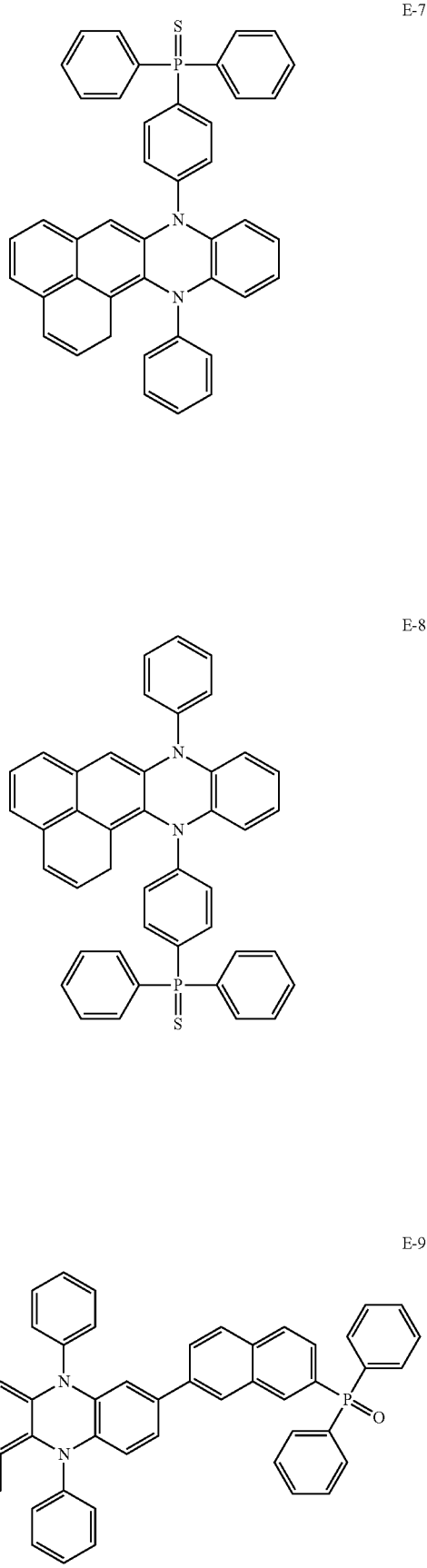

E-10

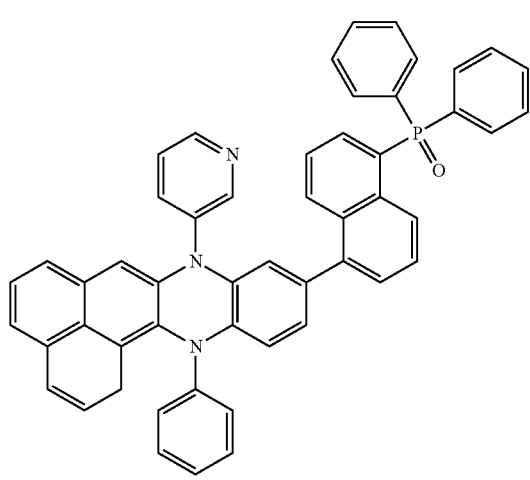

E-12

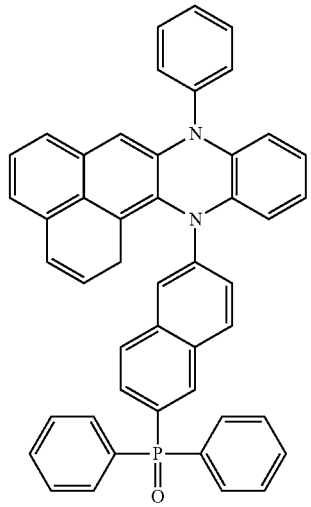

In an implementation, in the organic light emitting device according to an embodiment, the emission layer may include a hole transport host material represented by the following Formula 8.

[Formula 8]

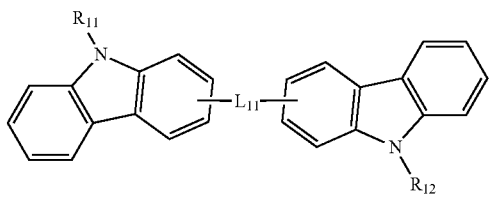

In Formula 8, $L_{11}$ may be or may include, e.g., a direct linkage, a substituted or unsubstituted arylene group having 6 to 18 ring carbon atoms or a substituted or unsubstituted heteroarylene group having 5 to 15 ring carbon atoms. $R_{11}$ and $R_{12}$ may each independently be or include, e.g., hydrogen, a halogen atom, an alkyl group having 1 to 20 carbon atoms, a cycloalkyl group having 3 to 40 carbon atoms, a substituted or unsubstituted aryl group having 6 to 50 ring carbon atoms, or a substituted or unsubstituted heteroaryl group having 5 to 50 ring carbon atoms. In an implementation, the halogen atom may be one of F, Cl, Br, or I.

The hole transport host material represented by Formula 8 may be a carbazole compound, e.g., a carbazole moiety-containing compounds. In an implementation, the carbazole hole transport host represented by Formula 8 may be included in the emission layer to help increase the life of the organic light emitting device. In an implementation, the hole transport host material may include one of the following Compounds A-1 to A-16.

E-11

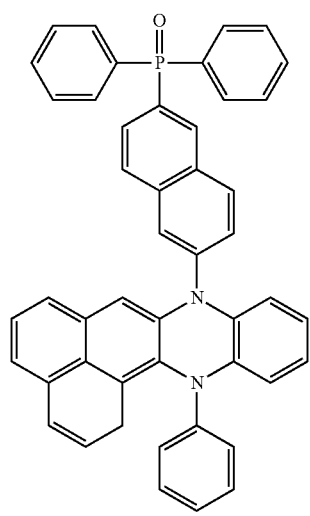

A-1
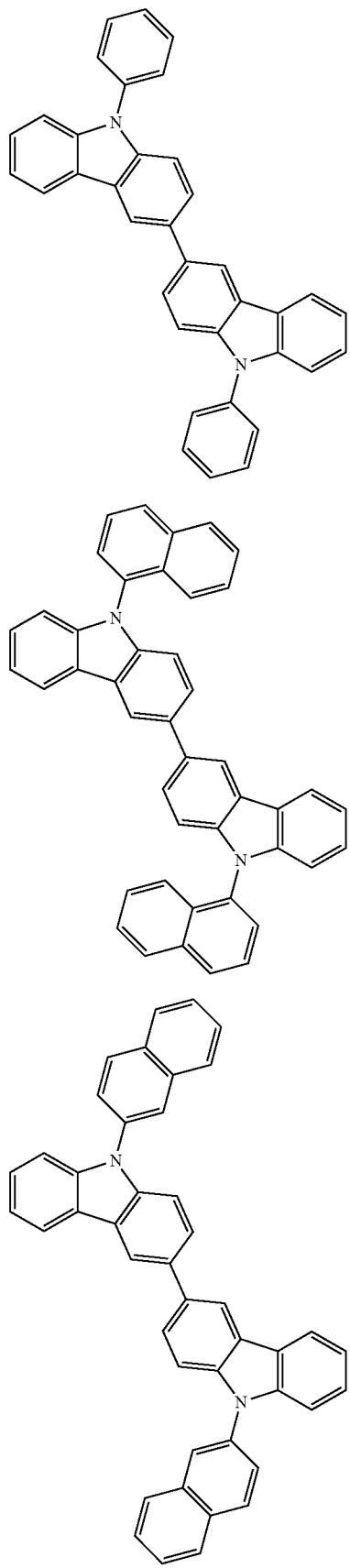
A-2
A-3
-continued
A-4
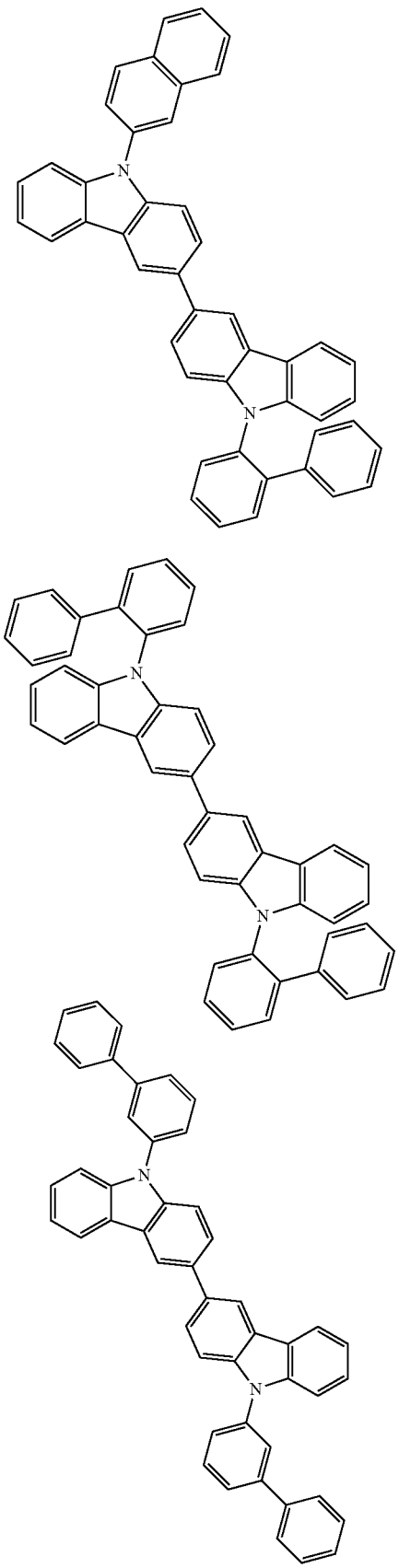
A-5
A-6

-continued
A-7
A-9
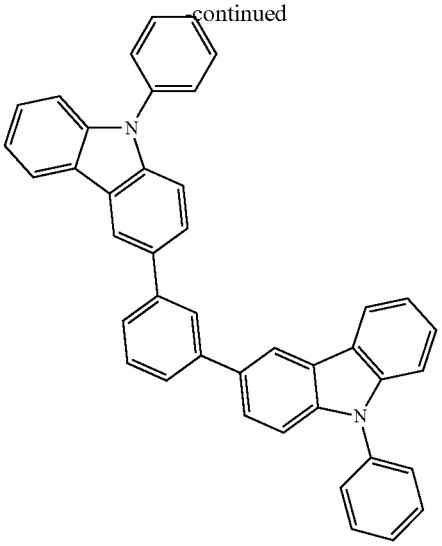
A-10
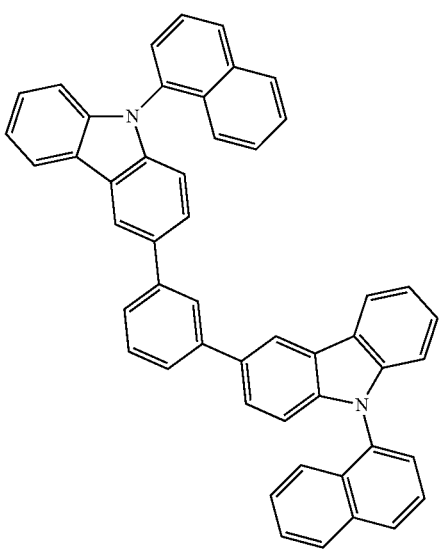
A-8
A-11
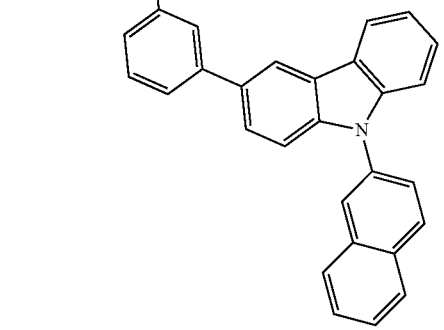

A-12
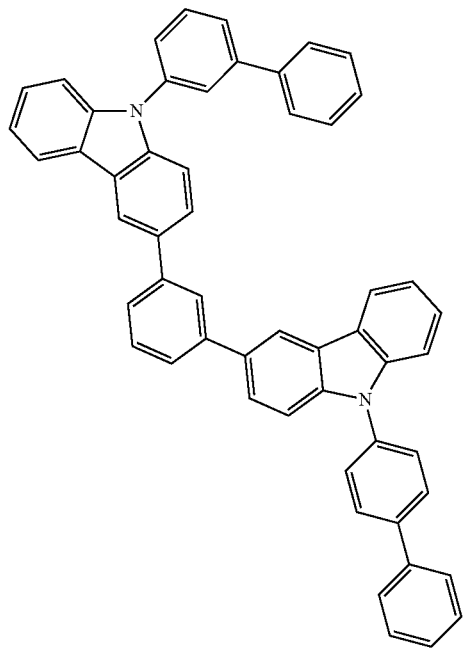
A-14
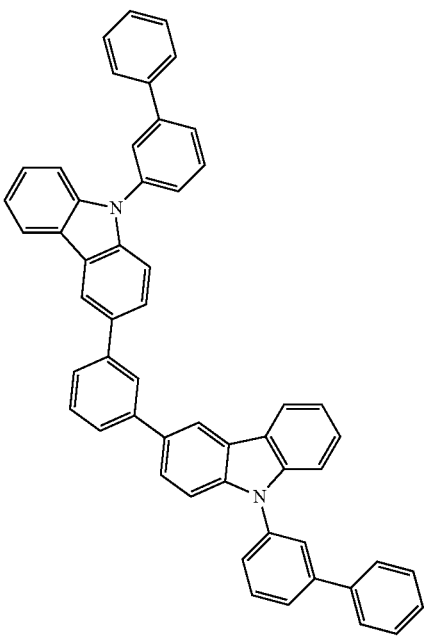
A-13
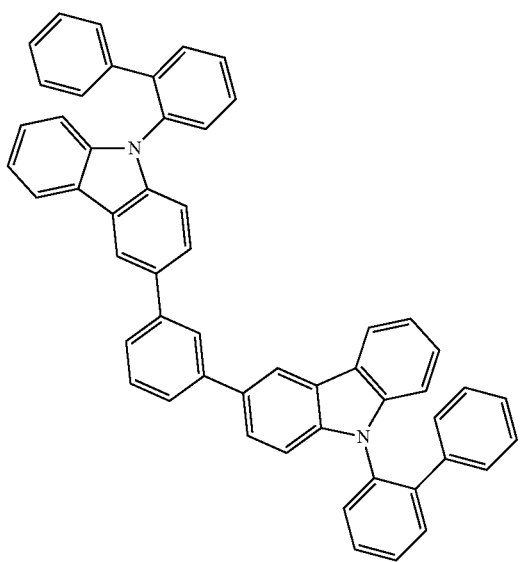
A-15
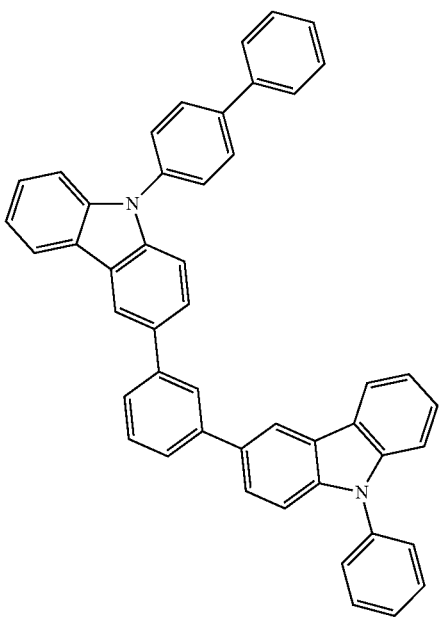

-continued

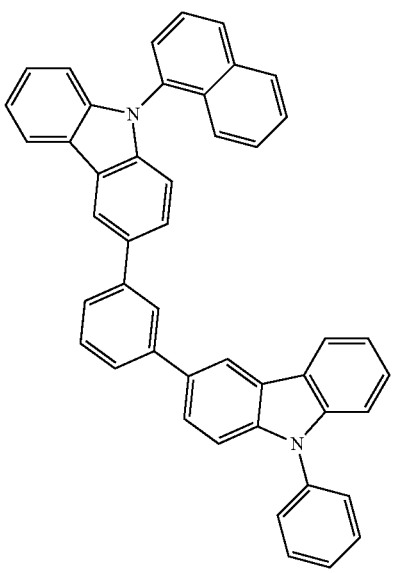

A-16

In an implementation, the electron transport host material included in the emission layer may be represented by the following Formula 10.

[Formula 10]

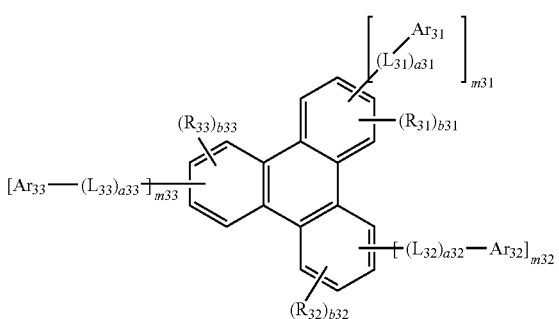

$L_{31}$ to $L_{33}$ may each independently be selected from or include, e.g., a substituted or unsubstituted cycloalkylene group having 3 to 10 carbon atoms, a substituted or unsubstituted heterocycloalkylene group having 1 to 10 carbon atoms, a substituted or unsubstituted cycloalkenylene group having 3 to 10 carbon atoms, a substituted or unsubstituted heterocycloalkenylene group having 1 to 10 carbon atoms, a substituted or unsubstituted arylene group having 6 to 60 ring carbon atoms, a substituted or unsubstituted heteroarylene group having 1 to 60 ring carbon atoms, a substituted or unsubstituted divalent nonaromatic carbocyclic condensed polycyclic group and a substituted or unsubstituted divalent nonaromatic heterocyclic condensed polycyclic group.

$Ar_{31}$ to $Ar_{33}$ may each independently be selected from or include, e.g., a substituted or unsubstituted aryl group having 6 to 60 ring carbon atoms, a substituted or unsubstituted heteroaryl group having 1 to 60 ring carbon atoms, a substituted or unsubstituted monovalent nonaromatic carbocyclic condensed polycyclic group, and a substituted or unsubstituted monovalent nonaromatic heterocyclic condensed polycyclic group.

$R_{31}$ to $R_{33}$ may each independently be selected from or include, e.g., hydrogen, deuterium, a halogen atom, a hydroxyl group, a cyano group, a nitro group, an amino group, an amidino group, a hydrazine group, a hydrazone group, a carboxylate or a salt thereof, a sulfonate or a salt thereof, a phosphate or a salt thereof, a substituted or unsubstituted alkyl group having 1 to 60 carbon atoms, a substituted or unsubstituted alkenyl group having 2 to 60 carbon atoms, a substituted or unsubstituted alkynyl group having 2 to 60 carbon atoms, a substituted or unsubstituted alkoxy group having 1 to 60 carbon atoms, a substituted or unsubstituted cycloalkyl group having 3 to 10 carbon atoms, a substituted or unsubstituted heterocycloalkyl group having 1 to 10 carbon atoms, a substituted or unsubstituted cycloalkenyl group having 3 to 10 carbon atoms, a substituted or unsubstituted heterocycloalkenyl group having 1 to 10 carbon atoms, a substituted or unsubstituted aryl group having 6 to 60 ring carbon atoms, a substituted or unsubstituted aryloxy group having 6 to 60 carbon atoms, a substituted or unsubstituted arylthio group having 6 to 60 carbon atoms, a substituted or unsubstituted heteroaryl group having 1 to 60 ring carbon atoms, a substituted or unsubstituted monovalent nonaromatic carbocyclic condensed polycyclic group, and a substituted or unsubstituted monovalent nonaromatic heterocyclic condensed polycyclic group.

a31, a32, a33, and b31 may each independently be an integer of 0 to 3, b32, b33, m32, and m33 may each independently be an integer of 0 to 4, and m31 may be an integer of 1 to 4.

The triphenylene electron transport host material represented by Formula 10 may include one of the following Compounds B-1 to B-20. In an organic light emitting device according to an embodiment, the efficiency of the light emitting device may be improved by including one of Compounds B-1 to B-20 as the electron transport host material.

B-1

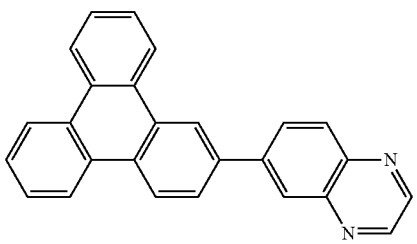

B-2

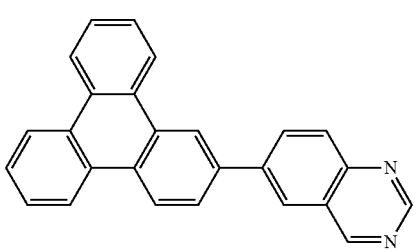

B-3
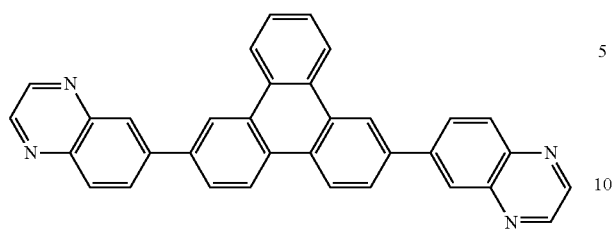
B-4
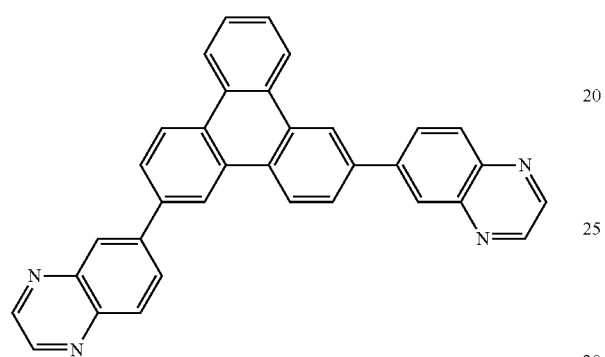
B-5
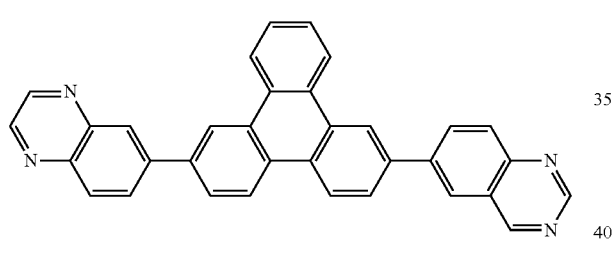
B-6
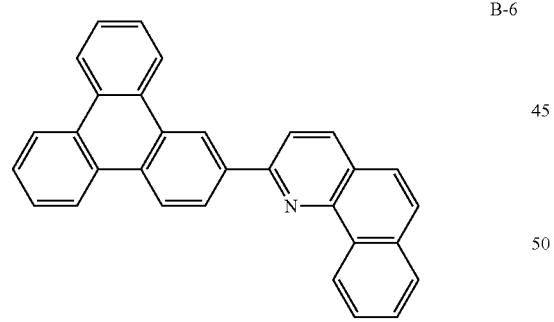
B-7
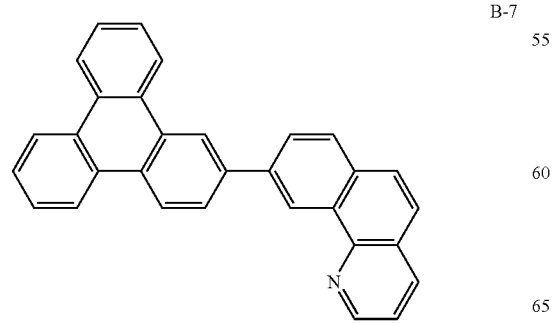
B-8
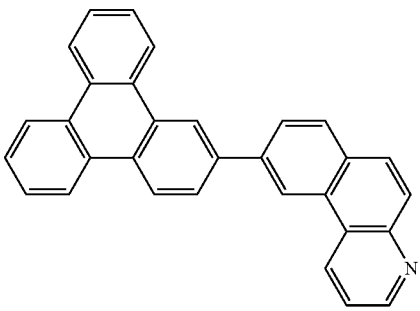
B-9
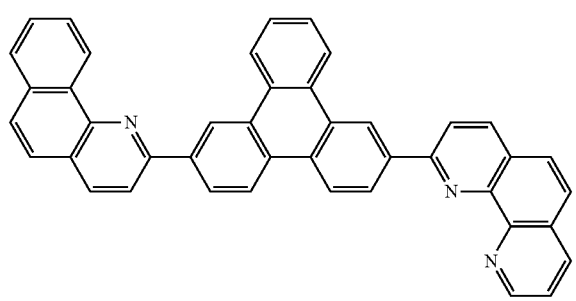
B-10
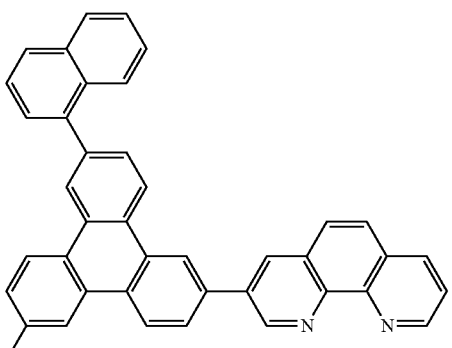
B-11
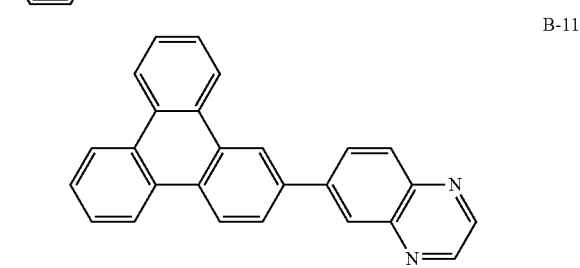
B-12
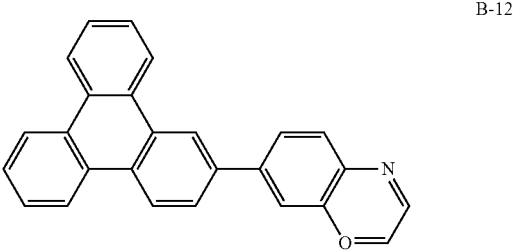

B-13

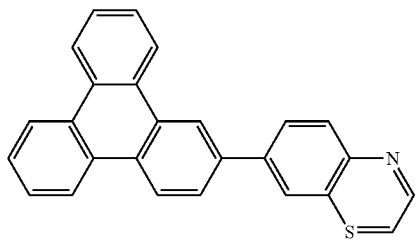

B-14

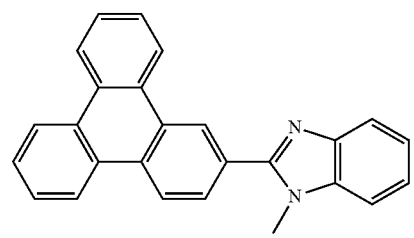

B-15

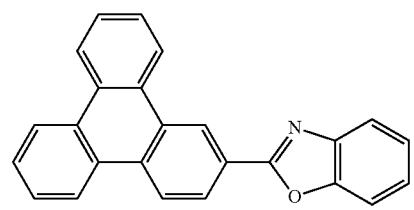

B-16

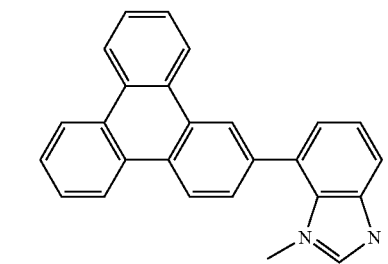

B-17

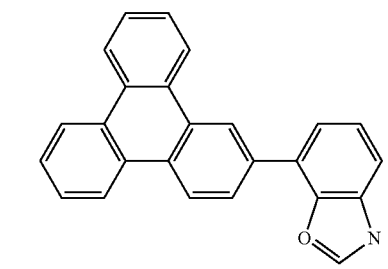

B-18

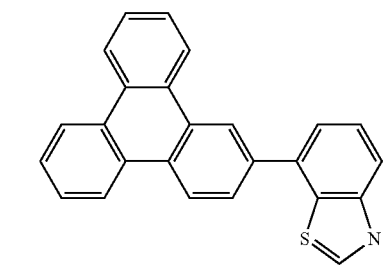

B-19

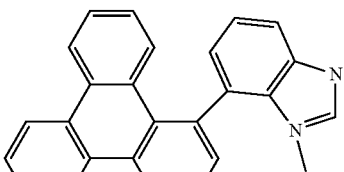

B-20

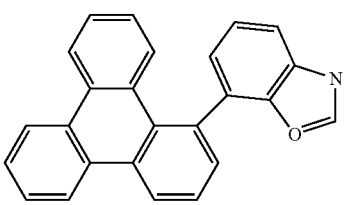

In an implementation, the emission layer may include at least one dopant material together with the three kinds of the host materials. The dopant material may be changed according to the color of light emitted from the emission layer.

When the emission layer EML emits red light, the dopant included in the emission layer EML may be selected from a metal complex or an organometallic complex such as bis(1-phenylisoquinoline)acetylacetonate iridium (PIQIr(acac)), bis(1-phenylquinoline)acetylacetonate iridium (PQIr(acac), tris(1-phenylquinoline)iridium (PQIr), and octaethylporphyrin platinum (PtOEP).

When the emission layer EML emits green light, the dopant included in the emission layer EML may be selected from a metal complex or an organometallic complex such as fac-tris(2-phenylpyridine)iridium (Ir(ppy)3).

When the emission layer EML emits blue light, the dopant included in the emission layer EML may be selected from a metal complex or an organometallic complex such as (4,6-F2ppy)$_2$Irpic.

In an organic light emitting device according to an embodiment, both the life and efficiency of the light emitting device may be improved by including three kinds of different host materials. For example, the organic light emitting device according to an embodiment may include a carbazole hole transport host material that has a lifespan increasing effect, a triphenylene electron transport host material that has an efficiency improving effect, and a bipolar host material that helps compensate the efficiency and life of the device. Therefore, improved emission efficiency and life may be obtained by using three kinds of host materials, when compared to a case using a single host material or a case using two kinds of host materials.

On the emission layer, an electron controlling layer ECL may be provided. The electron controlling layer ECL may include at least one of a hole blocking layer, an electron transport layer ETL and an electron injection layer EIL.

For example, the electron controlling layer ECL may have a structure laminated from the emission layer EML of electron transport layer ETL/electron injection layer EIL, or hole blocking layer/electron transport layer ETL/electron injection layer EIL, or may have a single layer structure obtained by mixing two or more layers thereof.

The electron controlling layer ECL may be formed using various methods such as a vacuum deposition method, a spin coating method, a cast method, a Langmuir-Blodgett (LB) method, an inkjet printing method, a laser printing method, and a laser induced thermal imaging (LITI) method.

When the electron controlling layer ECL includes the electron transport layer ETL, the electron controlling layer ECL may include, e.g., tris(8-hydroxyquinolinato)aluminum (Alq3), 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,08)-(1,1'-biphenyl-4-olato)aluminum (BAlq), berylliumbis(benzoquinolin-10-olate (Bebq2), 9,10-di(naphthalene-2-yl)anthracene (ADN), or a mixture thereof. The thickness of the electron transport layer may be from about 100 Å to about 1,000 Å, e.g., about 150 Å to about 500 Å. If the thickness of the electron transport layer ETL satisfies the above-described range, satisfactory electron transport property may be obtained without substantial increase of a driving voltage.

When the electron controlling layer ECL includes the electron injection layer EIL, the electron controlling layer ECL may include, e.g., LiF, lithium quinolate (LiQ), $Li_2O$, BaO, NaCl, CsF, a metal in lanthanoides such as Yb, or a metal halide such as RbCl and RbI. The electron injection layer may also be formed using a mixed material of a hole transport material and an insulating organo metal salt. The organo metal salt may be a material having an energy band gap of about 4 eV or more. In an implementation, the organo metal salt may include, e.g., a metal acetate, a metal benzoate, a metal acetoacetate, a metal acetylacetonate, or a metal stearate. The thickness of the electron injection layer may be from about 1 Å to about 100 Å, e.g., about 3 Å to about 90 Å. When the thickness of the electron injection layer satisfies the above described range, satisfactory electron injection property may be obtained without inducing the substantial increase of a driving voltage.

The electron controlling layer ECL may include a hole blocking layer, as described above. The hole blocking layer may include at least one of, e.g., 2,9-dimethyl-4,7-diphenyl-1,10-phenanthroline (BCP), or 4,7-diphenyl-1,10-phenanthroline (Bphen). The thickness of the hole blocking layer may be from about 20 Å to about 1,000 Å, e.g., about 30 Å to about 300 Å. In the case where the thickness of the hole blocking layer satisfies the above-described range, good hole blocking property may be obtained without a substantial increase of a driving voltage.

The second electrode EL2 may be provided on the electron controlling layer ECL. The second electrode EL2 may be a common electrode or a cathode. The second electrode EL2 may be a transmissive electrode, a transflective electrode, or a reflective electrode.

When the second electrode EL2 is the transmissive electrode, the second electrode EL2 may include, e.g., Li, Ca, LiF/Ca, LiF/Al, Al, Mg, BaF, Ba, Ag, a compound thereof or a mixture thereof (for example, a mixture of Ag and Mg).

The second electrode EL2 may include an auxiliary electrode. The auxiliary electrode may include a layer formed by depositing the above material so as to face the emission layer EML, and a transparent metal oxide, for example, ITO, IZO, ZnO, ITZO, Mo, Ti, etc. on the layer.

When the second electrode EL2 is the transflective electrode or the reflective electrode, the second electrode EL2 may include, e.g., Ag, Mg, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). For example, the second electrode EL2 may have a multilayered structure including a reflective layer or a transflective layer formed using the above-described materials and a transparent conductive layer formed using ITO, IZO, ZnO, ITZO, etc.

When the organic light emitting device OEL is a top emitting type, the first electrode EL1 may be a reflective electrode, and the second electrode EL2 may be a transmissive electrode or a transflective electrode. When the organic light emitting device OEL is a bottom emitting type, the first electrode EL1 may be a transmissive electrode or a transflective electrode, and the second electrode EL2 may be a reflective electrode.

In the organic light emitting device OEL according to an embodiment, a voltage may be applied to each of the first electrode EL1 and the second electrode EL2, and holes injected from the first electrode EL1 transport via the hole controlling layer HCL to the emission layer EML, and electrons injected from the second electrode EL2 transport via the electron controlling layer ECL to the emission layer EML. The electrons and the holes may be recombined in the emission layer EML to generate excitons, and the excitons may emit light via transition from an excited state to a ground state.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter the bipolar host material used in an embodiment and the organic light emitting device including the same will be explained in particular. In addition, the following embodiments are for illustration, and the bipolar host material according to an embodiment and the organic light emitting device including the same are not limited to the following embodiments.

EXAMPLES

<1. Synthesis of Bipolar Host Material>

A synthetic method of a bipolar host material used in an embodiment will be explained in particular referring to synthetic methods for Compounds H-1 to H-5.

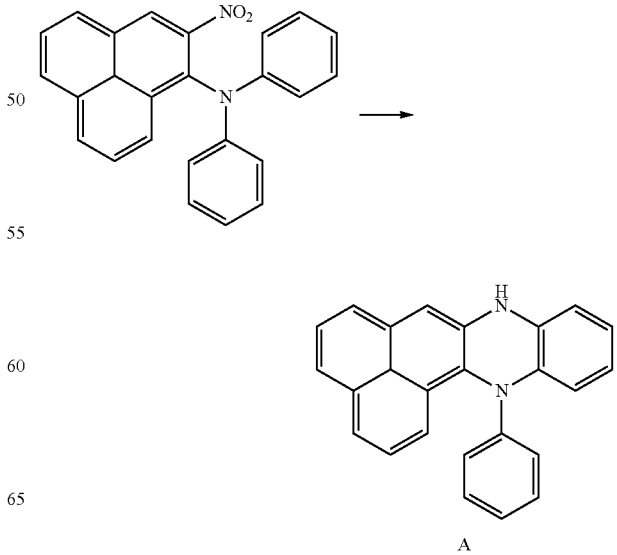

Reaction Scheme 1-1 schematically illustrates the synthetic method of Intermediate A used for the synthesis of a bipolar host material.

<Synthesis of Intermediate A>

5 g of 2-nitro-N,N-diphenyl-3a1H-phenalen-1-amine was dissolved in 15 g of triethylphosphite and then refluxed while stirring under nitrogen for about 12 hours. After finishing the reaction, unreacted triethylphosphite was removed through vacuum distillation, and extraction was performed using a solvent of hexane:methylene chloride in a ratio of 4:1 (v/v). Then, the reaction product was separated by chromatography to obtain a target compound, Intermediate A (Yield 46.5%).

(Reaction Scheme 1-2)

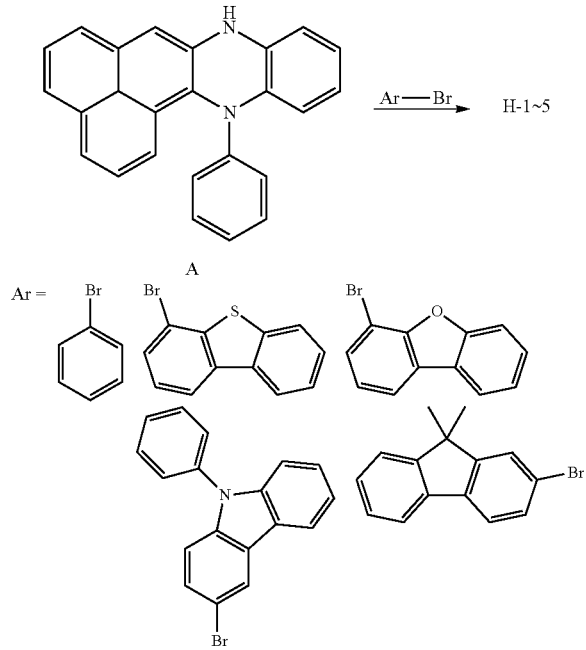

Reaction Scheme 2 schematically illustrates an embodiment of a reaction of synthesizing bipolar host materials Compounds H-1 to H-5 from Intermediate A.

<Synthesis of Compound H-1>

To a flask including synthesized Intermediate A and bromobenzene, 0.03 eq. of tris(dibenzilideneacetone)dipalladium(0) (Pd$_2$(dba)$_3$), 0.06 eq. of tributylphosphine, and toluene (0.1 M) were added and stirred. After about 12 hours, the reaction product was cooled to ambient temperature, extracted with methylene chloride, and washed with distilled water. The product thus obtained was dried with magnesium sulfate (MgSO$_4$), distilled under a reduced pressure, and separated by column chromatography to produce Compound H-1 (Yield 82%). The compound thus produced was identified using a high resolution mass spectrometer and $^1$H NMR. The mass of the compound thus synthesized was 421. [HRMS for C$_{31}$H$_{22}$N$_2$ [M]+: calcd: 422.53, found: 421, Elemental Analysis for C$_{31}$H$_{22}$N$_2$ calcd: C, 88.12; H, 5.25; N, 6.63].

<Synthesis of Compound H-2>

The same synthetic method for Compound H-1 was performed except for using Intermediate A and 4-bromodibenzo[d,b]thiophene (instead of bromobenzene) to produce Compound H-2 (Yield 81%). The compound thus produced was identified using a high resolution mass spectrometer and $^1$H NMR. The mass of the compound thus synthesized was 527. [HRMS for C$_{37}$H$_{24}$N$_2$S [M]+: calcd: 528.67, found: 527, Elemental Analysis for C$_{37}$H$_{24}$N$_2$S calcd: C, 84.06; H, 4.58; N, 5.30; S, 6.06].

<Synthesis of Compound H-3>

The same synthetic method for Compound H-1 was performed except for using Intermediate A and 4-bromodibenzo[d,b]furan (instead of bromobenzene) to produce Compound H-3 (Yield 77.4%). The compound thus produced was identified using a high resolution mass spectrometer and $^1$H NMR. The mass of the compound thus synthesized was 511. [HRMS for C$_{37}$H$_{24}$N$_2$O [M]+: calcd: 512.61, found: 511, Elemental Analysis for C$_{37}$H$_{24}$N$_2$O calcd: C, 86.69; H, 4.72; N, 5.46; 0, 3.12].

<Synthesis of Compound H-4>

The same synthetic method for Compound H-1 was performed except for using Intermediate A and (9-phenyl-9H-carbazol-3-yl)bromide (instead of bromobenzene) to produce Compound H-4 (Yield 79%). The compound thus produced was identified using a high resolution mass spectrometer and $^1$H NMR. The mass of the compound thus synthesized was 586. [HRMS for C$_{43}$H$_{29}$N$_3$ [M]+: calcd: 587.24, found: 586, Elemental Analysis for C$_{43}$H$_{29}$N$_3$ calcd: C, 87.88; H, 4.97; N, 7.15].

<Synthesis of Compound H-5>

The same synthetic method for Compound H-1 was performed except for using Intermediate A and 2-bromo-9,9-dimethyl-9H-fluorene (instead of bromobenzene) to produce Compound H-5 (Yield 82.7%). The compound thus produced was identified using a high resolution mass spectrometer and $^1$H NMR. The mass of the compound thus synthesized was 537. [HRMS for C$_{40}$H$_{30}$N$_2$ [M]+: calcd: 538.69, found: 537, Elemental Analysis for C$_{40}$H$_{30}$N$_2$ calcd: C, 89.19; H, 5.61; N, 5.20].

<2. Synthesis of Hole Transport Host Material>

The synthetic method of a hole transport host material used in an embodiment will be explained in particular referring to the synthetic method of Compounds A-1 to A-7.

(Reaction Scheme 2-1)

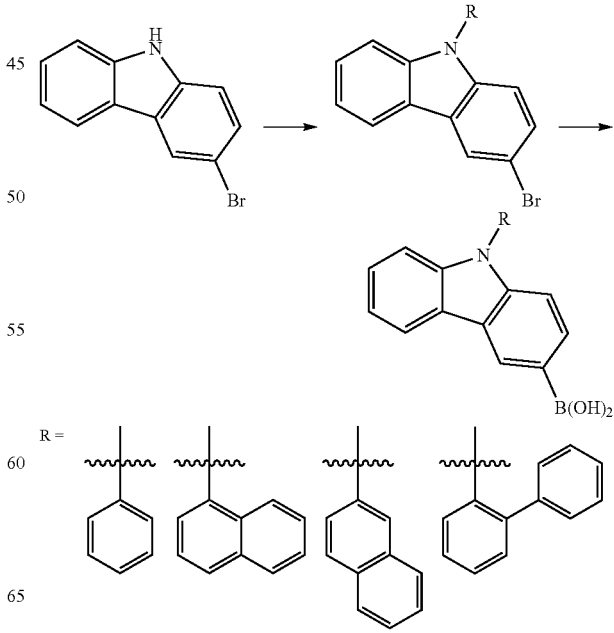

-continued

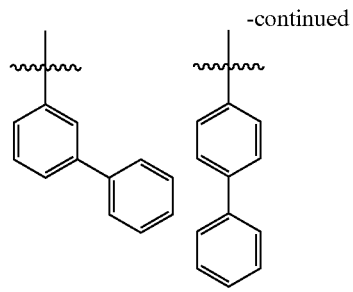

Reaction Scheme 2-1 schematically illustrates the synthetic method of an intermediate used for the synthesis of the hole transport host materials, Compounds A-1 to A-7.

Synthesis of 3-bromo-9-phenyl-9H-carbazole intermediate

To a flask including 3-bromo-9H-carbazole and iodobenzene, 0.03 eq. of tris(dibenzilideneacetone)dipalladium(0) ($Pd_2(dba)_3$), 0.06 eq. of tributylphosphine, and toluene (0.1 M) were added and stirred for about 12 hours. After that, the reaction product was cooled to ambient temperature, extracted with methylene chloride, and washed with distilled water. The product thus obtained was dried with magnesium sulfate ($MgSO_4$) and distilled under a reduced pressure, and the residue was separated by column chromatography to produce a 3-bromo-9-phenyl-9H-carbazole intermediate (Yield 87.22%). The mass of the compound identified using a high resolution mass spectrometer (HRMS) was 321, and the molecular formula was identified as $C_{18}H_{12}BrN$.

Synthesis of (9-phenyl-9H-carbazol-3-yl)boronic acid intermediate

To a flask including 3-bromo-9-phenyl-9H-carbazole, tetrahydrofuran (THF, 0.1 M) was added and then cooled to about −78° C. Then, 1.2 eq. of n-butyl lithium (n-BuLi, dissolved in hexane with a concentration of 1.6 M) was added and then stirred for about 30 minutes. 1.2 eq. of methylborate was added at the same temperature, and then, the temperature was gradually increased to ambient temperature. After stirring for about 1 hour, 50 ml of a 1N HCl solution was gradually added and then stirred for about 10 minutes. An organic layer was extracted with ethyl acetate and washed with distilled water. The product thus obtained was dried with magnesium sulfate ($MgSO_4$) and distilled under a reduced pressure. The residue was recrystallized using ethyl acetate (EA):hexane (Hex) in a ratio of 1:10 to produce a (9-phenyl-9H-carbazol-3-yl)boronic acid intermediate (Yield 69.82%). The mass of the compound identified using a high resolution mass spectrometer (HRMS) was 286, and the molecular formula was identified as $C_{18}H_{14}BNO_2$.

Synthesis of 3-bromo-9-(naphthalen-1-yl)-9H-carbazole intermediate

To a flask including 3-bromo-9H-carbazole and 1-iodonaphthalene, 0.03 eq. of tris(dibenzilideneacetone)dipalladium(0) ($Pd_2(dba)_3$), 0.06 eq. of tributylphosphine, and toluene (0.1 M) were added and stirred for about 12 hours. After that, the reaction product was cooled to ambient temperature, extracted with methylene chloride, and washed with distilled water. The product thus obtained was dried with magnesium sulfate ($MgSO_4$) and distilled under a reduced pressure, and the residue was separated by column chromatography to produce a 3-bromo-9-(naphthalen-1-yl)-9H-carbazole intermediate (Yield 84.24%). The mass of the compound identified using a high resolution mass spectrometer (HRMS) was 371, and the molecular formula was identified as $C_{22}H_{14}BrN$.

Synthesis of (9-naphthalen-1-yl)-9H-carbazol-3-yl)boronic acid intermediate

To a flask including 3-bromo-9-(naphthalene-1-yl)-9H-carbazole, tetrahydrofuran (THF, 0.1 M) was added and then cooled to about −78° C. After that, 1.2 eq. of n-butyl lithium (n-BuLi, dissolved in hexane with a concentration of 1.6 M) was added and then stirred for about 30 minutes. 1.2 eq. of methylborate was added at the same temperature, and then, the temperature was gradually increased to ambient temperature. After stirring for about 1 hour, 50 ml of a 1N HCl solution was gradually added and then stirred for about 10 minutes. An organic layer was extracted with ethyl acetate and washed with distilled water. The product thus obtained was dried with magnesium sulfate ($MgSO_4$) and distilled under a reduced pressure. The residue was recrystallized using ethyl acetate (EA):hexane (Hex) in a ratio of 1:10 to produce a (9-(naphthalen-1-yl)-9H-carbazol-3-yl)boronic acid intermediate (Yield 71.4%). The mass of the compound identified using a high resolution mass spectrometer (HRMS) was 336, and the molecular formula was identified as $C_{22}H_{16}BNO_2$.

Synthesis of 3-bromo-9-(naphthalene-2-yl)-9H-carbazole intermediate

To a flask including 3-bromo-9H-carbazole and 2-iodonaphthalene, 0.03 eq. of tris(dibenzilideneacetone)dipalladium(0) ($Pd_2(dba)_3$), 0.06 eq. of tributylphosphine, and toluene (0.1 M) were added and stirred for about 12 hours. After that, the reaction product was cooled to ambient temperature, extracted with methylene chloride, and washed with distilled water. The product thus obtained was dried with magnesium sulfate ($MgSO_4$) and distilled under a reduced pressure, and the residue was separated by column chromatography to produce a 3-bromo-9-(naphthalen-2-yl)-9H-carbazole intermediate (Yield 85.1%). The mass of the compound identified using a high resolution mass spectrometer (HRMS) was 371, and the molecular formula was identified as $C_{22}H_{14}BrN$.

Synthesis of (9-naphthalen-2-yl)-9H-carbazol-3-yl)boronic acid intermediate

To a flask including 3-bromo-9-(naphthalen-2-yl)-9H-carbazole, tetrahydrofuran (THF, 0.1 M) was added and then cooled to about −78° C. After that, 1.2 eq. of n-butyl lithium (n-BuLi, dissolved in hexane with a concentration of 1.6 M) was added and then stirred for about 30 minutes. 1.2 eq. of methylborate was added at the same temperature, and then, the temperature was gradually increased to ambient temperature. After stirring for about 1 hour, 50 ml of a 1N HCl solution was gradually added and then stirred for about 10 minutes. An organic layer was extracted with ethyl acetate and washed with distilled water. The product thus obtained was dried with magnesium sulfate (MgSO$_4$) and distilled under a reduced pressure. The residue was recrystallized using ethyl acetate (EA):hexane (Hex) in a ratio of 1:10 to produce a (9-(naphthalen-2-yl)-9H-carbazol-3-yl)boronic acid intermediate (Yield 70.6%). The mass of the compound identified using a high resolution mass spectrometer (HRMS) was 336, and the molecular formula was identified as C$_{22}$H$_{16}$BNO$_2$.

Synthesis of
3-bromo-9-(naphthalen-2-yl)-9H-carbazole

To a flask including 3-bromo-9H-carbazole and 2-iodo-1,1'-biphenyl, 0.03 eq. of tris(dibenzilideneacetone)dipalladium(0) (Pd$_2$(dba)$_3$), 0.06 eq. of tributylphosphine, and toluene (0.1 M) were added and stirred for about 12 hours. After that, the reaction product was cooled to ambient temperature, extracted with methylene chloride, and washed with distilled water. The product thus obtained was dried with magnesium sulfate (MgSO$_4$) and distilled under a reduced pressure, and the residue was separated by column chromatography to produce a 3-bromo-9-(naphthalen-2-yl)-9H-carbazole intermediate (Yield 81.4%). The mass of the compound identified using a high resolution mass spectrometer (HRMS) was 397, and the molecular formula was identified as C$_{24}$H$_{16}$BrN.

Synthesis of (9-([1,1'-biphenyl]-2-yl)-9H-carbazol-2-yl)boronic acid intermediate To a flask including 3-bromo-9-(naphthalen-2-yl)-9H-carbazole, tetrahydrofuran (THF, 0.1 M) was added and then cooled to about −78° C. Then, 1.2 eq. of n-butyl lithium (n-BuLi, dissolved in hexane with a concentration of 1.6 M) was added and then stirred for about 30 minutes. 1.2 eq. of methylborate was added at the same temperature, and then, the temperature was gradually increased to ambient temperature. After stirring for about 1 hour, 50 ml of a 1N HCl solution was gradually added and then stirred for about 10 minutes. An organic layer was extracted with ethyl acetate and washed with distilled water. The product thus obtained was dried with magnesium sulfate (MgSO$_4$) and distilled under a reduced pressure. The residue was recrystallized using ethyl acetate (EA):hexane (Hex) in a ratio of 1:10 to produce a (9-([1,1'-biphenyl]-2-yl)-9H-carbazol-3-yl)boronic acid intermediate (Yield 78.4%). The mass of the compound identified using a high resolution mass spectrometer (HRMS) was 362, and the molecular formula was identified as C$_{24}$H$_{18}$BNO$_2$.

Synthesis of
3-bromo-9-(naphthalen-3-yl)-9H-carbazole
intermediate

To a flask including 3-bromo-9H-carbazole and 2-iodo-1,1'-biphenyl, 0.03 eq. of tris(dibenzilideneacetone)dipalladium(0) (Pd$_2$(dba)$_3$), 0.06 eq. of tributylphosphine, and toluene (0.1 M) were added and stirred for about 12 hours. After that, the reaction product was cooled to ambient temperature, extracted with methylene chloride, and washed with distilled water. The product thus obtained was dried with magnesium sulfate (MgSO$_4$) and distilled under a reduced pressure, and the residue was separated by column chromatography to produce a 3-bromo-9-(naphthalen-3-yl)-9H-carbazole intermediate (Yield 83.6%). The mass of the compound identified using a high resolution mass spectrometer (HRMS) was 362, and the molecular formula was identified as C$_{22}$H$_{14}$BrN.

Synthesis of (9-([1,1'-biphenyl]-3-yl)-9H-carbazol-3-yl)boronic acid intermediate To a flask including 3-bromo-9-(naphthalen-3-yl)-9H-carbazole, tetrahydrofuran (THF, 0.1 M) was added and then cooled to about −78° C. After that, 1.2 eq. of n-butyl lithium (n-BuLi, dissolved in hexane with a concentration of 1.6 M) was added and then stirred for about 30 minutes. 1.2 eq. of methylborate was added at the same temperature, and then, the temperature was gradually increased to ambient temperature. After stirring for about 1 hour, 50 ml of an 1N HCl solution was gradually added and then stirred for about 10 minutes. An organic layer was extracted with ethyl acetate and washed with distilled water. The product thus obtained was dried with magnesium sulfate (MgSO$_4$) and distilled under a reduced pressure. The residue was recrystallized using ethyl acetate (EA):hexane (Hex) in a ratio of 1:10 to produce a (9-([1,1'-biphenyl]-3-yl)-9H-carbazol-3-yl)boronic acid intermediate (Yield 74.4%). The mass of the compound identified using a high resolution mass spectrometer (HRMS) was 362, and the molecular formula was identified as C$_{24}$H$_{18}$BNO$_2$.

Synthesis of
3-bromo-9-(naphthalen-4-yl)-9H-carbazole
intermediate

To a flask including 3-bromo-9H-carbazole and 4-iodo-1,1'-biphenyl, 0.03 eq. of tris(dibenzilideneacetone)dipalladium(0) (Pd$_2$(dba)$_3$), 0.06 eq. of tributylphosphine, and toluene (0.1 M) were added and stirred for about 12 hours. After that, the reaction product was cooled to ambient temperature, extracted with methylene chloride, and washed with distilled water. The product thus obtained was dried with magnesium sulfate (MgSO$_4$) and distilled under a reduced pressure, and the residue was separated by column chromatography to produce a 3-bromo-9-(naphthalen-4-yl)-9H-carbazole intermediate (Yield 87.6%). The mass of the compound identified using a high resolution mass spectrometer (HRMS) was 371, and the molecular formula was identified as C$_{22}$H$_{14}$BrN.

Synthesis of (9-([1,1'-biphenyl]-4-yl)-9H-carbazol-3-yl)boronic acid intermediate To a flask including 3-bromo-9-(naphthalen-4-yl)-9H-carbazole, tetrahydrofuran (THF, 0.1 M) was added and then cooled to about −78° C. After that, 1.2 eq. of n-butyl lithium (n-BuLi, dissolved in hexane with a concentration of 1.6 M) was added and then stirred for about 30 minutes. 1.2 eq. of methylborate was added at the same temperature, and then, the temperature was gradually increased to ambient temperature. After stirring for about 1 hour, 50 ml of a 1N HCl solution was gradually added and then stirred for about 10 minutes. An organic layer was extracted with ethyl acetate and washed with distilled water. The product thus obtained was dried with magnesium sulfate (MgSO$_4$) and distilled under a reduced pressure. The residue was recrystallized using ethyl acetate (EA):hexane (Hex) in a ratio of 1:10 to produce a (9-([1,1'-biphenyl]-4-yl)-9H-carbazol-3-yl)boronic acid intermediate (Yield 75.2%). The mass of the compound identified using a high resolution mass spectrometer (HRMS) was 362, and the molecular formula was identified as $C_{24}H_{18}BNO_2$.

<Synthesis of Compound A-1>

To a flask including 1 eq. of 3-bromo-9-phenyl-9H-carbazole and 1.2 eq. of (9-phenyl-9H-carbazol-3-yl)boronic acid, 0.03 eq. of tris(dibenzilideneacetone)dipalladium (0) $(Pd_2(dba)_3)$, 0.06 eq. of tributylphosphine, and toluene (0.1 M) were added and refluxed while stirring for about 12 hours. After that, the reaction product was cooled to ambient temperature, extracted with methylene chloride, and washed with distilled water. The product thus obtained was dried with magnesium sulfate $(MgSO_4)$ and distilled under a reduced pressure, and the residue was separated by column chromatography to produce Compound A-1 (Yield 82%). The compound thus produced was identified using a high resolution mass spectrometer and $^1H$ NMR. The mass of the product thus synthesized was 483.

<Synthesis of Compound A-2>

The same synthetic method for Compound A-1 was performed except for using 1 eq. of a 3-bromo-9-(naphthalen-1-yl)-9H-carbazole intermediate (instead of 3-bromo-9-phenyl-9H-carbazole) and 1.2 eq. of (9-(naphthalen-1-yl)-9H-carbazol-3-yl)boronic acid (instead of (9-phenyl-9H-carbazol-3-yl)boronic acid) to produce Compound A-2 (Yield 80.4%). The compound thus produced was identified using a high resolution mass spectrometer and 1H NMR. The mass of the compound thus synthesized was 583.

<Synthesis of Compound A-3>

The same synthetic method for Compound A-1 was performed except for using 1 eq. of a 3-bromo-9-(naphthalen-2-yl)-9H-carbazole intermediate (instead of 3-bromo-9-phenyl-9H-carbazole) and 1.2 eq. of (9-(naphthalen-2-yl)-9H-carbazol-3-yl)boronic acid (instead of (9-phenyl-9H-carbazol-3-yl)boronic acid) to produce Compound A-3 (Yield 81.7%). The compound thus produced was identified using a high resolution mass spectrometer and $^1H$ NMR. The mass of the compound thus synthesized was 583. [HRMS for $C_{44}H_{28}N_2$ [M]+: calcd: 584.72, found: 583, Elemental Analysis for $C_{44}H_{28}N_2$ calcd: C, 90.38; H, 4.83; N, 4.79].

<Synthesis of Compound A-4>

The same synthetic method for Compound A-1 was performed except for using 1 eq. of a 3-bromo-9-(naphthalen-2-yl)-9H-carbazole intermediate (instead of 3-bromo-9-phenyl-9H-carbazole) and 1.2 eq. of (9-([1,1'-biphenyl]-2-yl)-9H-carbazol-3-yl)boronic acid (instead of (9-phenyl-9H-carbazol-3-yl)boronic acid) to produce Compound A-4 (Yield 78.7%). The compound thus produced was identified using a high resolution mass spectrometer and $^1H$ NMR. The mass of the compound thus synthesized was 609. [HRMS for $C_{46}H_{30}N_2$ [M]+: calcd: 610.76, found: 609, Elemental Analysis for $C_{46}H_{30}N_2$ calcd: C, 90.46; H, 4.95; N, 4.59].

<Synthesis of Compound A-5>

The same synthetic method for Compound A-1 was performed except for using 1 eq. of a 9-([1,1'-biphenyl]-2-yl)-3-bromo-9H-carbazole intermediate (instead of 3-bromo-9-phenyl-9H-carbazole) and 1.2 eq. of (9-[1,1'-biphenyl]-2-yl)-9H-carbazol-3-yl)boronic acid (instead of (9-phenyl-9H-carbazol-3-yl)boronic acid) to produce Compound A-5 (Yield 72.6%). The compound thus produced was identified using a high resolution mass spectrometer and $^1H$ NMR. The mass of the compound thus produced was 635. [HRMS for $C_{48}H_{32}N_2$ [M]+: calcd: 636.80, found: 635, Elemental Analysis for $C_{48}H_{32}N_2$ calcd: C, 90.54; H, 5.07; N, 4.40].

<Synthesis of Compound A-6>

The same synthetic method for Compound A-1 was performed except for using 1 eq. of a 9-([1,1'-biphenyl]-3-yl)-3-bromo-9H-carbazole intermediate (instead of 3-bromo-9-phenyl-9H-carbazole) and 1.2 eq. of (9-[1,1'-biphenyl]-3-yl)-9H-carbazol-3-yl)boronic acid (instead of (9-phenyl-9H-carbazol-3-yl)boronic acid) to produce Compound A-6 (Yield 75.4%). The compound thus produced was identified using a high resolution mass spectrometer and $^1H$ NMR. The mass of the compound thus produced was 635. [HRMS for $C_{48}H_{32}N_2$ [M]+: calcd: 636.80, found: 635, Elemental Analysis for $C_{48}H_{32}N_2$ calcd: C, 90.54; H, 5.07; N, 4.40].

<Synthesis of Compound A-7>

The same synthetic method for Compound A-1 was performed except for using 1 eq. of a 9-([1,1'-biphenyl]-4-yl)-3-bromo-9H-carbazole intermediate (instead of 3-bromo-9-phenyl-9H-carbazole) and 1.2 eq. of (9-phenyl-9H-carbazol-3-yl)boronic acid to produce Compound A-7 (Yield 77.1%). The compound thus produced was identified using a high resolution mass spectrometer and $^1H$ NMR. The mass of the compound thus produced was 559. [HRMS for $C_{42}H_{28}N_2$ [M]+: calcd: 560.7, found: 559, Elemental Analysis for $C_{42}H_{28}N_2$ calcd: C, 89.97; H, 5.03; N, 5.00].

<3. Synthesis of Electron Transport Host Material>

(Reaction Scheme 3-1)

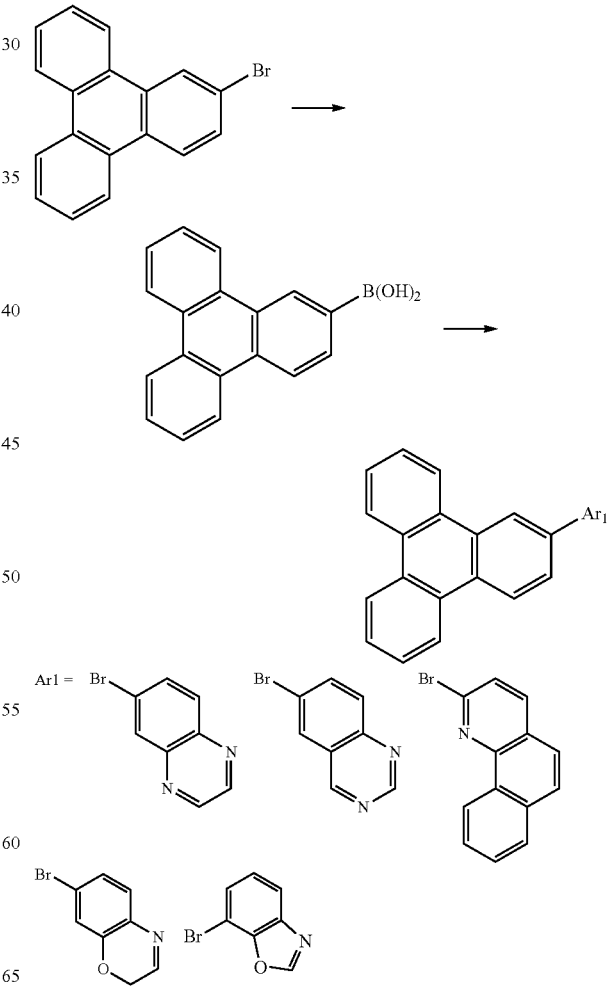

Reaction Scheme 3-1 schematically illustrates the synthetic method of an intermediate used for the synthesis of electron transport host materials, Compounds B-1, B-2, B-6, B-12, and B-17.

Synthesis of triphenylen-2-ylboronic acid intermediate

To a flask including 2-bromotriphenylene, tetrahydrofuran (0.1 M) was added and then cooled to about −78° C. Then, 1.2 eq. of n-butyl lithium (n-BuLi, dissolved in hexane with a concentration of 1.6 M) was added and then stirred for about 30 minutes. 1.2 eq. of methylborate was added at the same temperature, and then, the temperature was gradually increased to ambient temperature. After stirring for about 1 hour, 50 ml of a 1N HCl solution was gradually added and then stirred for about 10 minutes. An organic layer was extracted with ethyl acetate (EA) and washed with distilled water. The product thus obtained was dried with magnesium sulfate ($MgSO_4$) and distilled under a reduced pressure. The residue was recrystallized using ethyl acetate (EA):hexane (Hex) in a ratio of 1:10 to produce a triphenylen-2-ylboronic acid intermediate (Yield 77.4%). The mass of the compound identified using a high resolution mass spectrometer (HRMS) was 271. [HRMS for $C_{18}H_{13}BO_2$ [M]+: calcd: 272.11, found: 271].

<Synthesis of Compound B-1>

To a flask including 1 eq. of triphenylen-2-ylboronic acid and 1.2 eq. of 6-bromoquinoxaline, 0.03 eq. of $Pd(dba)_3$, 0.06 eq. of $(t-Bu)_3P$, and toluene (1 M) were added and refluxed with stirring for about 12 hours. Then, the reaction product was cooled to ambient temperature, extracted with methylene chloride and washed with distilled water. The product thus obtained was dried with $MgSO_4$ and distilled under a reduced pressure, and the residue was separated by column chromatography to produce Compound B-1 (Yield 80.4%). The compound thus produced was identified using a high resolution mass spectrometer and $^1H$ NMR. The mass of the synthesized compound thus identified was 355. [HRMS for $C_{26}H_{16}N_2$ [M]+: calcd: 356.43, found: 355, Elemental Analysis for $C_{26}H_{16}N_2$ calcd: C, 87.62; H, 4.52; N, 7.86].

<Synthesis of Compound B-2>

The same synthetic method for Compound B-1 was performed except for using 1 eq. of a triphenylen-2-ylboronic acid intermediate and 1.2 eq. of 6-bromoquinazoline (instead of 6-bromoquinoxaline) to produce Compound B-2 (Yield 79.2%). The compound thus produced was identified using a high resolution mass spectrometer and $^1H$ NMR. The mass of the compound thus produced was 355. [HRMS for $C_{26}H_{16}N_2$ [M]+: calcd: 356.43, found: 355, Elemental Analysis for $C_{26}H_{16}N_2$ calcd: C, 87.62; H, 4.52; N, 7.86].

<Synthesis of Compound B-6>

The same synthetic method for Compound B-1 was performed except for using 1 eq. of a triphenylen-2-ylboronic acid intermediate and 1.2 eq. of 2-bromobenzo[h]quinoline (instead of 6-bromoquinoxaline) to produce Compound B-6 (Yield 76.1%). The compound thus produced was identified using a high resolution mass spectrometer and $^1H$ NMR. The mass of the compound thus produced was 404. [HRMS for $C_{31}H_{19}N$ [M]+: calcd: 405.50, found: 404, Elemental Analysis for $C_{31}H_{19}N$ calcd: C, 91.82; H, 4.72; N, 3.45].

<Synthesis of Compound B-12>

The same synthetic method for Compound B-1 was performed except for using 1 eq. of a triphenylen-2-ylboronic acid intermediate and 1.2 eq. of 7-bromo-2H-benzo[b][1,4]oxazine (instead of 6-bromoquinoxaline) to produce Compound B-12 (Yield 74.2%). The compound thus produced was identified using a high resolution mass spectrometer and $^1H$ NMR. The mass of the compound thus produced was 358. [HRMS for $C_{26}H_{17}NO$ [M]+: calcd: 359.43, found: 358, Elemental Analysis for $C_{26}H_{17}NO$ calcd: C, 86.88; H, 4.77; N, 3.90; 0, 4.45].

<Synthesis of Compound B-17>

The same synthetic method for Compound B-1 was performed except for using 1 eq. of a triphenylen-2-ylboronic acid intermediate and 1.2 eq. of 7-bromobenzo[d]oxazole (instead of 6-bromoquinoxaline) to produce Compound B-17 (Yield 78.2%). The compound thus produced was identified using a high resolution mass spectrometer and $^1H$ NMR. The mass of the compound thus produced was 344. [HRMS for $C_{25}H_{15}NO$ [M]+: calcd: 345.40, found: 344, Elemental Analysis for $C_{25}H_{15}NO$ calcd: C, 86.94; H, 4.38; N, 4.06; 0, 4.63].

<4. Manufacture of Organic Light Emitting Device>

An ITO glass substrate was ultrasonically cleansed using isopropyl alcohol and then, pure water and was surface treated using ultraviolet rays and ozone ($O_3$). After the surface treatment, the ITO glass substrate was installed in a vacuum deposition apparatus. Then, a hole injection layer, a hole transport layer, an emission layer, and an electron transport layer were deposited on the ITO glass substrate one by one.

The hole injection layer was formed using 4,4',4"-tris(N, N-2-naphthylphenylamino)triphenylamine (2-TNATA) to a layer thickness of about 600 Å. On the hole injection layer, the hole transport layer was formed using N,N'-di(1-naphthyl)-N,N'-diphenylbenzidine (NPB). The hole transport layer was formed by vacuum deposition to a thickness of about 300 Å.

On the hole transport layer, the emission layer was deposited and formed. The emission layer was formed by co-depositing a host material and a dopant material. In the emission layer, a green phosphorescent dopant, bis-(1-phenylisoquinolyl) iridium(III)acetylacetonate ($Ir(ppy)_3$) was used as the dopant material.

The host material used in the emission layer was different in each of the Examples and Comparative Examples. In the Examples, a hole transport host material, an electron transport host material, and a bipolar host material were used all together as the host materials of the emission layer. In the emission layer, the host material and the dopant material were deposited in a weight ratio of about 85:15. The emission layer was deposited to a thickness of about 300 Å.

On the emission layer, $Alq_3$ was deposited to a thickness of about 300 Å as an electron transport layer. After that, Al was vacuum deposited to a thickness of about 1,200 Å to form a second electrode.

In the following Table 1, the configuration of the host materials in the emission layer in the Examples and Comparative Examples are shown.

TABLE 1

|  | Host material 1 | Host material 2 | Host material 3 | Weight Ratio |
|---|---|---|---|---|
| Example 1 | A-1 | B-1 | H-1 | 3:4:3 |
| Example 2 | A-2 | B-1 | H-3 | 3:4:3 |
| Example 3 | A-2 | B-6 | H-5 | 4:4:2 |
| Example 4 | A-4 | B-1 | H-3 | 5:3:2 |
| Example 5 | A-2 | B-12 | H-5 | 3:4:3 |
| Example 6 | A-3 | B-1 | H-1 | 4:4:2 |
| Example 7 | A-4 | B-17 | H-5 | 5:3:2 |

TABLE 1-continued

|  | Host material 1 | Host material 2 | Host material 3 | Weight Ratio |
|---|---|---|---|---|
| Example 8 | A-5 | B-6 | H-2 | 5:3:2 |
| Example 9 | A-6 | B-12 | H-4 | 3:4:3 |
| Example 10 | A-6 | B-17 | H-5 | 4:4:2 |
| Example 11 | A-7 | B-2 | H-4 | 5:3:2 |
| Example 12 | A-7 | B-2 | H-5 | 4:4:2 |
| Comparative Example 1 | A-1 | CBP | H-1 | 5:3:2 |
| Comparative Example 2 | CBP | B-2 | H-1 | 5:3:2 |
| Comparative Example 3 | CBP |  |  |  |
| Comparative Example 4 | A-1 | B-1 |  | 5:5 |
| Comparative Example 5 |  | B-1 | H-1 | 5:5 |

Referring to Table 1, the hole transport host materials described above were used as host material 1 were used in Examples 1 to 12, and the electron transport host materials described above were used as host material 2. In addition, the host materials described above were used as the bipolar host material.

In Comparative Example 1, 4,4'-bis(N-carbazolyl)-1,1'-biphenyl (CBP) was used as host material 2, when compared to that in Example 1. In Comparative Example 2, 4,4'-bis(N-carbazolyl)-1,1'-biphenyl (CBP) was used as host material 1, when compared to that in Example 1.

In Comparative Example 3, 4,4'-bis(N-carbazolyl)-1,1'-biphenyl (CBP) was used alone as a single host material.

In Comparative Examples 4 and 5, only two kinds of host materials were used. In Comparative Example 4, a hole transport host material and an electron transport host material were used. In Comparative Example 5, an electron transport host material and a bipolar host material were used.

In Table 2, below, evaluation results of the light emitting devices according to the Examples and Comparative Examples explained in Table 1 are shown. For the evaluation of the properties of the organic light emitting devices according to the Examples and Comparative Examples, efficiency and device life were measured. The efficiency was evaluated with a current density of 10 mA/cm², and initial luminance for evaluating emission life was set to 6,000 nit.

TABLE 2

|  | Efficiency (cd/A) | Life (hrs) |
|---|---|---|
| Example 1 | 47.3 | 970 |
| Example 2 | 44.1 | 921 |
| Example 3 | 45 | 943 |
| Example 4 | 43 | 900 |
| Example 5 | 44 | 910 |
| Example 6 | 42 | 860 |
| Example 7 | 45 | 885 |
| Example 8 | 48 | 910 |
| Example 9 | 46 | 920 |
| Example 10 | 47 | 910 |
| Example 11 | 43 | 915 |
| Example 12 | 43 | 900 |
| Comparative Example 1 | 43 | 500 |
| Comparative Example 2 | 40 | 600 |
| Comparative Example 3 | 30 | 100 |
| Comparative Example 4 | 43 | 340 |
| Comparative Example 5 | 37 | 670 |

Referring to the results in Table 2, three host materials were included at the same time in the emission layer for Examples 1 to 12, and had improved emission efficiency and device life, when compared to those of Comparative Example 3 in which only one kind of the host material was used. In addition, the life of the light emitting devices according to Examples 1 to 12 were remarkably improved when compared to those of Comparative Examples 4 and 5 using only two kinds of the host materials in the emission layer.

In addition, the emission efficiency and the life of the organic light emitting device according to Example 1, in which three kinds of the exemplified host materials were used were improved when compared to those of Comparative Examples 1 and 2, in which only two kinds of the exemplified host materials were used.

The results were obtained, because it is believed that the carbazole hole transport host material may contribute to the improvement of the life, and the triphenylene electron transport host material may contribute to the improvement of the device. In addition, both the efficiency and life of the emission device may be increased by further including the bipolar host material, which may have both hole transport property and electron transport property according to the kind of a substituent in the emission layer.

Hereinafter, a display device according to an embodiment including the organic light emitting device according to an embodiment will be explained referring to FIGS. 2 to 5.

Figure 2:
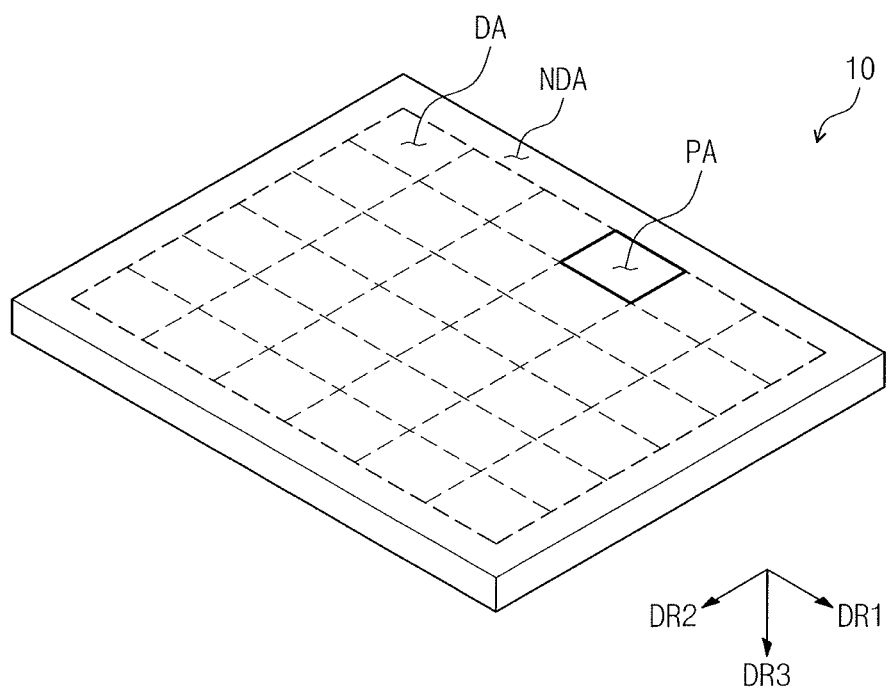
FIG. 2 illustrates a perspective view schematically showing a display device according to an embodiment.

FIG. 2 illustrates a perspective view schematically showing a display device according to an embodiment. Referring to FIG. 2, a display device 10 may include a display area DA and a non-display area NDA.

The display area DA displays images. In an implementation, when seen the display device 10 from a thickness direction (for example, in DR3), the display area DA may have approximately a rectangular shape.

The display area DA may include a plurality of pixel areas PA. The pixel areas PA may be disposed in a matrix shape. The pixel areas PA may be defined by a pixel defining layer (PDL in FIG. 5). The pixel areas PA may include each of the plurality of pixels (PX in FIG. 3).

The non-display area NDA may not display images. When seen the display device 10 from a thickness direction (in DR3), the non-display area NDA may, e.g., surround the display area DA. The non-display area NDA may be adjacent to the display area DA in a first direction (for example, in DR1) and a second direction (for example, in DR2) which crosses the first direction.

Figure 3:
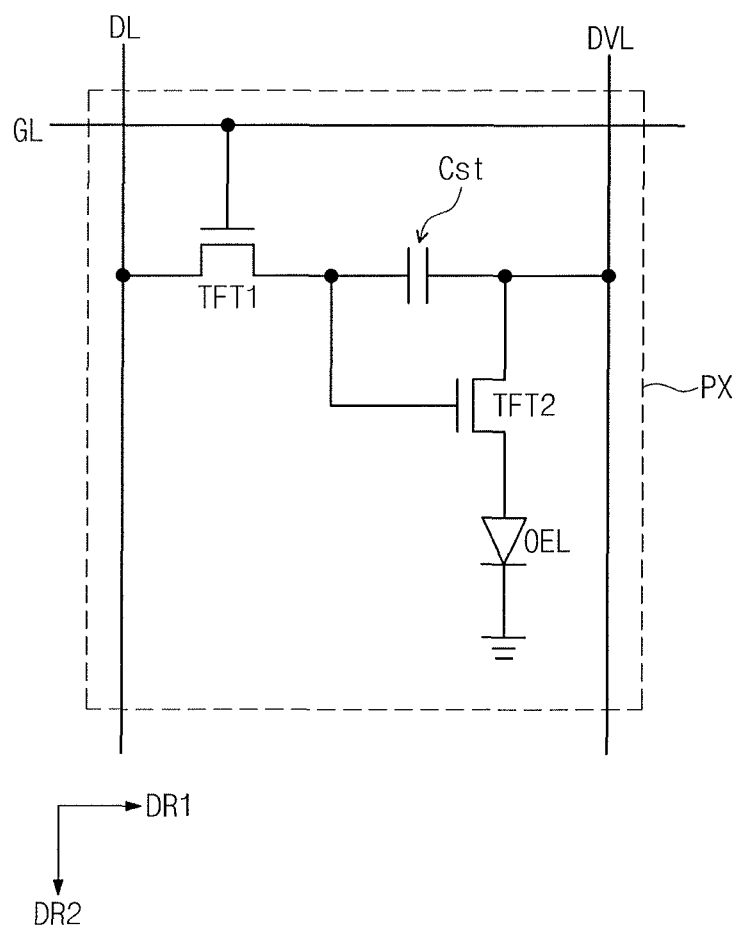
FIG. 3 illustrates a circuit diagram of one pixel included in a display device according to an embodiment.
Figure 4:
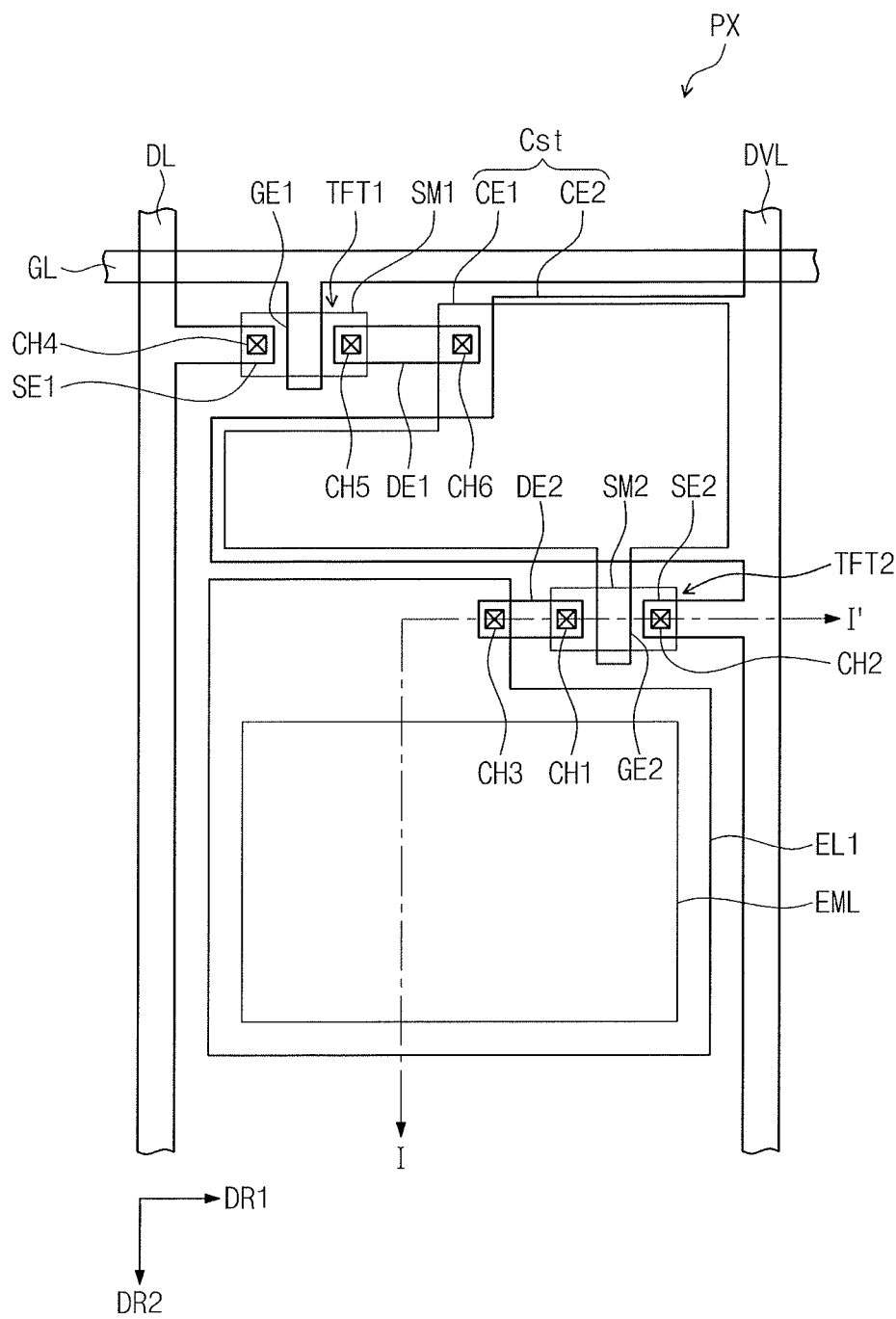
FIG. 4 illustrates a plan view of one pixel included in a display device according to an embodiment.

FIG. 3 illustrates a circuit diagram of one pixel included in a display device according to an embodiment. FIG. 4 illustrates a plan view of one pixel included in a display device according to an embodiment and FIG. 5 illustrates a schematic cross-sectional view corresponding to line I-I' in FIG. 4.

Figure 5:
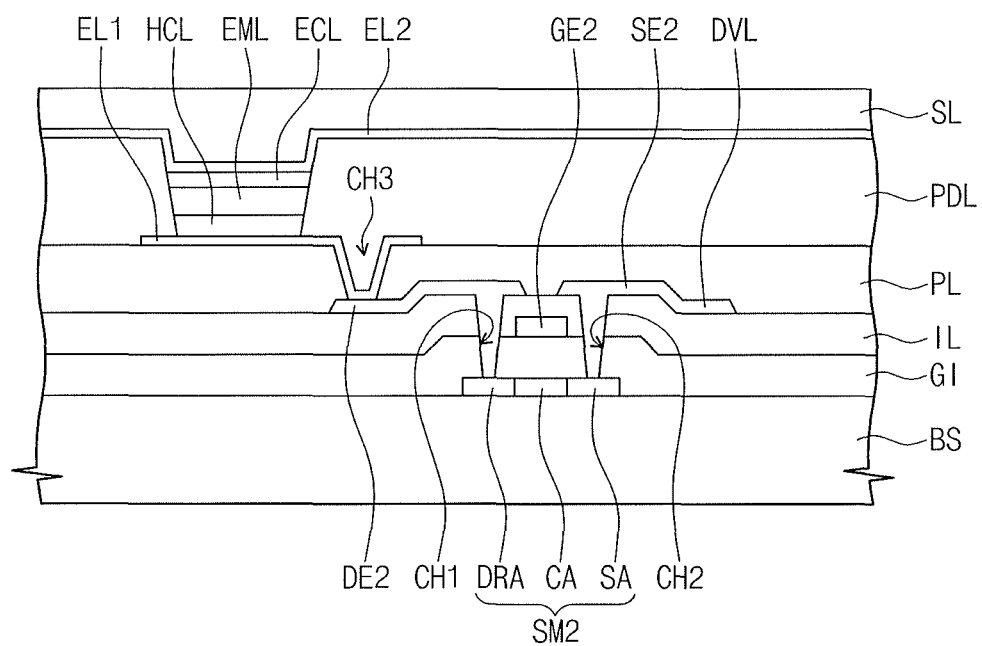
FIG. 5 illustrates a schematic cross-sectional view corresponding to line I-I' in FIG. 4.

Referring to FIGS. 3 to 5, each of the pixels PX may include a wire part including a gate line GL, a data line DL, and a driving voltage line DVL, and thin film transistors TFT1 and TFT2 which are connected to the wire part, an organic light emitting device OEL connected to the thin film transistors TFT1 and TFT2, and a capacitor Cst.

Each of the pixels PX may emit light having a specific color, for example, one of red light, green light, or blue light. In an implementation, the kind of the light may additionally or alternative include cyan light, magenta light, yellow light, etc.

The gate line GL may be extended in a first direction DR1. The data line DL may be extended in a second direction DR2 which crosses the gate line GL. The driving voltage line DVL may be extended in substantially the same direction as the data line DL, that is, the second direction DR2. The gate line GL transmits scanning signals to the thin film transistors TFT1 and TFT2, and the data line DL transmits data signals to the thin film transistors TFT1 and TFT2, and the driving voltage line DVL provides driving voltages to the thin film transistors TFT1 and TFT2.

The thin film transistors TFT1 and TFT2 may include a driving thin film transistor TFT2 for controlling the organic light emitting device OEL, and a switching thin film transistor TFT1 for switching the driving thin film transistor TFT2. In an implementation, each of the pixels PX includes two thin film transistors TFT1 and TFT2. Each of the pixels PX may include one thin film transistor and one capacitor, or each of the pixels PX may include at least three thin film transistors and at least two capacitors.

The switching thin film transistor TFT1 may include a first gate electrode GE1, a first source electrode SE1, and a first drain electrode DE1. The first gate electrode GE1 may be connected to the gate line GL, and the first source electrode SE1 may be connected to the data line DL. The first drain electrode DE1 may be connected to a first common electrode CE1 via a fifth contact hole CH5. The switching thin film transistor TFT1 may transmit data signals applied to the data line DL to the driving thin film transistor TFT2 according to scanning signals applied to the gate line GL.

The driving thin film transistor TFT2 may include a second gate electrode GE2, a second source electrode SE2, and a second drain electrode DE2. The second gate electrode GE2 may be connected to the first common electrode CE1. The second source electrode SE2 may be connected to the driving voltage line DVL. The second drain electrode DE2 may be connected to the first electrode EL1 via a third contact hole CH3.

The first electrode EL1 is connected with the second drain electrode DE2 of the driving thin film transistor TFT2. A common voltage is applied to the second electrode EL2, and the emission layer EML emits light according to the output signals of the driving thin film transistor TFT2, thereby displaying images. In this case, the light emitted from the emission layer EML may be changed according to the kind of the dopants.

The capacitor Cst may be connected between the second gate electrode GE2 and the second source electrode SE2 of the driving thin film transistor TFT2, and charges and maintains data signals inputted to the second gate electrode GE2 of the driving thin film transistor TFT2. The capacitor Cst may include the first common electrode CE1 connected to the first drain electrode DE1 via a sixth contact hole CH6 and a second common electrode CE2 connected to the driving voltage line DVL.

Referring to FIGS. 4 and 5, the display device 10 according to an embodiment includes the thin film transistors TFT1 and TFT2 and a base substrate BS for laminating the organic light emitting device OEL.

The display device includes the organic light emitting device OEL according to an embodiment, and detailed description on the configuration of the organic light emitting device will not be repeatedly explained and other configuration of the display device will be explained.

In the display device, a suitable substrate may be used as the base substrate BS, and may be formed using an insulating material, e.g., glass, plastics, and quartz. As an organic polymer forming the base substrate BS, polyethylene terephthalate (PET), polyethylene naphthalate (PEN), polyimide, polyethersulfone, etc. may be used. The base substrate BS may be selected in consideration of mechanical strength, thermal stability, transparency, surface smoothness, easiness of handling, water-proof properties, etc.

On the base substrate BS, a substrate buffer layer may be provided. The substrate buffer layer may help prevent the diffusion of impurities into the switching thin film transistor TFT1 and the driving thin film transistor TFT2. In an implementation, the substrate buffer layer may be formed using silicon nitride (SiNx), silicon oxide (SiOx), silicon oxynitride (SiOxNy), etc., and may be omitted according to the material of the base substrate BS and process conditions.

On the base substrate BS, a first semiconductor layer SM1 and a second semiconductor layer SM2 may be provided. The first semiconductor layer SM1 and the second semiconductor layer SM2 may be formed using a semiconductor material and function as active layers of the switching thin film transistor TFT1 and the driving thin film transistor TFT2, respectively. Each of the first semiconductor layer SM1 and the second semiconductor layer SM2 may include a source area SA, a drain area DRA, and a channel area CA provided between the source area SA and the drain area DRA. Each of the first semiconductor layer SM1 and the second semiconductor layer SM2 may be formed by selecting inorganic semiconductor or organic semiconductor, respectively. The source area SA and the drain area DA may be doped with n-type impurities or p-type impurities.

On the first semiconductor layer SM1 and the second semiconductor layer SM2, a gate insulating layer GI may be provided. The gate insulating layer GI may cover the first semiconductor layer SM1 and the second semiconductor layer SM2. The gate insulating layer GI may include at least one of an organic insulating material or an inorganic insulating material.

On the gate insulating layer GI, a first gate electrode GE1 and a second gate electrode GE2 may be provided. Each of the first gate electrode GE1 and the second gate electrode GE2 may be formed to cover a corresponding area to the channel area CA of the first semiconductor layer SM1 or the second semiconductor layer SM2.

On the first gate electrode GE1 and the second gate electrode GE2, an insulating interlayer IL is provided. The insulating interlayer IL covers the first gate electrode GE1 and the second gate electrode GE2. The insulating interlayer IL may be formed using an organic insulating material or an inorganic insulating material.

On the insulating interlayer IL, a first source electrode SE1, a first drain electrode DE1, a second source electrode SE2, and a second drain electrode DE2 may be provided. The second drain electrode DE2 may make contact with the drain area DRA of the second semiconductor layer SM2 via a first contact hole CH1 formed in the gate insulating layer GI and the insulating interlayer IL, and the second source electrode SE2 may make contact with the source area SA of a second semiconductor layer SM2 by a second contact hole CH2 formed in the gate insulating layer GI and the insulating interlayer IL. The first source electrode SE1 may make contact with a source area (not shown) of the first semiconductor layer SM1 via a fourth contact hole CH4 formed in the gate insulating layer GI and the insulating interlayer IL, and the first drain electrode DE1 may make contact with a drain area (not shown) of the first semiconductor layer SM1 via a fifth contact hole CH5 formed in the gate insulating layer GI and the insulating interlayer IL.

On the first source electrode SE1, the first drain electrode DE1, the second source electrode SE2, and the second drain electrode DE2, a passivation layer PSL is provided. The passivation layer PL may play the role of passivating the switching thin film transistor TFT1 and the driving thin film transistor TFT2, or the role of a planarizing layer for planarizing the top surface thereof.

On the passivation layer PL, a first electrode EL1 is provided. The first electrode EL1 may be, for example, an anode. The first electrode EL1 may be connected to the second drain electrode DE2 of the driving thin film transistor TFT2 via the third contact hole CH3 formed in the passivation layer PL.

On the passivation layer PL, a pixel defining layer PDL partitioning pixel areas (PA in FIG. 4) so as to correspond to each of the pixels PX is provided. The pixel defining layer PDL exposes the top surface of the first electrode EL1 and protruded from the base substrate BS along respective circumference of each of the pixels PX. The pixel defining layer PDL may include a metal-fluorine ion compound. For example, the pixel defining layer PDL may be composed of a metal-fluorine ion compound of LiF, $BaF_2$, or CsF. In the case where the metal-fluorine ion compound has a certain thickness, insulating property may be attained. The thickness of the pixel defining layer PDL may be, for example, from about 10 nm to about 100 nm.

To respective pixel area (PA in FIG. 2) surrounded by the pixel defining layer PDL, an organic light emitting device OEL is provided. As the organic light emitting device OEL, an organic light emitting device according to the above-described embodiment may be provided. The organic light emitting device may include a first electrode EL1, a hole controlling layer HCL, an emission layer EML, an electron controlling layer ECL, and a second electrode EL2. In addition, the emission layer EML may include three host materials and at least one dopant material.

By way of summation and review, an organic light emitting device may include an emission layer that includes a host material for phosphorescence. As the host material for phosphorescence, 4,4'-N,N'-dicarbazole-biphenyl (CBP), etc. may be used. In the case where a single host material is used in the emission layer, efficiency and emission life of a device may be insufficient.

The display device according to an embodiment may include three different kinds of host materials, e.g., the hole transport host, the electron transport host, and the bipolar host material in the emission layer, and may help improve emission efficiency. In addition, the life of the display device according to an embodiment may be extended.

In exemplary embodiments, three kinds of host materials may be included in an emission layer, and an organic light emitting device and a display device having improved emission efficiency and life may be provided.

The embodiments may provide an organic light emitting device and a display device, including a plurality of host materials in an emission layer and having improved efficiency and emission life.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic light emitting device, comprising:
a first electrode;
a hole controlling layer disposed on the first electrode;
an emission layer disposed on the hole controlling layer;
an electron controlling layer disposed on the emission layer; and
a second electrode disposed on the electron controlling layer,
wherein the emission layer includes a hole transport host compound, an electron transport host compound, a bipolar host compound, and at least one dopant material, and
wherein the hole transport host compound, the electron transport host compound, and the bipolar host compound are different from one another.

2. The organic light emitting device as claimed in claim 1, wherein the bipolar host compound is a compound represented by the following Formula 1:

[Formula 1]

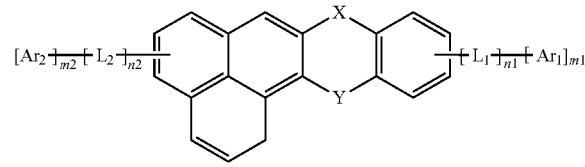

wherein, in Formula 1,
X and Y are each independently one of NR, S, O or Si,
R is a substituted or unsubstituted aryl group having 6 to 40 ring carbon atoms, or a substituted or unsubstituted heteroaryl group having 5 to 40 ring carbon atoms,
$L_1$ and $L_2$ are each independently selected from hydrogen, deuterium, a halogen atom, an amino group, a nitro group, a nitrile group, an alkyl group having 1 to 40 carbon atoms, an alkenyl group having 2 to 40 carbon atoms, an alkynyl group having 2 to 40 carbon atoms, an aryl group having 5 to 40 ring carbon atoms, a heteroaryl group having 1 to 40 ring carbon atoms, an alkoxy group having 1 to 40 carbon atoms, an aryloxy group having 5 to 40 carbon atoms, an alkylamino group having 1 to 40 carbon atoms, an arylamino group having 5 to 40 carbon atoms, a diarylamino group having 5 to 40 carbon atoms, a heteroarylamino group having 5 to 40 carbon atoms, a diheteroarylamino group having 2 to 40 carbon atoms, an arylakyl group having 6 to 40 carbon atoms, a heteroarylalkyl group having 6 to 40 carbon atoms, a cycloalkyl group having 3 to 40 carbon atoms, a halogenalkyl group having 1 to 40 carbon atoms, a heterocycloalkyl group having 3 to 40 carbon atoms, an alkylsilyl group having 3 to 40 carbon atoms, an arylsilyl group having 3 to 40 carbon atoms, and a heteroarylsilyl group having 3 to 40 carbon atoms, Ar$_1$ and Ar$_2$ are each independently selected from a substituted or unsubstituted aryl group having 5 to 60 ring carbon atoms, a substituted or unsubstituted heteroaryl group having 3 to 60 ring carbon atoms, and a substituted or unsubstituted condensed polycyclic group having 6 to 60 ring carbon atoms, and n1, n2, m1, and m2 are each independently 0 or 1.

3. The organic light emitting device as claimed in claim 2, wherein the bipolar host compound represented by Formula 1 is represented by the following Formula 2:

[Formula 2]

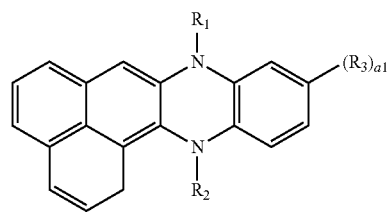

wherein, in Formula 2,

R$_1$ to R$_3$ are each independently a substituted or unsubstituted aryl group having 6 to 40 ring carbon atoms or a substituted or unsubstituted heteroaryl group having 5 to 40 ring carbon atoms, and a1 is 0 or 1.

4. The organic light emitting device as claimed in claim 3, wherein:

at least one of R$_1$ to R$_3$ is the substituted or unsubstituted heteroaryl group having 5 to 40 ring carbon atoms, and the substituted or unsubstituted heteroaryl group having 5 to 40 ring carbon atoms includes a heteroatom selected from N, S, or O.

5. The organic light emitting device as claimed in claim 3, wherein R$_1$ to R$_3$ are each independently one of the following groups:

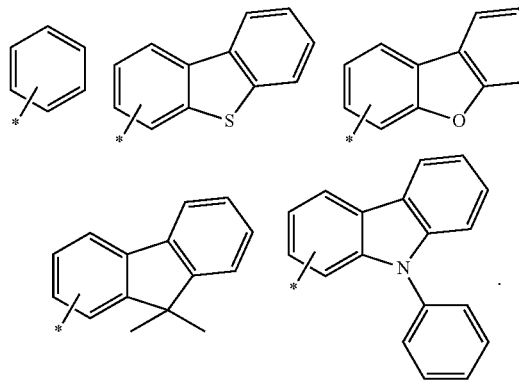

6. The organic light emitting device as claimed in claim 2, wherein the bipolar host compound represented by Formula 1 is one of the following Compounds H-1 to H-9:

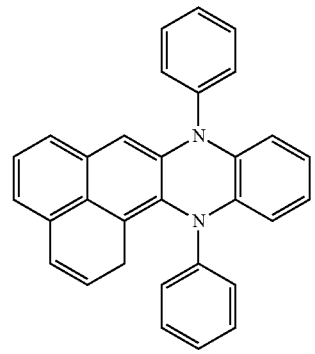

H-1

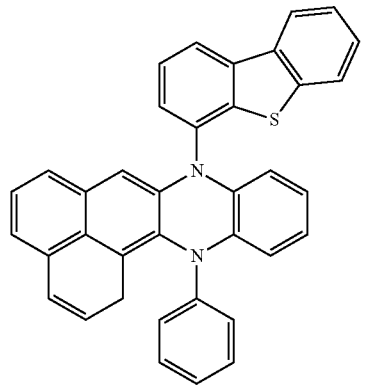

H-2

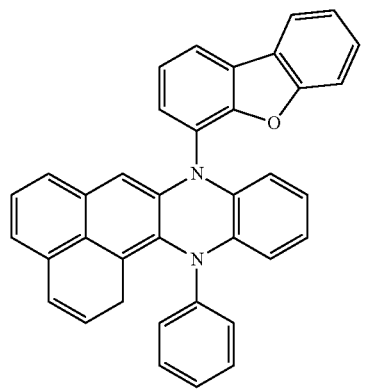

H-3

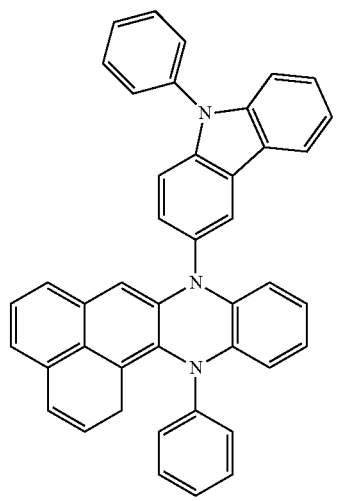

H-4

H-5

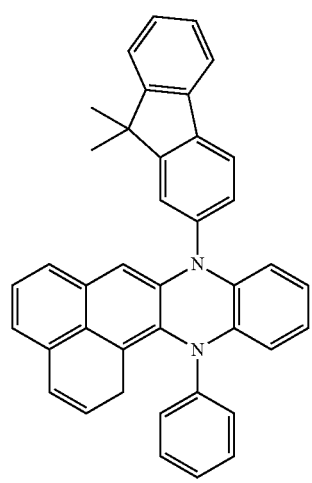

H-6

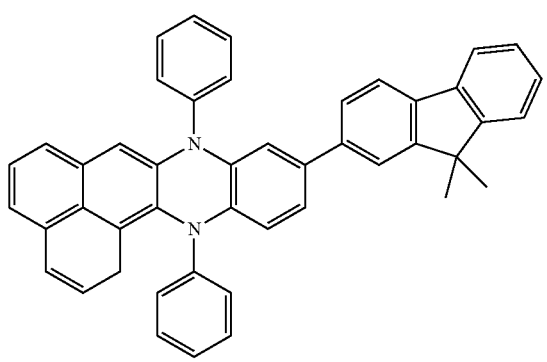

H-7

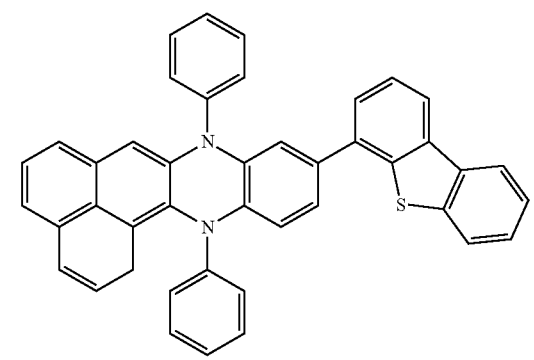

H-8

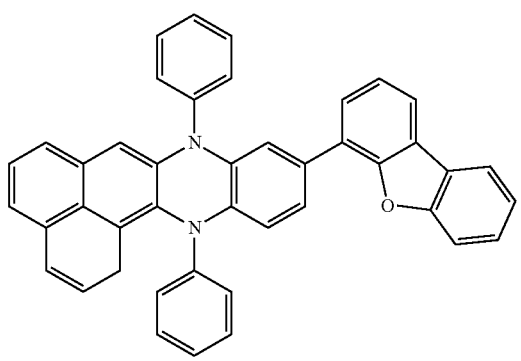

H-9

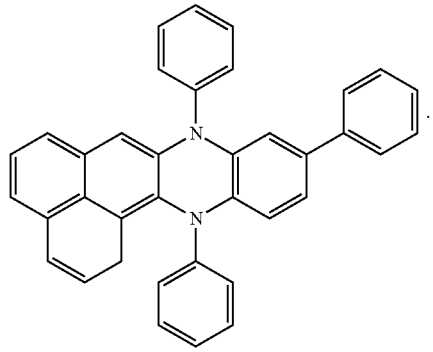

7. The organic light emitting device as claimed in claim 2, wherein the bipolar host compound represented by Formula 1 is represented by the following Formula 5:

[Formula 5]

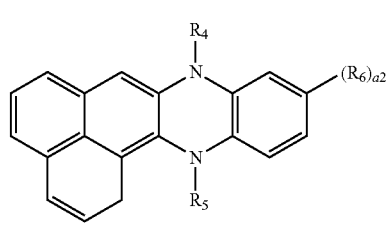

wherein, in Formula 5,
a2 is 0 or 1, and
$R_4$ to $R_6$ are each independently a substituted or unsubstituted aryl group having 6 to 40 ring carbon atoms or a substituted or unsubstituted heteroaryl group having 5 to 40 ring carbon atoms, the substituted groups being substituted with one of the following substituents:

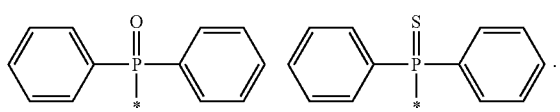

8. The organic light emitting device as claimed in claim 2, wherein the bipolar host compound represented by Formula 1 is one of the following Compounds E-1 to E-12:

E-1

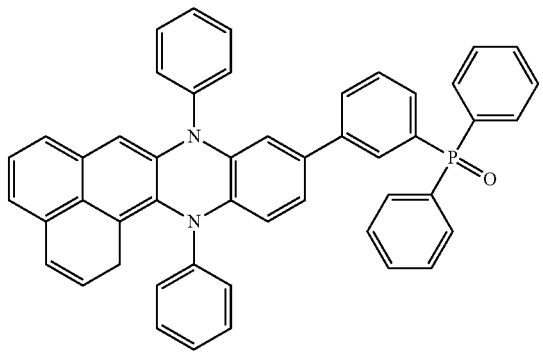

-continued
E-2
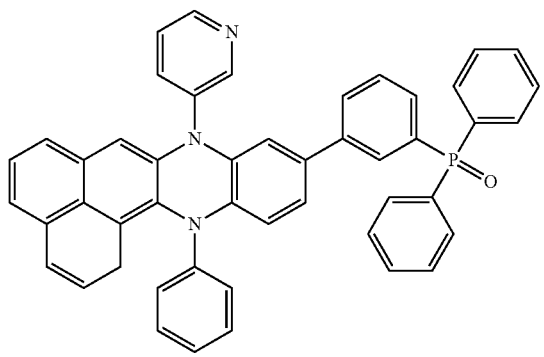
E-3
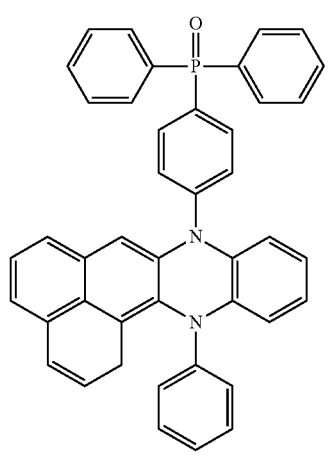
E-4
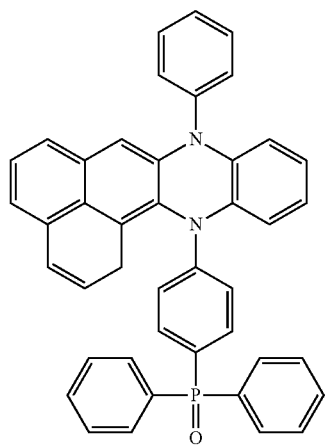
E-5
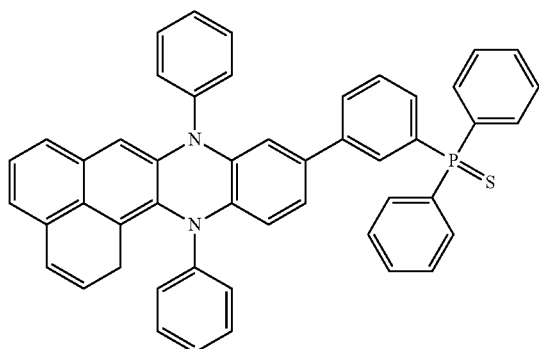
-continued
E-6
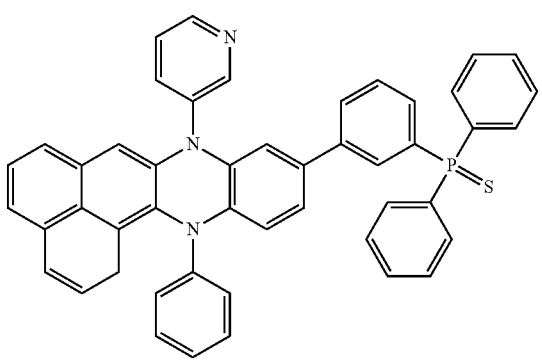
E-7
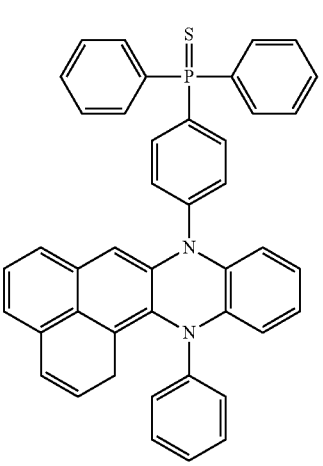
E-8
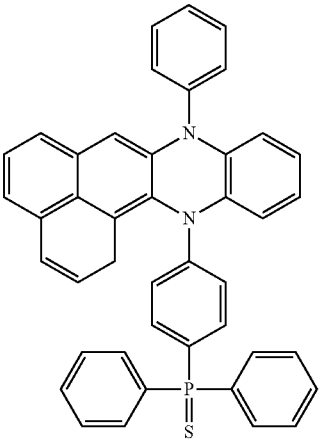
E-9
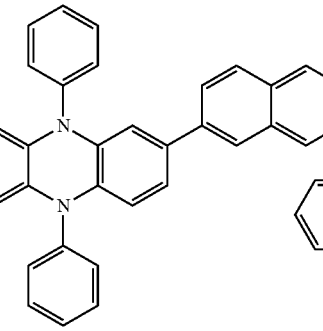

-continued

E-10

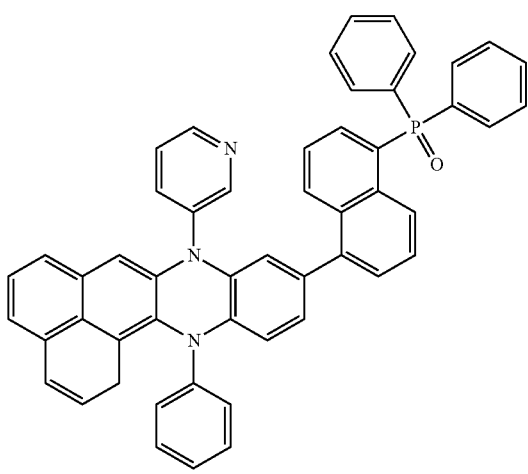

E-11

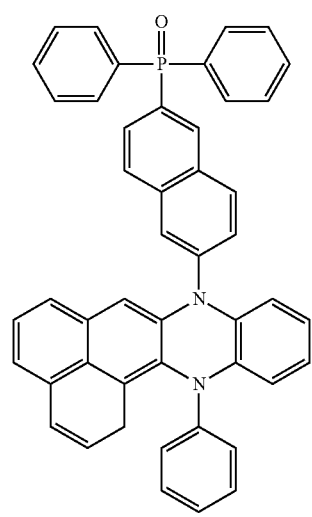

E-12

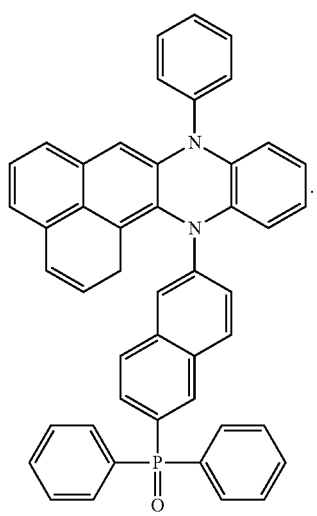

9. The organic light emitting device as claimed in claim 1, wherein the hole transport host compound is a compound represented by the following Formula 8:

[Formula 8]

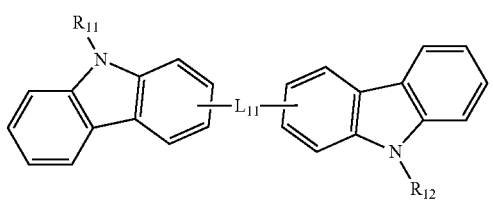

wherein, in Formula 8,
$L_{11}$ is a direct linkage, a substituted or unsubstituted arylene group having 6 to 18 ring carbon atoms, or a substituted or unsubstituted heteroarylene group having 5 to 15 ring carbon atoms,
$R_{11}$ and $R_{12}$ are each independently hydrogen, a halogen atom, an alkyl group having 1 to 20 carbon atoms, a cycloalkyl group having 3 to 40 carbon atoms, a substituted or unsubstituted aryl group having 6 to 50 ring carbon atoms, or a substituted or unsubstituted heteroaryl group having 5 to 50 ring carbon atoms.

10. The organic light emitting device as claimed in claim 9, wherein the hole transport host compound represented by Formula 8 is one of the following Compounds A-1 to A-16:

A-1

A-2

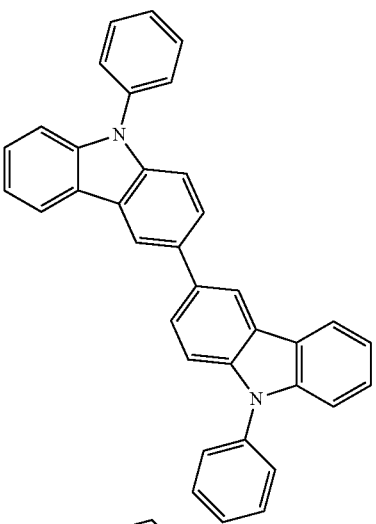

A-3
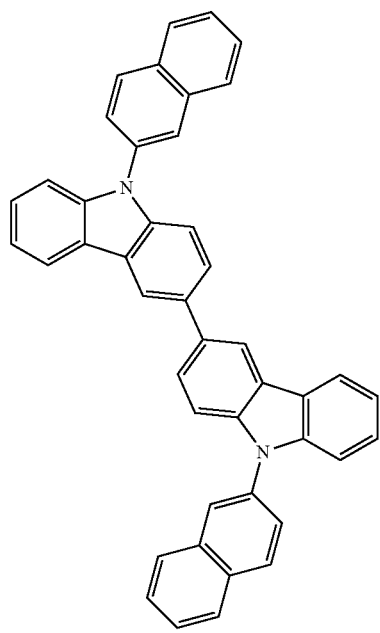
A-4
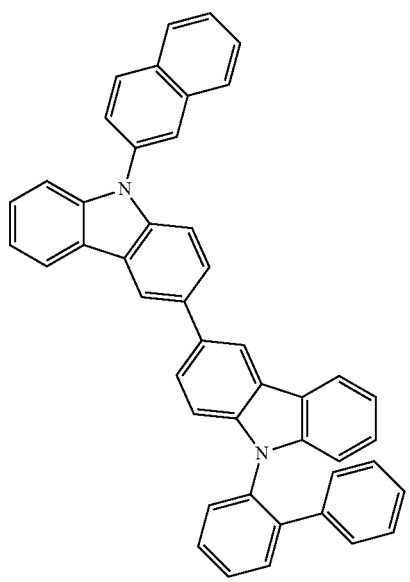
A-5
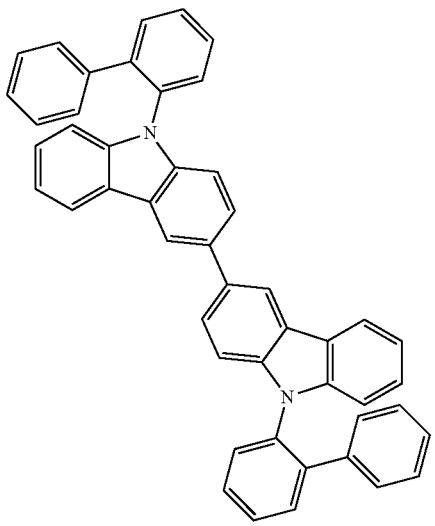
A-6
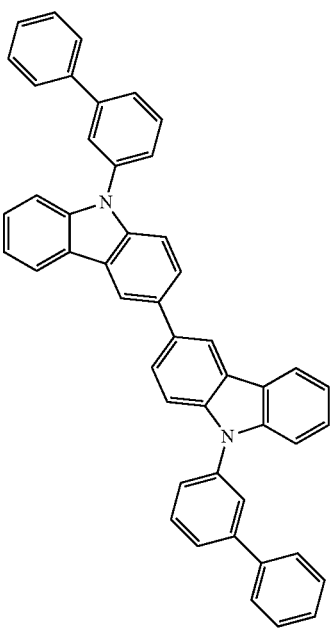

A-7
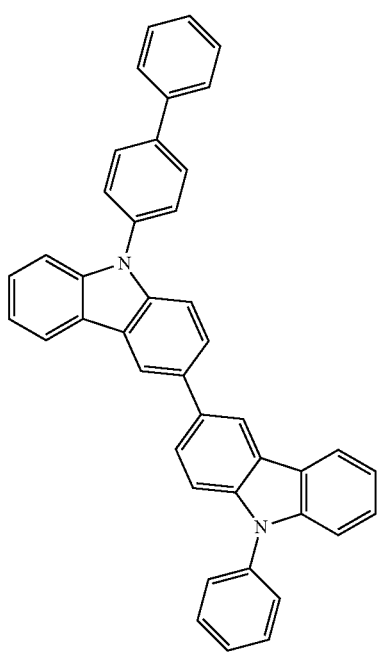
A-8
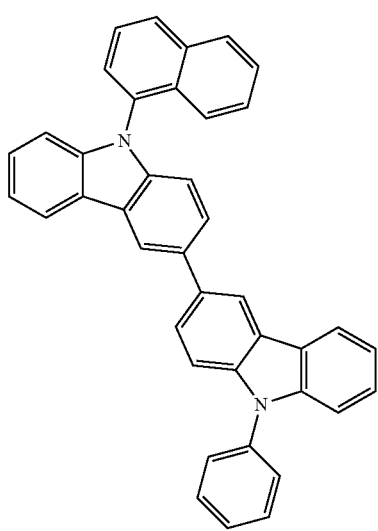
A-9
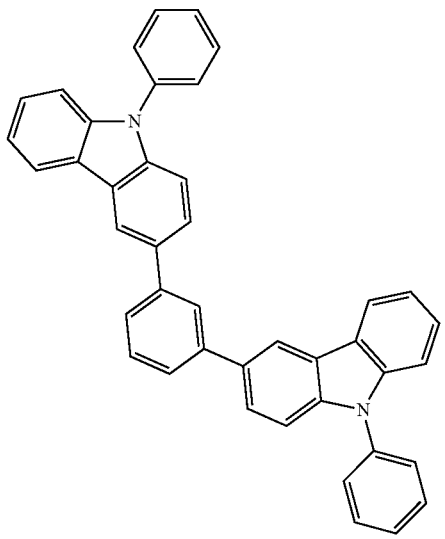
A-10
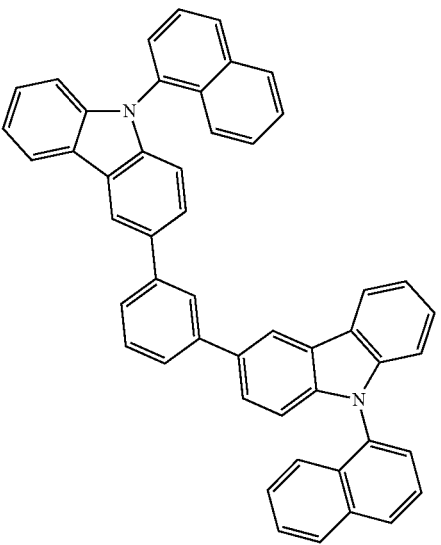

A-11
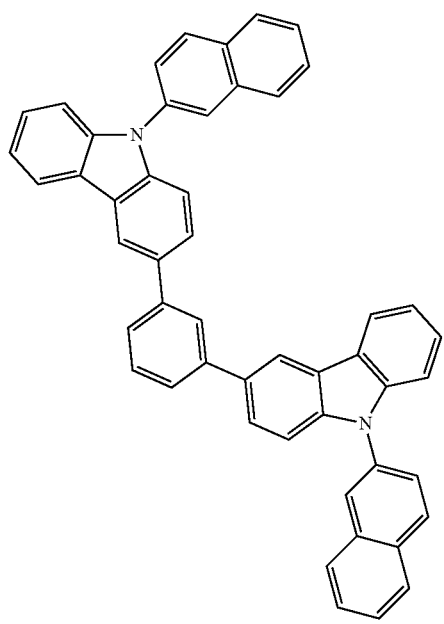
A-13
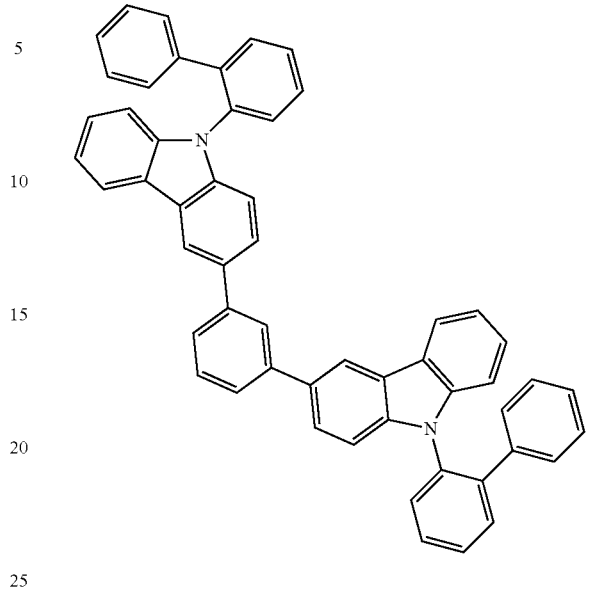
A-12
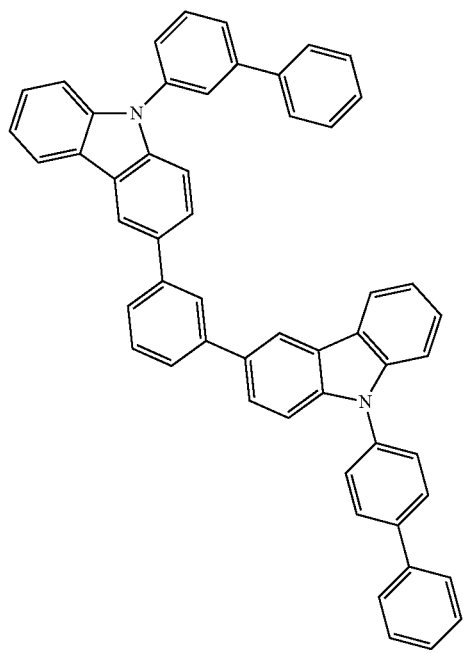
A-14
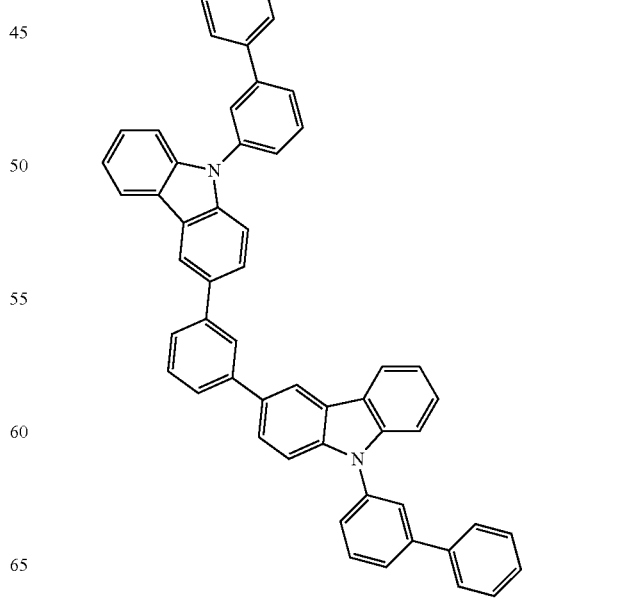

A-15

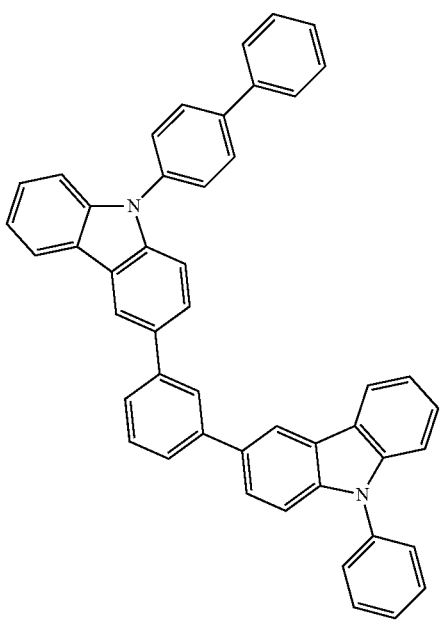

A-16

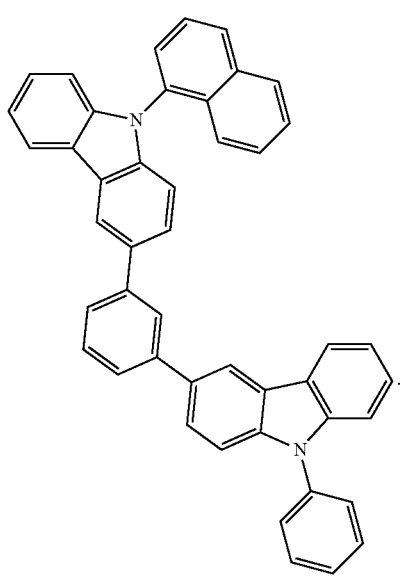

11. The organic light emitting device as claimed in claim 1, wherein the electron transport host compound is a compound represented by the following Formula 10:

[Formula 10]

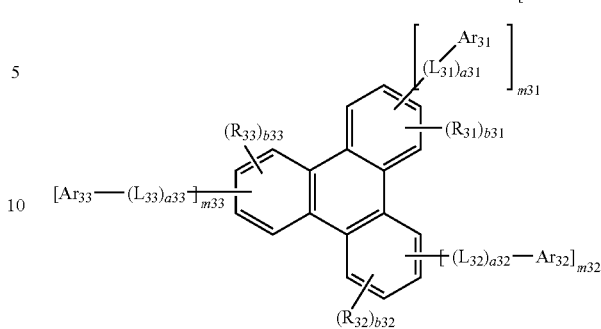

wherein, in Formula 10, $L_{31}$ to $L_{33}$ are each independently selected from a substituted or unsubstituted cycloalkylene group having 3 to 10 carbon atoms, a substituted or unsubstituted heterocycloalkylene group having 1 to 10 carbon atoms, a substituted or unsubstituted cycloalkenylene group having 3 to 10 carbon atoms, a substituted or unsubstituted heterocycloalkenylene group having 1 to 10 carbon atoms, a substituted or unsubstituted arylene group having 6 to 60 ring carbon atoms, a substituted or unsubstituted heteroarylene group having 1 to 60 ring carbon atoms, a substituted or unsubstituted divalent nonaromatic carbocyclic condensed polycyclic group and a substituted or unsubstituted divalent nonaromatic heterocyclic condensed polycyclic group;

$Ar_{31}$ to $Ar_{33}$ are each independently selected from a substituted or unsubstituted aryl group having 6 to 60 ring carbon atoms, a substituted or unsubstituted heteroaryl group having 1 to 60 ring carbon atoms, a substituted or unsubstituted monovalent nonaromatic carbocyclic condensed polycyclic group, and a substituted or unsubstituted monovalent nonaromatic heterocyclic condensed polycyclic group;

$R_{31}$ to $R_{33}$ are each independently hydrogen, deuterium, a halogen atom, a hydroxyl group, a cyano group, a nitro group, an amino group, an amidino group, a hydrazine group, a hydrazone group, a carboxylate or a salt thereof, a sulfonate or a salt thereof, a phosphate or a salt thereof, a substituted or unsubstituted alkyl group having 1 to 60 carbon atoms, a substituted or unsubstituted alkenyl group having 2 to 60 carbon atoms, a substituted or unsubstituted alkynyl group having 2 to 60 carbon atoms, a substituted or unsubstituted alkoxy group having 1 to 60 carbon atoms, a substituted or unsubstituted cycloalkyl group having 3 to 10 carbon atoms, a substituted or unsubstituted heterocycloalkyl group having 1 to 10 carbon atoms, a substituted or unsubstituted cycloalkenyl group having 3 to 10 carbon atoms, a substituted or unsubstituted heterocycloalkenyl group having 1 to 10 carbon atoms, a substituted or unsubstituted aryl group having 6 to 60 ring carbon atoms, a substituted or unsubstituted aryloxy group having 6 to 60 carbon atoms, a substituted or unsubstituted arylthio group having 6 to 60 carbon atoms, a substituted or unsubstituted heteroaryl group having 1 to 60 ring carbon atoms ring, a substituted or unsubstituted monovalent nonaromatic carbocyclic condensed polycyclic group, or a substituted or unsubstituted monovalent nonaromatic heterocyclic condensed polycyclic group;

a31, a32, a33, and b31 are each independently an integer of 0 to 3;
b32 b33, m32, and m33 are each independently an integer of 0 to 4; and
m31 is an integer of 1 to 4.

12. The organic light emitting device as claimed in claim 11, wherein, in Formula 10, m31 is 1, m32 is 0, and m33 is 0.

13. The organic light emitting device as claimed in claim 11, wherein, in Formula 10, $R_{31}$ to $R_{33}$ are each independently selected from hydrogen, deuterium, a halogen atom, a methyl group, an ethyl group, an n-propyl group, an iso-propyl group, an n-butyl group, an iso-butyl group, a sec-butyl group, a tert-butyl group, a phenyl group, a naphthyl group, a pyridyl group, a pyrimidyl group, a pyrazinyl group, a fluorenyl group, and a carbazole group.

14. The organic light emitting device as claimed in claim 11, wherein the electron transport host compound represented by Formula 10 is one of the following Compounds B-1 to B-20:

B-1
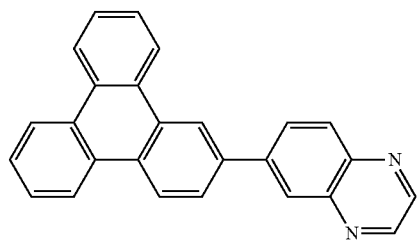

B-2
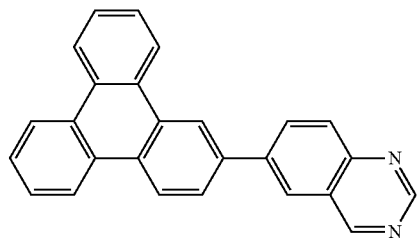

B-3
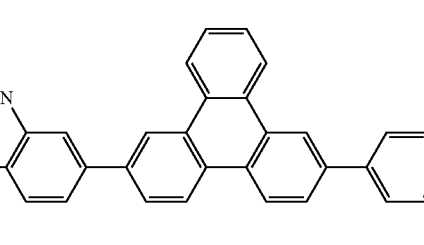

B-4
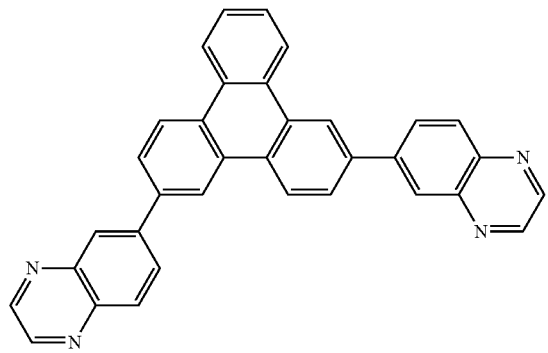

B-5
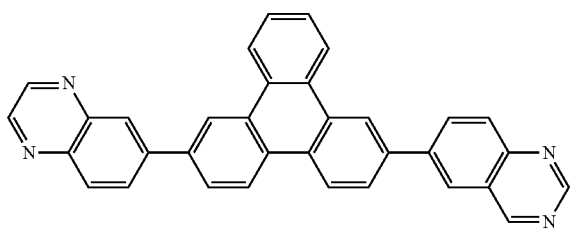

B-6
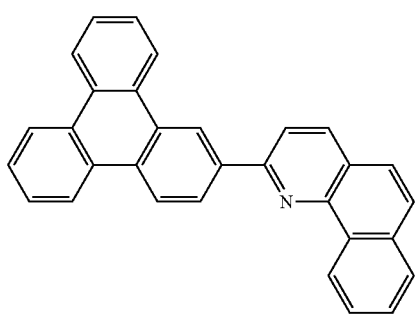

B-7
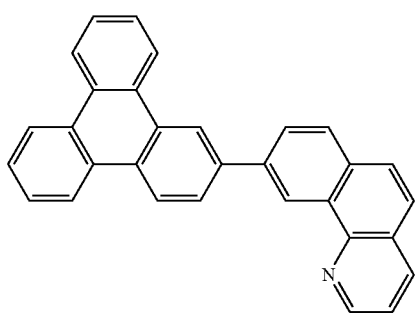

B-8
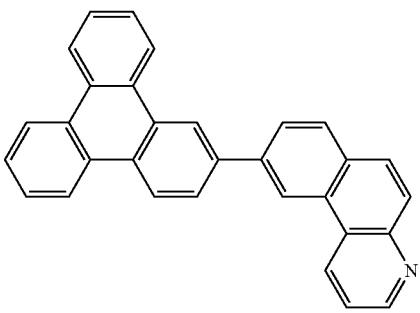

B-9
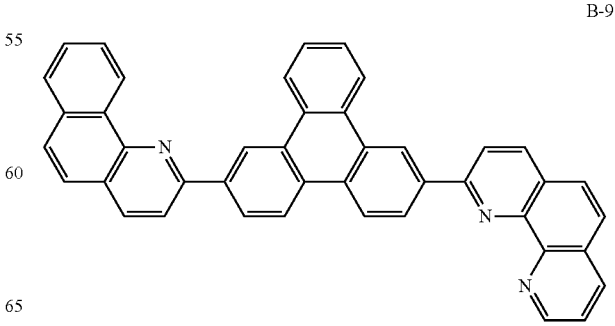

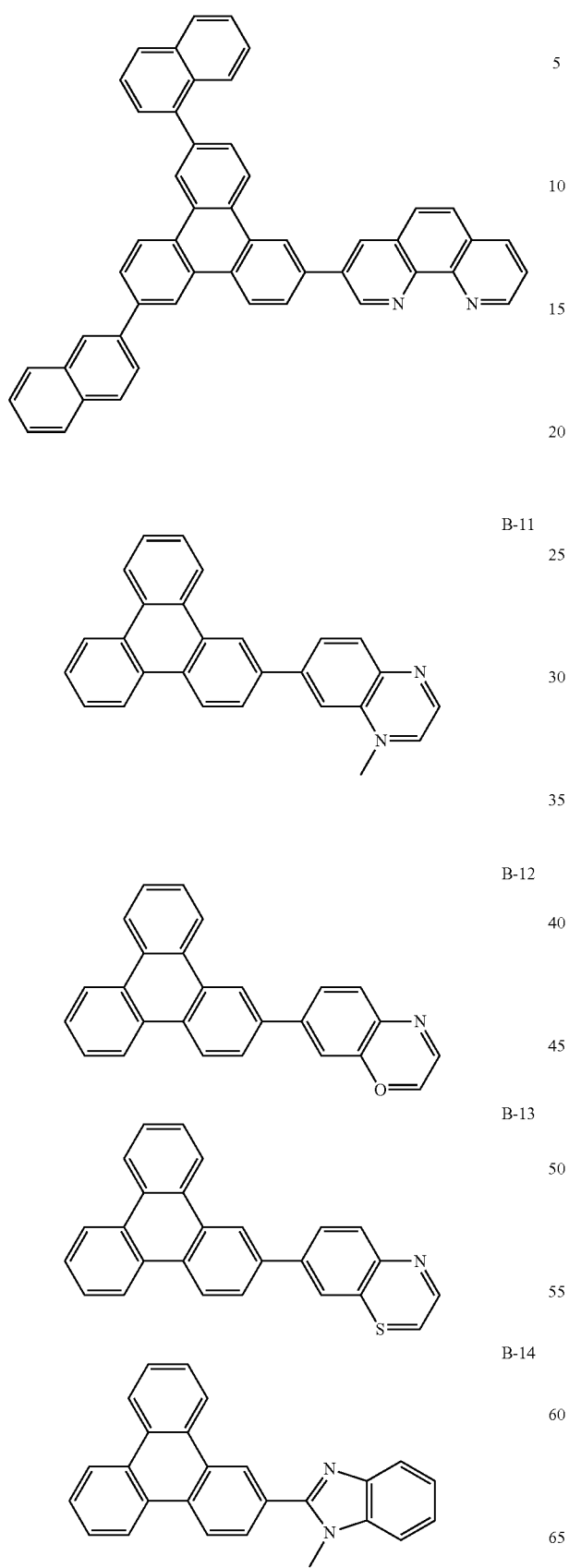
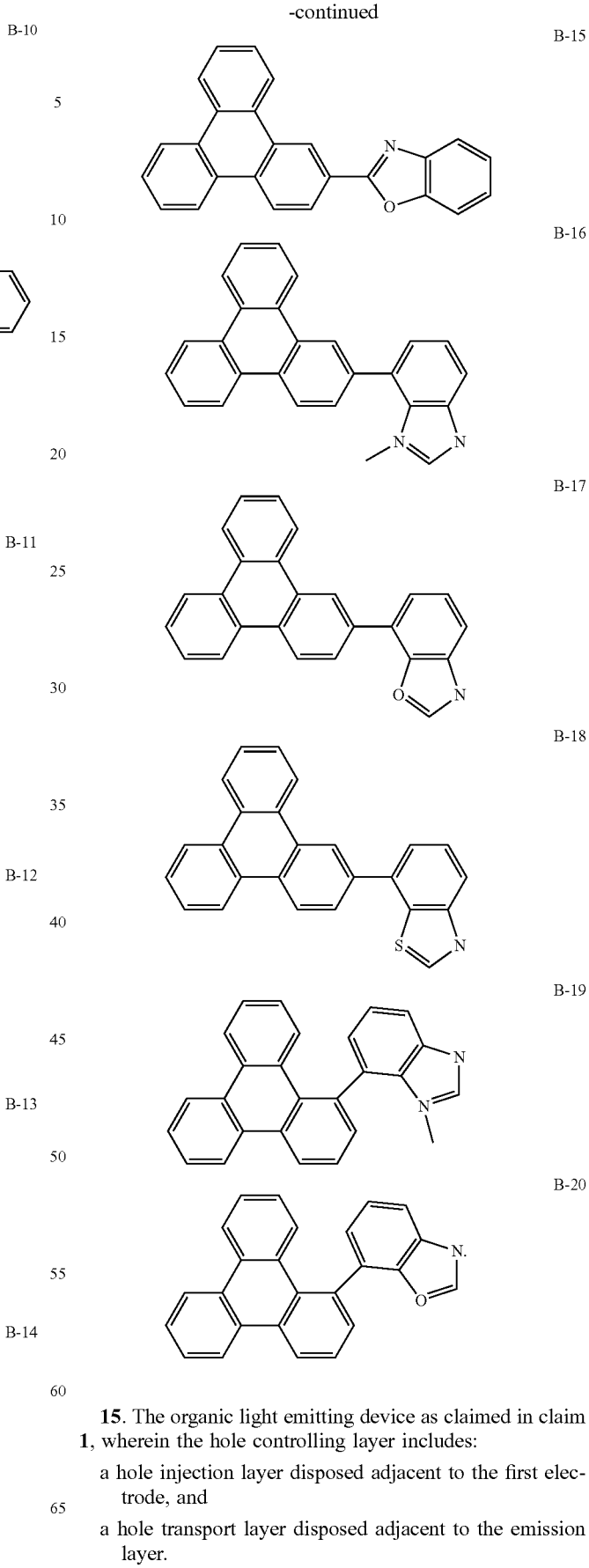
15. The organic light emitting device as claimed in claim 1, wherein the hole controlling layer includes:
   a hole injection layer disposed adjacent to the first electrode, and
   a hole transport layer disposed adjacent to the emission layer.

16. The organic light emitting device as claimed in claim 1, wherein the electron controlling layer includes:
an electron transport layer disposed adjacent to the emission layer, and
an electron injection layer disposed adjacent to the second electrode.

17. A display device comprising a plurality of pixels, wherein at last one pixel of the plurality of pixels includes:
a first electrode;
a hole controlling layer disposed on the first electrode;
an emission layer disposed on the hole controlling layer;
an electron controlling layer disposed on the emission layer; and
a second electrode disposed on the electron controlling layer,
wherein the emission layer includes a hole transport host compound, an electron transport host compound, a bipolar host compound, and at least one dopant material, and
wherein the hole transport host compound, the electron transport host compound, and the bipolar host compound are different from one another.

18. The display device as claimed in claim 17, wherein the bipolar host compound is a compound represented by the following Formula 1:

[Formula 1]

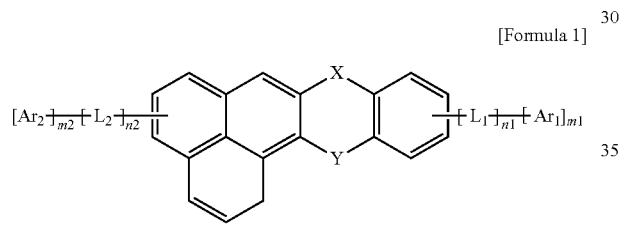

wherein, in Formula 1,
X and Y are each independently one of NR, S, O or Si,
R is a substituted or unsubstituted aryl group having 6 to 40 ring carbon atoms or a substituted or unsubstituted heteroaryl group having 5 to 40 ring carbon atoms,
$L_1$ and $L_2$ are each independently selected from hydrogen, deuterium, a halogen atom, an amino group, a nitro group, a nitrile group, an alkyl group having 1 to 40 carbon atoms, an alkenyl group having 2 to 40 carbon atoms, an alkynyl group having 2 to 40 carbon atoms, an aryl group having 5 to 40 ring carbon atoms, a heteroaryl group having 1 to 40 ring carbon atoms, an alkoxy group having 1 to 40 carbon atoms, an aryloxy group having 5 to 40 carbon atoms, an alkylamino group having 1 to 40 carbon atoms, an arylamino group having 5 to 40 carbon atoms, a diarylamino group having 5 to 40 carbon atoms, a heteroarylamino group having 5 to 40 carbon atoms, a diheteroarylamino group having 2 to 40 carbon atoms, an arylakyl group having 6 to 40 carbon atoms, a heteroarylalkyl group having 6 to 40 carbon atoms, a cycloalkyl group having 3 to 40 carbon atoms, a halogenalkyl group having 1 to 40 carbon atoms, a heterocycloalkyl group having 3 to 40 carbon atoms, an alkylsilyl group having 3 to 40 carbon atoms, an arylsilyl group having 3 to 40 carbon atoms, and a heteroarylsilyl group having 3 to 40 carbon atoms, $Ar_1$ and $Ar_2$ are each independently selected from a substituted or unsubstituted aryl group having 5 to 60 ring carbon atoms, a substituted or unsubstituted heteroaryl group having 3 to 60 ring carbon atoms, and a substituted or unsubstituted condensed polycyclic group having 6 to 60 ring carbon atoms, and n1, n2, m1 and m2 are each independently 0 or 1.

19. The display device as claimed in claim 18, wherein the bipolar host compound represented by Formula 1 is one of the following Compounds H-1 to H-9:

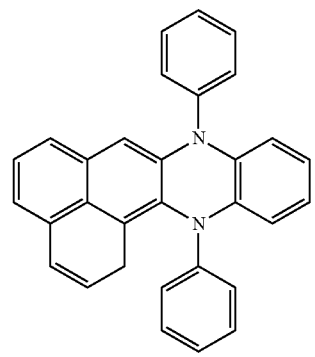
H-1

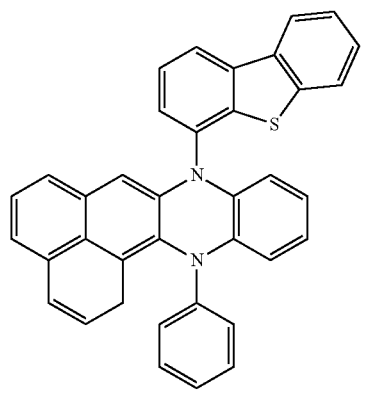
H-2

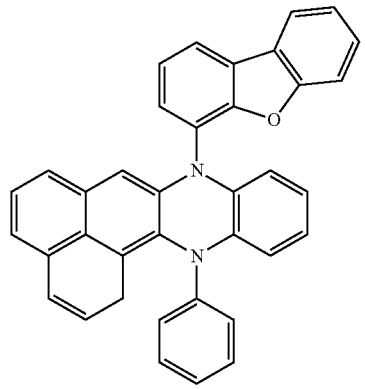
H-3

H-4
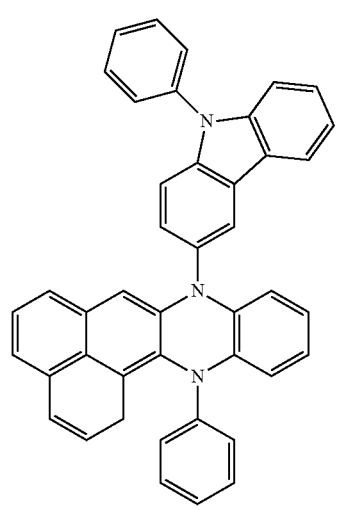
H-7
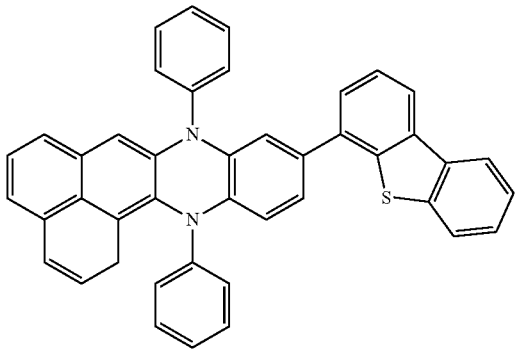
H-8
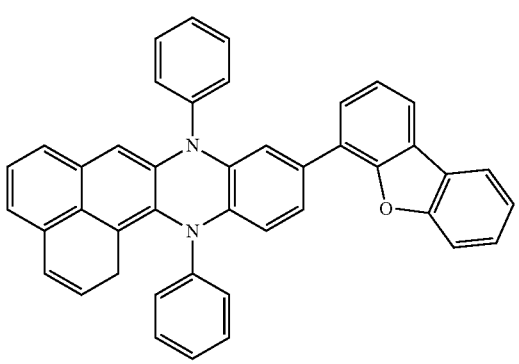
H-5
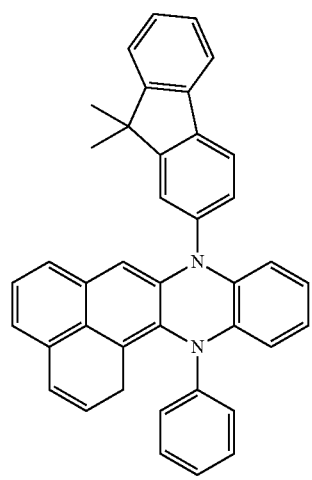
H-9
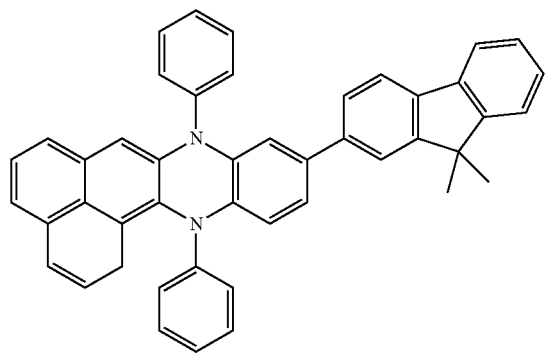
20. The display device as claimed in claim 18, wherein the bipolar host compound represented by Formula 1 is one of the following Compounds E-1 to E-12:
H-6
E-1
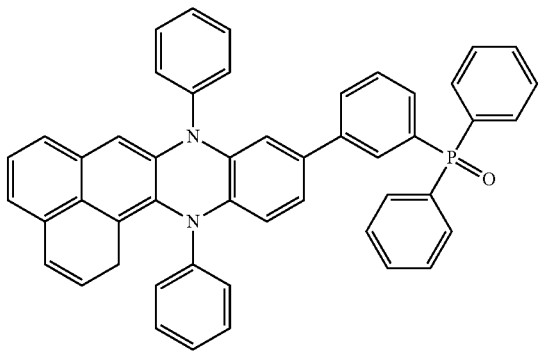

E-2
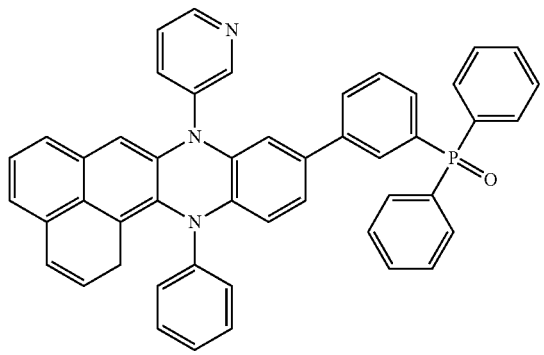
E-3
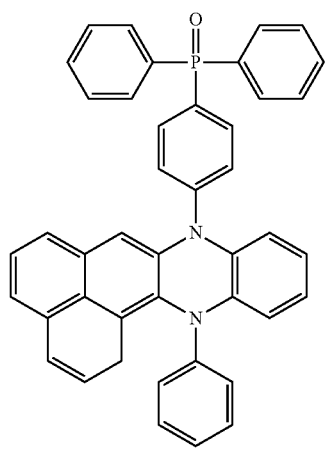
E-4
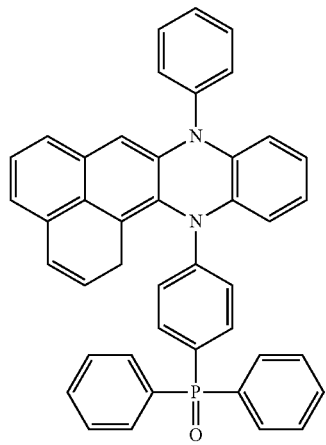
E-5
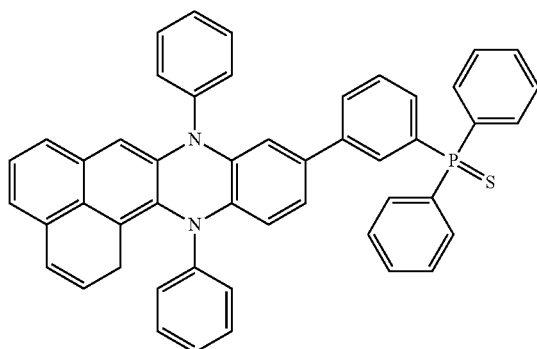
E-6
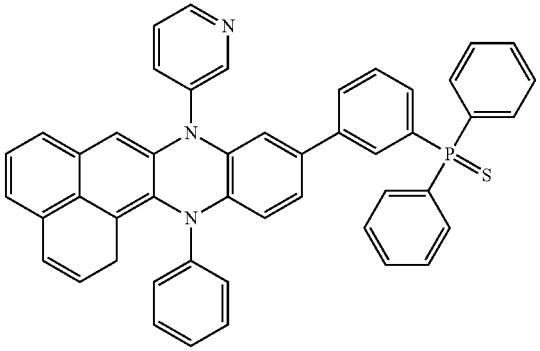
E-7
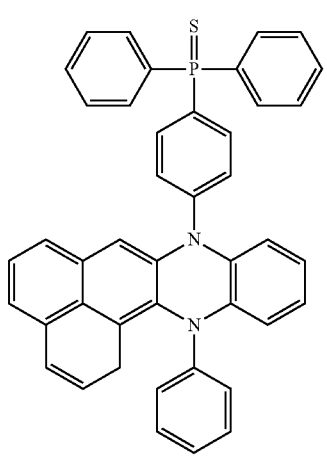
E-8
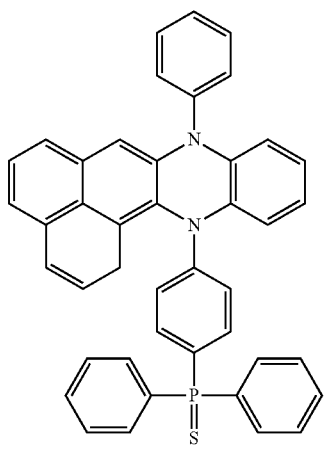

-continued
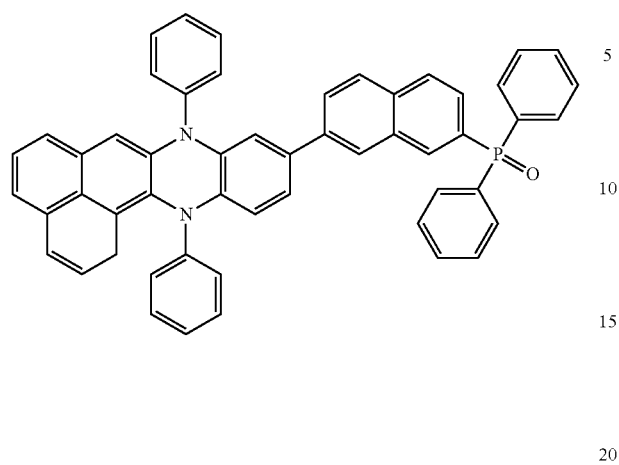
E-9
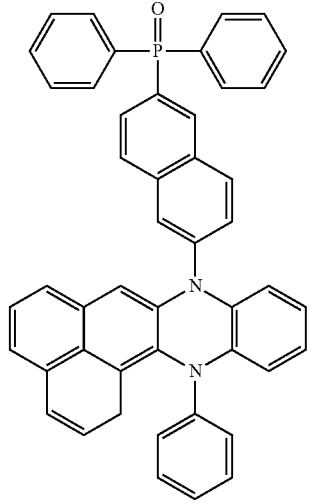
E-11
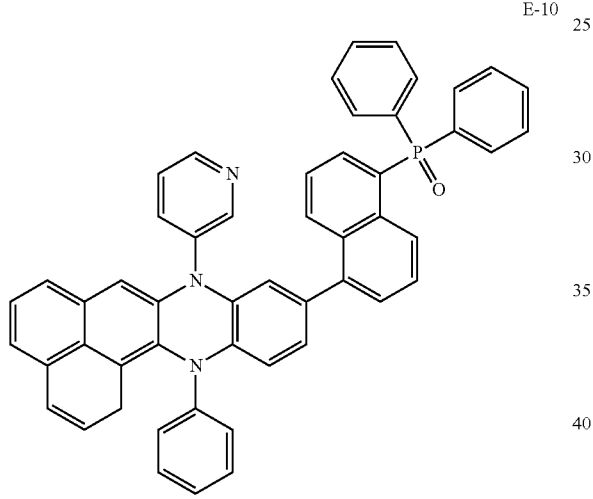
E-10
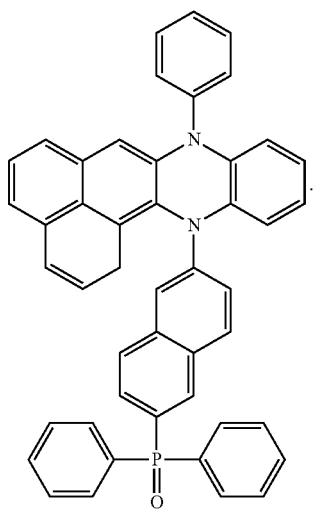
E-12
* * * * *